(12) United States Patent
Fennell

(10) Patent No.: US 12,279,894 B2
(45) Date of Patent: Apr. 22, 2025

(54) ANALYTE SIGNAL PROCESSING DEVICE AND METHODS

(71) Applicant: ABBOTT DIABETES CARE INC., Alameda, CA (US)

(72) Inventor: Martin J. Fennell, Concord, CA (US)

(73) Assignee: ABBOTT DIABETES CARE INC., Alameda, CA (US)

(*) Notice: Subject to any disclaimer, the term of this patent is extended or adjusted under 35 U.S.C. 154(b) by 0 days.

(21) Appl. No.: 17/361,089

(22) Filed: Jun. 28, 2021

(65) Prior Publication Data
US 2021/0321950 A1 Oct. 21, 2021

Related U.S. Application Data

(63) Continuation of application No. 15/953,378, filed on Apr. 13, 2018, now Pat. No. 11,045,147, which is a
(Continued)

(51) Int. Cl.
*A61B 5/00* (2006.01)
*A61B 5/145* (2006.01)
(Continued)

(52) U.S. Cl.
CPC ............ *A61B 5/7228* (2013.01); *A61B 5/002* (2013.01); *A61B 5/14532* (2013.01);
(Continued)

(58) Field of Classification Search
CPC .................. A61B 5/7228; A61B 5/002; A61B 5/14532; A61B 5/1473; A61B 5/14865;
(Continued)

(56) References Cited

U.S. PATENT DOCUMENTS 4,003,379 A 1/1977 Ellinwood, Jr.
4,008,717 A 2/1977 Kowarski
(Continued)

FOREIGN PATENT DOCUMENTS

EP 1579690 11/2002
EP 1 391 728 2/2004
(Continued)

OTHER PUBLICATIONS

K. S. Kanukurthy, M. B. Cover and D. R. Andersen, "Data acquisition unit for an implantable multi-channel optical glucose sensor," 2007 IEEE International Conference on Electro/Information Technology, Chicago, IL, USA, 2007, pp. 32-37, doi: 10.1109/EIT.2007.4374503. (Year: 2007).*
(Continued)

*Primary Examiner* — Raymond L Nimox
(74) *Attorney, Agent, or Firm* — Baker Botts L.L.P.

(57) ABSTRACT

Methods and devices for determining a measurement time period, receiving a plurality of signals associated with a monitored analyte level during the determined measurement time period from an analyte sensor, modulating the received plurality of signals to generate a data stream over the measurement time period, and accumulating the generated data stream to determine an analyte signal corresponding to the monitored analyte level associated with the measurement time period are provided. Systems and kits are also described.

30 Claims, 5 Drawing Sheets

Related U.S. Application Data continuation of application No. 15/090,610, filed on Apr. 4, 2016, now Pat. No. 9,968,302, which is a continuation of application No. 12/873,294, filed on Aug. 31, 2010, now Pat. No. 9,314,195.

(60) Provisional application No. 61/238,658, filed on Aug. 31, 2009.

(51) Int. Cl.
  *A61B 5/1473* (2006.01)
  *A61B 5/1486* (2006.01)
  *G01N 15/00* (2006.01)
  *G01N 15/01* (2024.01)
  *G01N 15/06* (2006.01)

(52) U.S. Cl.
  CPC ........ *A61B 5/1473* (2013.01); *A61B 5/14865* (2013.01); *G01N 15/0606* (2013.01); *G01N 15/0656* (2013.01); *A61B 2560/0209* (2013.01); *G01N 15/01* (2024.01)

(58) Field of Classification Search
  CPC ....... A61B 2560/0209; G01N 15/0606; G01N 15/0656; G01N 2015/0065
  See application file for complete search history.

(56) References Cited

U.S. PATENT DOCUMENTS

| | | |
|---|---|---|
| 4,016,866 A | 4/1977 | Lawton |
| 4,021,718 A | 5/1977 | Konrad |
| 4,031,449 A | 6/1977 | Trombly |
| 4,036,749 A | 7/1977 | Anderson |
| 4,055,175 A | 10/1977 | Clemens et al. |
| 4,059,406 A | 11/1977 | Fleet |
| 4,076,596 A | 2/1978 | Connery et al. |
| 4,098,574 A | 7/1978 | Dappen |
| 4,100,048 A | 7/1978 | Pompei et al. |
| 4,129,128 A | 12/1978 | McFarlane |
| 4,151,845 A | 5/1979 | Clemens |
| 4,154,231 A | 5/1979 | Russell |
| 4,168,205 A | 9/1979 | Danniger et al. |
| 4,172,770 A | 10/1979 | Semersky et al. |
| 4,178,916 A | 12/1979 | McNamara |
| 4,193,026 A | 3/1980 | Finger et al. |
| 4,206,755 A | 6/1980 | Klein |
| 4,224,125 A | 9/1980 | Nakamura et al. |
| 4,240,438 A | 12/1980 | Updike et al. |
| 4,240,889 A | 12/1980 | Yoda et al. |
| 4,245,634 A | 1/1981 | Albisser et al. |
| 4,247,297 A | 1/1981 | Berti et al. |
| 4,271,449 A | 6/1981 | Grogan |
| 4,318,784 A | 3/1982 | Higgins et al. |
| 4,327,725 A | 5/1982 | Cortese et al. |
| 4,331,869 A | 5/1982 | Rollo |
| 4,340,458 A | 7/1982 | Lerner et al. |
| 4,344,438 A | 8/1982 | Schultz |
| 4,349,728 A | 9/1982 | Phillips et al. |
| 4,352,960 A | 10/1982 | Dormer et al. |
| 4,356,074 A | 10/1982 | Johnson |
| 4,365,637 A | 12/1982 | Johnson |
| 4,366,033 A | 12/1982 | Richter et al. |
| 4,375,399 A | 3/1983 | Havas et al. |
| 4,384,586 A | 5/1983 | Christiansen |
| 4,390,621 A | 6/1983 | Bauer |
| 4,392,933 A | 7/1983 | Nakamura et al. |
| 4,401,122 A | 8/1983 | Clark, Jr. |
| 4,404,066 A | 9/1983 | Johnson |
| 4,407,959 A | 10/1983 | Tsuji et al. |
| 4,417,588 A | 11/1983 | Houghton et al. |
| 4,418,148 A | 11/1983 | Oberhardt |
| 4,420,564 A | 12/1983 | Tsuji et al. |
| 4,425,920 A | 1/1984 | Bourland et al. |
| 4,427,004 A | 1/1984 | Miller et al. |
| 4,427,770 A | 1/1984 | Chen et al. |
| 4,431,004 A | 2/1984 | Bessman et al. |
| 4,436,094 A | 3/1984 | Cerami |
| 4,440,175 A | 4/1984 | Wilkins |
| 4,441,968 A | 4/1984 | Emmer et al. |
| 4,444,892 A | 4/1984 | Malmros |
| 4,445,090 A | 4/1984 | Melocik et al. |
| 4,450,842 A | 5/1984 | Zick et al. |
| 4,458,686 A | 7/1984 | Clark, Jr. |
| 4,461,691 A | 7/1984 | Frank |
| 4,464,170 A | 8/1984 | Clemens et al. |
| 4,467,811 A | 8/1984 | Clark, Jr. |
| 4,469,110 A | 9/1984 | Slama |
| 4,475,901 A | 10/1984 | Kraegen et al. |
| 4,477,314 A | 10/1984 | Richter et al. |
| 4,478,976 A | 10/1984 | Goertz et al. |
| 4,483,924 A | 11/1984 | Tsuji et al. |
| 4,484,987 A | 11/1984 | Gough |
| 4,494,950 A | 1/1985 | Fischell |
| 4,509,531 A | 4/1985 | Ward |
| 4,512,348 A | 4/1985 | Uchigaki et al. |
| 4,522,690 A | 6/1985 | Venkatsetty |
| 4,524,114 A | 6/1985 | Samuels et al. |
| 4,526,661 A | 7/1985 | Steckhan et al. |
| 4,527,240 A | 7/1985 | Kvitash |
| 4,534,356 A | 8/1985 | Papadakis |
| 4,538,616 A | 9/1985 | Rogoff |
| 4,543,955 A | 10/1985 | Schroeppel |
| 4,545,382 A | 10/1985 | Higgins et al. |
| 4,552,840 A | 11/1985 | Riffer |
| 4,560,534 A | 12/1985 | Kung et al. |
| 4,569,589 A | 2/1986 | Neufeld |
| 4,571,292 A | 2/1986 | Liu et al. |
| 4,573,994 A | 3/1986 | Fischell et al. |
| 4,581,336 A | 4/1986 | Malloy et al. |
| 4,583,035 A | 4/1986 | Sloan |
| 4,595,011 A | 6/1986 | Phillips |
| 4,595,479 A | 6/1986 | Kimura et al. |
| 4,601,707 A | 7/1986 | Albisser et al. |
| 4,619,754 A | 10/1986 | Niki et al. |
| 4,619,793 A | 10/1986 | Lee |
| 4,627,445 A | 12/1986 | Garcia et al. |
| 4,627,908 A | 12/1986 | Miller |
| 4,633,878 A | 1/1987 | Bombardien |
| 4,633,881 A | 1/1987 | Moore et al. |
| 4,637,403 A | 1/1987 | Garcia et al. |
| 4,648,408 A | 3/1987 | Hutcheson et al. |
| 4,650,547 A | 3/1987 | Gough |
| 4,653,513 A | 3/1987 | Dombrowski |
| 4,654,197 A | 3/1987 | Lilja et al. |
| 4,655,880 A | 4/1987 | Liu |
| 4,655,885 A | 4/1987 | Hill et al. |
| 4,658,463 A | 4/1987 | Sugita et al. |
| 4,671,288 A | 6/1987 | Gough |
| 4,674,652 A | 6/1987 | Aten et al. |
| 4,679,562 A | 7/1987 | Luksha |
| 4,680,268 A | 7/1987 | Clark, Jr. |
| 4,682,602 A | 7/1987 | Prohaska |
| 4,684,537 A | 8/1987 | Graetzel et al. |
| 4,685,463 A | 8/1987 | Williams |
| 4,685,903 A | 8/1987 | Cable et al. |
| 4,686,624 A | 8/1987 | Blum et al. |
| 4,703,324 A | 10/1987 | White |
| 4,703,756 A | 11/1987 | Gough et al. |
| 4,711,245 A | 12/1987 | Higgins et al. |
| 4,717,673 A | 1/1988 | Wrighton et al. |
| 4,721,601 A | 1/1988 | Wrighton et al. |
| 4,721,677 A | 1/1988 | Clark, Jr. |
| 4,726,378 A | 2/1988 | Kaplan |
| 4,726,716 A | 2/1988 | McGuire |
| 4,731,726 A | 3/1988 | Allen, III |
| 4,749,985 A | 6/1988 | Corsberg |
| 4,750,496 A | 6/1988 | Reinhardt |
| 4,757,022 A | 7/1988 | Shults et al. |
| 4,758,323 A | 7/1988 | Davis et al. |
| 4,759,371 A | 7/1988 | Franetzki |
| 4,759,828 A | 7/1988 | Young et al. |
| 4,764,416 A | 8/1988 | Ueyama et al. |
| 4,776,944 A | 10/1988 | Janata et al. |

(56) References Cited

U.S. PATENT DOCUMENTS

| | | | |
|---|---|---|---|
| 4,777,953 A | 10/1988 | Ash et al. |
| 4,779,618 A | 10/1988 | Mund et al. |
| 4,781,798 A | 11/1988 | Gough |
| 4,784,736 A | 11/1988 | Lonsdale et al. |
| 4,795,707 A | 1/1989 | Niiyama et al. |
| 4,796,634 A | 1/1989 | Huntsman et al. |
| 4,803,625 A | 2/1989 | Fu et al. |
| 4,805,624 A | 2/1989 | Yao et al. |
| 4,813,424 A | 3/1989 | Wilkins |
| 4,815,469 A | 3/1989 | Cohen et al. |
| 4,820,399 A | 4/1989 | Senda et al. |
| 4,822,337 A | 4/1989 | Newhouse et al. |
| 4,830,959 A | 5/1989 | McNeil et al. |
| 4,832,797 A | 5/1989 | Vadgama et al. |
| 4,835,372 A | 5/1989 | Gombrich et al. |
| RE32,947 E | 6/1989 | Dormer et al. |
| 4,837,049 A | 6/1989 | Byers et al. |
| 4,840,893 A | 6/1989 | Hill et al. |
| RE32,974 E | 7/1989 | Porat et al. |
| 4,844,076 A | 7/1989 | Lesho et al. |
| 4,845,035 A | 7/1989 | Fanta et al. |
| 4,847,785 A | 7/1989 | Stephens |
| 4,848,351 A | 7/1989 | Finch |
| 4,854,322 A | 8/1989 | Ash et al. |
| 4,856,340 A | 8/1989 | Garrison |
| 4,857,713 A | 8/1989 | Brown |
| 4,858,617 A | 8/1989 | Sanders |
| 4,870,561 A | 9/1989 | Love et al. |
| 4,871,351 A | 10/1989 | Feingold |
| 4,871,440 A | 10/1989 | Nagata et al. |
| 4,874,499 A | 10/1989 | Smith et al. |
| 4,874,500 A | 10/1989 | Madou et al. |
| 4,890,620 A | 1/1990 | Gough |
| 4,890,621 A | 1/1990 | Hakky |
| 4,894,137 A | 1/1990 | Takizawa et al. |
| 4,897,162 A | 1/1990 | Lewandowski et al. |
| 4,897,173 A | 1/1990 | Nankai et al. |
| 4,899,839 A | 2/1990 | Dessertine et al. |
| 4,909,908 A | 3/1990 | Ross et al. |
| 4,911,794 A | 3/1990 | Farce et al. |
| 4,917,800 A | 4/1990 | Lonsdale et al. |
| 4,919,141 A | 4/1990 | Zier et al. |
| 4,919,767 A | 4/1990 | Vadgama et al. |
| 4,920,969 A | 5/1990 | Suzuki |
| 4,920,977 A | 5/1990 | Haynes |
| 4,923,586 A | 5/1990 | Katayama et al. |
| 4,925,268 A | 5/1990 | Iyer et al. |
| 4,927,516 A | 5/1990 | Yamaguchi et al. |
| 4,931,795 A | 6/1990 | Gord |
| 4,934,369 A | 6/1990 | Maxwell |
| 4,935,105 A | 6/1990 | Churchouse |
| 4,935,345 A | 6/1990 | Guibeau et al. |
| 4,936,956 A | 6/1990 | Wrighton |
| 4,938,860 A | 7/1990 | Wogoman |
| 4,942,127 A | 7/1990 | Wada et al. |
| 4,944,299 A | 7/1990 | Silvian |
| 4,945,045 A | 7/1990 | Forrest et al. |
| 4,950,378 A | 8/1990 | Nagata |
| 4,953,552 A | 9/1990 | DeMarzo |
| 4,954,129 A | 9/1990 | Giuliani et al. |
| 4,957,115 A | 9/1990 | Selker |
| 4,958,632 A | 9/1990 | Duggan |
| 4,968,400 A | 11/1990 | Shimomura et al. |
| 4,969,468 A | 11/1990 | Byers et al. |
| 4,970,145 A | 11/1990 | Bennetto et al. |
| 4,974,929 A | 12/1990 | Curry |
| 4,979,509 A | 12/1990 | Hakky |
| 4,986,271 A | 1/1991 | Wilkins |
| 4,990,845 A | 2/1991 | Gord |
| 4,991,582 A | 2/1991 | Byers et al. |
| 4,994,068 A | 2/1991 | Hufnagie |
| 4,994,167 A | 2/1991 | Shults et al. |
| 4,995,402 A | 2/1991 | Smith et al. |
| 5,000,180 A | 3/1991 | Kuypers et al. |
| 5,001,054 A | 3/1991 | Wagner |
| 5,002,054 A | 3/1991 | Ash et al. |
| 5,007,427 A | 4/1991 | Suzuki et al. |
| 5,016,172 A | 5/1991 | Dessertine |
| 5,016,201 A | 5/1991 | Bryan et al. |
| 5,019,974 A | 5/1991 | Beckers |
| 5,034,112 A | 7/1991 | Murase et al. |
| 5,034,192 A | 7/1991 | Wrighton et al. |
| 5,035,860 A | 7/1991 | Kleingeld et al. |
| 5,036,860 A | 8/1991 | Leigh et al. |
| 5,036,861 A | 8/1991 | Sembrowich et al. |
| 5,037,527 A | 8/1991 | Hayashi et al. |
| 5,049,487 A | 9/1991 | Phillips et al. |
| 5,050,612 A | 9/1991 | Matsumura |
| 5,051,688 A | 9/1991 | Murase et al. |
| 5,055,171 A | 10/1991 | Peck |
| 5,058,592 A | 10/1991 | Whisler |
| 5,061,941 A | 10/1991 | Lizzi et al. |
| 5,063,081 A | 11/1991 | Cozzette et al. |
| 5,068,536 A | 11/1991 | Rosenthal |
| 5,070,535 A | 12/1991 | Hochmair et al. |
| 5,073,500 A | 12/1991 | Saito et al. |
| 5,077,476 A | 12/1991 | Rosenthal |
| 5,078,854 A | 1/1992 | Burgess et al. |
| 5,082,550 A | 1/1992 | Rishpon et al. |
| 5,082,786 A | 1/1992 | Nakamoto |
| 5,084,828 A | 1/1992 | Kaufman et al. |
| 5,089,112 A | 2/1992 | Skotheim et al. |
| 5,094,951 A | 3/1992 | Rosenberg |
| 5,095,904 A | 3/1992 | Seligman et al. |
| 5,096,560 A | 3/1992 | Takai et al. |
| 5,096,836 A | 3/1992 | Macho et al. |
| 5,097,834 A | 3/1992 | Skrabal |
| 5,101,814 A | 4/1992 | Palti |
| 5,106,365 A | 4/1992 | Hernandez |
| 5,108,564 A | 4/1992 | Szuminsky et al. |
| 5,109,850 A | 5/1992 | Blanco et al. |
| 5,111,539 A | 5/1992 | Hiruta et al. |
| 5,111,818 A | 5/1992 | Suzuji et al. |
| 5,112,455 A | 5/1992 | Cozzette et al. |
| 5,114,678 A | 5/1992 | Crawford et al. |
| 5,120,420 A | 6/1992 | Nankai et al. |
| 5,120,421 A | 6/1992 | Glass et al. |
| 5,122,925 A | 6/1992 | Inpyn |
| 5,124,661 A | 6/1992 | Zellin et al. |
| 5,126,034 A | 6/1992 | Carter et al. |
| 5,126,247 A | 6/1992 | Palmer et al. |
| 5,130,009 A | 7/1992 | Marsoner et al. |
| 5,133,856 A | 7/1992 | Yamaguchi et al. |
| 5,134,391 A | 7/1992 | Okada |
| 5,134,615 A | 7/1992 | Freeburg et al. |
| 5,135,003 A | 8/1992 | Souma |
| 5,135,004 A | 8/1992 | Adams et al. |
| 5,139,023 A | 8/1992 | Stanley et al. |
| 5,140,393 A | 8/1992 | Hijikihigawa et al. |
| 5,141,868 A | 8/1992 | Shanks et al. |
| 5,145,381 A | 9/1992 | Volz |
| 5,161,532 A | 11/1992 | Joseph |
| 5,165,407 A | 11/1992 | Wilson et al. |
| 5,168,046 A | 12/1992 | Hamamoto et al. |
| 5,174,291 A | 12/1992 | Schoonen et al. |
| 5,176,644 A | 1/1993 | Srisathapat et al. |
| 5,176,662 A | 1/1993 | Bartholomew et al. |
| 5,182,707 A | 1/1993 | Cooper et al. |
| 5,184,359 A | 2/1993 | Tsukumura et al. |
| 5,185,256 A | 2/1993 | Nankai et al. |
| 5,190,041 A | 3/1993 | Palti |
| 5,192,415 A | 3/1993 | Yoshioka et al. |
| 5,192,416 A | 3/1993 | Wang et al. |
| 5,193,539 A | 3/1993 | Schulman et al. |
| 5,193,540 A | 3/1993 | Schulman et al. |
| 5,197,322 A | 3/1993 | Indravudh |
| 5,198,367 A | 3/1993 | Aizawa et al. |
| 5,200,051 A | 4/1993 | Cozzette et al. |
| 5,202,261 A | 4/1993 | Musho et al. |
| 5,205,920 A | 4/1993 | Oyama et al. |
| 5,206,145 A | 4/1993 | Cattell |
| 5,208,154 A | 5/1993 | Weaver et al. |
| 5,209,229 A | 5/1993 | Gilli |
| 5,215,887 A | 6/1993 | Saito |

(56) References Cited

U.S. PATENT DOCUMENTS

| | | |
|---|---|---|
| 5,216,597 A | 6/1993 | Beckers |
| 5,217,442 A | 6/1993 | Davis |
| 5,217,595 A | 6/1993 | Smith et al. |
| 5,227,042 A | 7/1993 | Zawodzinski et al. |
| 5,229,282 A | 7/1993 | Yoshioka et al. |
| 5,236,143 A | 8/1993 | Dragon |
| 5,237,993 A | 8/1993 | Skrabal |
| 5,245,314 A | 9/1993 | Kah et al. |
| 5,246,867 A | 9/1993 | Lakowicz et al. |
| 5,250,439 A | 10/1993 | Musho et al. |
| 5,251,126 A | 10/1993 | Kahn et al. |
| 5,257,971 A | 11/1993 | Lord et al. |
| 5,257,980 A | 11/1993 | Van Antwerp et al. |
| 5,261,401 A | 11/1993 | Baker et al. |
| 5,262,035 A | 11/1993 | Gregg et al. |
| 5,262,305 A | 11/1993 | Heller et al. |
| 5,264,103 A | 11/1993 | Yoshioka et al. |
| 5,264,104 A | 11/1993 | Gregg et al. |
| 5,264,105 A | 11/1993 | Gregg et al. |
| 5,264,106 A | 11/1993 | McAleer et al. |
| 5,265,888 A | 11/1993 | Yamamoto et al. |
| 5,266,179 A | 11/1993 | Nankai et al. |
| 5,269,212 A | 12/1993 | Peters et al. |
| 5,271,815 A | 12/1993 | Wong |
| 5,272,060 A | 12/1993 | Hamamoto et al. |
| 5,275,159 A | 1/1994 | Griebel |
| 5,278,079 A | 1/1994 | Gubinski et al. |
| 5,279,294 A | 1/1994 | Anderson et al. |
| 5,282,950 A | 2/1994 | Dietze et al. |
| 5,284,156 A | 2/1994 | Schramm et al. |
| 5,285,792 A | 2/1994 | Sjoquist et al. |
| 5,286,362 A | 2/1994 | Hoenes et al. |
| 5,286,364 A | 2/1994 | Yacynych et al. |
| 5,288,636 A | 2/1994 | Pollmann et al. |
| 5,289,497 A | 2/1994 | Jackobson et al. |
| 5,291,887 A | 3/1994 | Stanley et al. |
| 5,293,546 A | 3/1994 | Tadros et al. |
| 5,293,877 A | 3/1994 | O'Hara et al. |
| 5,299,571 A | 4/1994 | Mastrototaro |
| 5,304,468 A | 4/1994 | Phillips et al. |
| 5,307,263 A | 4/1994 | Brown |
| 5,309,919 A | 5/1994 | Snell et al. |
| 5,310,885 A | 5/1994 | Maier et al. |
| 5,320,098 A | 6/1994 | Davidson |
| 5,320,725 A | 6/1994 | Gregg et al. |
| 5,322,063 A | 6/1994 | Allen et al. |
| 5,324,303 A | 6/1994 | Strong et al. |
| 5,324,316 A | 6/1994 | Schulman et al. |
| 5,326,449 A | 7/1994 | Cunningham |
| 5,333,615 A | 8/1994 | Craelius et al. |
| 5,337,258 A | 8/1994 | Dennis |
| 5,337,747 A | 8/1994 | Neftei |
| 5,340,722 A | 8/1994 | Wolfbeis et al. |
| 5,342,408 A | 8/1994 | deCoriolis et al. |
| 5,342,789 A | 8/1994 | Chick et al. |
| 5,352,348 A | 10/1994 | Young et al. |
| 5,352,351 A | 10/1994 | White et al. |
| 5,356,348 A | 10/1994 | Bellio et al. |
| 5,356,786 A | 10/1994 | Heller et al. |
| 5,358,135 A | 10/1994 | Robbins et al. |
| 5,358,514 A | 10/1994 | Schulman et al. |
| 5,360,404 A | 11/1994 | Novacek et al. |
| 5,364,797 A | 11/1994 | Olson et al. |
| 5,366,609 A | 11/1994 | White et al. |
| 5,368,028 A | 11/1994 | Palti |
| 5,370,622 A | 12/1994 | Livingston et al. |
| 5,371,687 A | 12/1994 | Holmes, II et al. |
| 5,371,734 A | 12/1994 | Fischer |
| 5,371,787 A | 12/1994 | Hamilton |
| 5,372,133 A | 12/1994 | Hogen Esch |
| 5,372,427 A | 12/1994 | Padovani et al. |
| 5,376,070 A | 12/1994 | Purvis et al. |
| 5,376,251 A | 12/1994 | Kaneko et al. |
| 5,377,258 A | 12/1994 | Bro |
| 5,378,628 A | 1/1995 | Gratzel et al. |
| 5,379,238 A | 1/1995 | Stark |
| 5,379,764 A | 1/1995 | Barnes et al. |
| 5,380,422 A | 1/1995 | Negishi et al. |
| 5,382,346 A | 1/1995 | Uenoyama et al. |
| 5,387,327 A | 2/1995 | Khan |
| 5,390,671 A | 2/1995 | Lord et al. |
| 5,391,250 A | 2/1995 | Cheney, II et al. |
| 5,393,903 A | 2/1995 | Gratzel et al. |
| 5,395,504 A | 3/1995 | Saurer et al. |
| 5,399,823 A | 3/1995 | McCusker |
| 5,400,782 A | 3/1995 | Beaubiah |
| 5,400,794 A | 3/1995 | Gorman |
| 5,408,999 A | 4/1995 | Singh et al. |
| 5,410,326 A | 4/1995 | Goldstein |
| 5,410,471 A | 4/1995 | Alyfuku et al. |
| 5,410,474 A | 4/1995 | Fox |
| 5,411,647 A | 5/1995 | Johnson et al. |
| 5,413,690 A | 5/1995 | Kost et al. |
| 5,422,246 A | 6/1995 | Koopal et al. |
| 5,425,868 A | 6/1995 | Pedersen |
| 5,429,602 A | 7/1995 | Hauser |
| 5,431,160 A | 7/1995 | Wilkins |
| 5,431,691 A | 7/1995 | Snell et al. |
| 5,431,921 A | 7/1995 | Thombre |
| 5,433,710 A | 7/1995 | Van Antwerp et al. |
| 5,437,973 A | 8/1995 | Vadgama et al. |
| 5,437,999 A | 8/1995 | Dieboid et al. |
| 5,438,271 A | 8/1995 | White et al. |
| 5,438,983 A | 8/1995 | Falcone |
| 5,445,611 A | 8/1995 | Eppstein et al. |
| 5,445,920 A | 8/1995 | Saito |
| 5,456,692 A | 10/1995 | Smith, Jr. et al. |
| 5,456,940 A | 10/1995 | Fundelburk |
| 5,458,140 A | 10/1995 | Eppstein et al. |
| 5,460,618 A | 10/1995 | Harreld |
| 5,462,051 A | 10/1995 | Oka et al. |
| 5,462,525 A | 10/1995 | Srisathapat et al. |
| 5,462,645 A | 10/1995 | Albery et al. |
| 5,466,218 A | 11/1995 | Srisathapat et al. |
| 5,467,778 A | 11/1995 | Catt et al. |
| 5,469,846 A | 11/1995 | Khan |
| 5,472,317 A | 12/1995 | Field et al. |
| 5,476,460 A | 12/1995 | Montalvo |
| 5,477,855 A | 12/1995 | Schindler et al. |
| 5,482,473 A | 1/1996 | Lord et al. |
| 5,484,404 A | 1/1996 | Schulman et al. |
| 5,487,751 A | 1/1996 | Radons et al. |
| 5,491,474 A | 2/1996 | Suni et al. |
| 5,494,562 A | 2/1996 | Maley et al. |
| 5,496,453 A | 3/1996 | Uenoyama et al. |
| 5,497,772 A | 3/1996 | Schulman et al. |
| 5,499,243 A | 3/1996 | Hall |
| 5,501,956 A | 3/1996 | Wada et al. |
| 5,505,709 A | 4/1996 | Funderburk |
| 5,505,713 A | 4/1996 | Van Antwerp et al. |
| 5,507,288 A | 4/1996 | Bocker et al. |
| 5,508,171 A | 4/1996 | Walling et al. |
| 5,509,410 A | 4/1996 | Hill et al. |
| 5,514,103 A | 5/1996 | Srisathapat et al. |
| 5,514,253 A | 5/1996 | Davis et al. |
| 5,514,718 A | 5/1996 | Lewis et al. |
| 5,518,006 A | 5/1996 | Mawhirt et al. |
| 5,520,787 A | 5/1996 | Hanagan et al. |
| 5,522,865 A | 6/1996 | Schulman et al. |
| 5,525,511 A | 6/1996 | D'Costa |
| 5,526,120 A | 6/1996 | Jina et al. |
| 5,527,307 A | 6/1996 | Srisathapat et al. |
| 5,529,676 A | 6/1996 | Maley et al. |
| 5,531,878 A | 7/1996 | Vadgama et al. |
| 5,538,511 A | 7/1996 | Van Antwerp et al. |
| 5,544,196 A | 8/1996 | Tiedmann, Jr. et al. |
| 5,545,152 A | 8/1996 | Funderburk et al. |
| 5,545,191 A | 8/1996 | Mann et al. |
| 5,549,113 A | 8/1996 | Halleck et al. |
| 5,549,115 A | 8/1996 | Morgan et al. |
| 5,552,027 A | 9/1996 | Birkle et al. |
| 5,554,166 A | 9/1996 | Lange et al. |
| 5,556,524 A | 9/1996 | Albers |
| 5,558,638 A | 9/1996 | Evers et al. |

(56) References Cited

U.S. PATENT DOCUMENTS

| | | | |
|---|---|---|---|
| 5,559,514 A * | 9/1996 | Thomson | G01K 1/20 |
| | | | 341/157 |
| 5,560,357 A | 10/1996 | Faupei et al. | |
| 5,562,713 A | 10/1996 | Silvian | |
| 5,565,085 A | 10/1996 | Ikeda et al. | |
| 5,567,302 A | 10/1996 | Song et al. | |
| 5,568,806 A | 10/1996 | Cheney, II et al. | |
| 5,569,186 A | 10/1996 | Lord et al. | |
| 5,569,212 A | 10/1996 | Brown | |
| 5,573,647 A | 11/1996 | Maley et al. | |
| 5,575,895 A | 11/1996 | Ikeda et al. | |
| 5,580,527 A | 12/1996 | Bell et al. | |
| 5,580,794 A | 12/1996 | Allen | |
| 5,581,206 A | 12/1996 | Chevallier et al. | |
| 5,582,184 A | 12/1996 | Erickson et al. | |
| 5,582,697 A | 12/1996 | Ikeda et al. | |
| 5,582,698 A | 12/1996 | Flaherty et al. | |
| 5,584,813 A | 12/1996 | Livingston et al. | |
| 5,586,553 A | 12/1996 | Halili et al. | |
| 5,589,326 A | 12/1996 | Deng et al. | |
| 5,593,852 A | 1/1997 | Heller et al. | |
| 5,594,906 A | 1/1997 | Holmes, II et al. | |
| 5,596,150 A | 1/1997 | Arndy et al. | |
| 5,596,994 A | 1/1997 | Bro | |
| 5,600,301 A | 2/1997 | Robinson, III | |
| 5,601,435 A | 2/1997 | Quy | |
| 5,601,694 A | 2/1997 | Maley et al. | |
| 5,605,152 A | 2/1997 | Slate et al. | |
| 5,609,575 A | 3/1997 | Larson et al. | |
| 5,611,900 A | 3/1997 | Worden et al. | |
| 5,615,135 A | 3/1997 | Waclawsky et al. | |
| 5,615,671 A | 4/1997 | Schoonen et al. | |
| 5,616,222 A | 4/1997 | Maley et al. | |
| 5,617,851 A | 4/1997 | Lipkovker | |
| 5,623,925 A | 4/1997 | Swenson et al. | |
| 5,623,933 A | 4/1997 | Amano et al. | |
| 5,628,309 A | 5/1997 | Brown | |
| 5,628,310 A | 5/1997 | Rao et al. | |
| 5,628,324 A | 5/1997 | Sarbach | |
| 5,628,890 A | 5/1997 | Carter et al. | |
| 5,629,981 A | 5/1997 | Nerlikar | |
| 5,637,095 A | 6/1997 | Nason et al. | |
| 5,640,764 A | 6/1997 | Strojnik | |
| 5,640,954 A | 6/1997 | Pfeiffer et al. | |
| 5,643,212 A | 7/1997 | Coutre et al. | |
| 5,647,853 A | 7/1997 | Feldmann et al. | |
| 5,650,062 A | 7/1997 | Ikeda et al. | |
| 5,651,767 A | 7/1997 | Schulman et al. | |
| 5,651,869 A | 7/1997 | Yoshioka et al. | |
| 5,653,239 A | 8/1997 | Pompei et al. | |
| 5,659,454 A | 8/1997 | Vermesse | |
| 5,660,163 A | 8/1997 | Schulman et al. | |
| 5,665,065 A | 9/1997 | Colman et al. | |
| 5,665,222 A | 9/1997 | Heller et al. | |
| 5,667,983 A | 9/1997 | Abel et al. | |
| 5,670,031 A | 9/1997 | Hintsche et al. | |
| 5,678,571 A | 10/1997 | Brown | |
| 5,679,690 A | 10/1997 | Andre et al. | |
| 5,680,858 A | 10/1997 | Hansen et al. | |
| 5,682,233 A | 10/1997 | Brinda | |
| 5,686,717 A | 11/1997 | Knowles et al. | |
| 5,695,623 A | 12/1997 | Michel et al. | |
| 5,695,949 A | 12/1997 | Galen et al. | |
| 5,701,894 A | 12/1997 | Cherry et al. | |
| 5,704,922 A | 1/1998 | Brown | |
| 5,707,502 A | 1/1998 | McCaffrey et al. | |
| 5,708,247 A | 1/1998 | McAleer et al. | |
| 5,710,630 A | 1/1998 | Essenpreis et al. | |
| 5,711,001 A | 1/1998 | Bussan et al. | |
| 5,711,297 A | 1/1998 | Iliff et al. | |
| 5,711,861 A | 1/1998 | Ward et al. | |
| 5,711,862 A | 1/1998 | Sakoda et al. | |
| 5,711,868 A | 1/1998 | Maley et al. | |
| 5,718,234 A | 2/1998 | Warden et al. | |
| 5,720,733 A | 2/1998 | Brown | |
| 5,720,862 A | 2/1998 | Hamamoto et al. | |
| 5,721,783 A | 2/1998 | Anderson | |
| 5,722,397 A | 3/1998 | Eppstein | |
| 5,726,646 A | 3/1998 | Bane et al. | |
| 5,727,548 A | 3/1998 | Hill et al. | |
| 5,729,225 A | 3/1998 | Ledzius | |
| 5,730,124 A | 3/1998 | Yamauchi | |
| 5,730,654 A | 3/1998 | Brown | |
| 5,733,313 A | 3/1998 | Barreras, Sr. et al. | |
| 5,735,273 A | 4/1998 | Kurnik et al. | |
| 5,735,285 A | 4/1998 | Albert et al. | |
| 5,741,211 A | 4/1998 | Renirie et al. | |
| 5,741,688 A | 4/1998 | Oxenboll et al. | |
| 5,746,217 A | 5/1998 | Erickson et al. | |
| 5,748,103 A | 5/1998 | Flach et al. | |
| 5,750,926 A | 5/1998 | Schulman et al. | |
| 5,758,290 A | 5/1998 | Nealon et al. | |
| 5,769,873 A | 6/1998 | Zadeh | |
| 5,770,028 A | 6/1998 | Maley et al. | |
| 5,771,001 A | 6/1998 | Cobb | |
| 5,771,890 A | 6/1998 | Tamada | |
| 5,772,586 A | 6/1998 | Heinonen et al. | |
| 5,777,060 A | 7/1998 | Van Antwerp | |
| 5,779,665 A | 7/1998 | Mastrototaro et al. | |
| 5,781,024 A | 7/1998 | Blomberg et al. | |
| 5,782,814 A | 7/1998 | Brown et al. | |
| 5,785,681 A | 7/1998 | Indravudh | |
| 5,786,439 A | 7/1998 | Van Antwerp et al. | |
| 5,786,584 A | 7/1998 | Button et al. | |
| 5,788,678 A | 8/1998 | Van Antwerp | |
| 5,791,344 A | 8/1998 | Schulman et al. | |
| 5,792,117 A | 8/1998 | Brown | |
| 5,793,292 A | 8/1998 | Ivey | |
| 5,800,420 A | 9/1998 | Gross et al. | |
| 5,804,048 A | 9/1998 | Wong et al. | |
| 5,807,315 A | 9/1998 | Van Antwerp et al. | |
| 5,807,375 A | 9/1998 | Gross et al. | |
| 5,814,599 A | 9/1998 | Mitragotri et al. | |
| 5,820,551 A | 10/1998 | Hill et al. | |
| 5,820,570 A | 10/1998 | Erickson et al. | |
| 5,820,622 A | 10/1998 | Gross et al. | |
| 5,822,715 A | 10/1998 | Worthington et al. | |
| 5,825,488 A | 10/1998 | Kohl et al. | |
| 5,827,179 A | 10/1998 | Lichter et al. | |
| 5,827,183 A | 10/1998 | Kurnik et al. | |
| 5,827,184 A | 10/1998 | Netherly et al. | |
| 5,828,943 A | 10/1998 | Brown | |
| 5,830,064 A | 11/1998 | Bradish et al. | |
| 5,830,129 A | 11/1998 | Baer et al. | |
| 5,830,132 A | 11/1998 | Robinson | |
| 5,830,341 A | 11/1998 | Gilmartin | |
| 5,832,448 A | 11/1998 | Brown | |
| 5,834,224 A | 11/1998 | Ruger et al. | |
| 5,837,454 A | 11/1998 | Cozzette et al. | |
| 5,837,546 A | 11/1998 | Allen et al. | |
| 5,840,020 A | 11/1998 | Heinonen et al. | |
| 5,842,983 A | 12/1998 | Abel et al. | |
| 5,843,140 A | 12/1998 | Strojnik | |
| 5,846,702 A | 12/1998 | Deng et al. | |
| 5,846,744 A | 12/1998 | Athey et al. | |
| 5,851,197 A | 12/1998 | Marano et al. | |
| 5,854,078 A | 12/1998 | Asher et al. | |
| 5,854,189 A | 12/1998 | Kruse et al. | |
| 5,856,758 A | 1/1999 | Joffe et al. | |
| 5,857,967 A | 1/1999 | Frid et al. | |
| 5,857,983 A | 1/1999 | Douglas et al. | |
| 5,860,917 A | 1/1999 | Comanor et al. | |
| 5,863,400 A | 1/1999 | Drummond et al. | |
| 5,872,713 A | 2/1999 | Douglas et al. | |
| 5,876,484 A | 3/1999 | Raskin et al. | |
| 5,879,163 A | 3/1999 | Brown et al. | |
| 5,879,311 A | 3/1999 | Duchon et al. | |
| 5,880,829 A | 3/1999 | Kauhaniemi et al. | |
| 5,882,494 A | 3/1999 | Van Antwerp | |
| 5,885,211 A | 3/1999 | Eppstein et al. | |
| 5,887,133 A | 3/1999 | Brown et al. | |
| 5,897,493 A | 4/1999 | Brown | |
| 5,898,025 A | 4/1999 | Burg et al. | |
| 5,899,855 A | 5/1999 | Brown | |

(56) References Cited

U.S. PATENT DOCUMENTS

| | | |
|---|---|---|
| 5,913,310 A | 6/1999 | Brown |
| 5,917,346 A | 6/1999 | Gord |
| 5,918,603 A | 7/1999 | Brown |
| 5,919,141 A | 7/1999 | Money et al. |
| 5,925,021 A | 7/1999 | Castellano et al. |
| 5,931,791 A | 8/1999 | Saltzstein et al. |
| 5,933,136 A | 8/1999 | Brown |
| 5,935,099 A | 8/1999 | Petterson |
| 5,935,224 A | 8/1999 | Svancarek et al. |
| 5,939,609 A | 8/1999 | Knapp et al. |
| 5,940,801 A | 8/1999 | Brown |
| 5,942,979 A | 8/1999 | Luppino |
| 5,945,345 A | 8/1999 | Blatt et al. |
| 5,947,921 A | 9/1999 | Johnson et al. |
| 5,948,512 A | 9/1999 | Kubota et al. |
| 5,950,632 A | 9/1999 | Reber et al. |
| 5,951,300 A | 9/1999 | Brown |
| 5,951,492 A | 9/1999 | Douglas et al. |
| 5,951,521 A | 9/1999 | Mastrototaro et al. |
| 5,951,836 A | 9/1999 | McAleer et al. |
| 5,954,643 A | 9/1999 | Van Antwerp |
| 5,954,685 A | 9/1999 | Tierny |
| 5,954,700 A | 9/1999 | Kovelman |
| 5,956,501 A | 9/1999 | Brown |
| 5,957,854 A | 9/1999 | Besson et al. |
| 5,957,890 A | 9/1999 | Mann et al. |
| 5,957,958 A | 9/1999 | Schulman et al. |
| 5,960,403 A | 9/1999 | Brown |
| 5,961,451 A | 10/1999 | Reber et al. |
| 5,964,993 A | 10/1999 | Blubaugh, Jr. et al. |
| 5,965,380 A | 10/1999 | Heller et al. |
| 5,968,839 A | 10/1999 | Blatt et al. |
| 5,971,922 A | 10/1999 | Arita et al. |
| 5,971,941 A | 10/1999 | Simons et al. |
| 5,974,124 A | 10/1999 | Schlueter, Jr. et al. |
| 5,977,476 A | 11/1999 | Guha et al. |
| 5,981,294 A | 11/1999 | Blatt et al. |
| 5,989,409 A | 11/1999 | Kurnik et al. |
| 5,994,476 A | 11/1999 | Shin et al. |
| 5,995,860 A | 11/1999 | Sun et al. |
| 5,997,476 A | 12/1999 | Brown |
| 5,999,848 A | 12/1999 | Gord et al. |
| 5,999,849 A | 12/1999 | Gord et al. |
| 6,001,067 A | 12/1999 | Shults et al. |
| 6,002,954 A | 12/1999 | Van Antwerp et al. |
| 6,002,961 A | 12/1999 | Mitragotri et al. |
| 6,004,441 A | 12/1999 | Fujiwara et al. |
| 6,011,984 A | 1/2000 | Van Antwerp et al. |
| 6,014,577 A | 1/2000 | Henning et al. |
| 6,018,678 A | 1/2000 | Mitragotri et al. |
| 6,023,629 A | 2/2000 | Tamada |
| 6,024,699 A | 2/2000 | Surwit et al. |
| 6,026,320 A | 2/2000 | Carlson et al. |
| 6,027,459 A | 2/2000 | Shain et al. |
| 6,027,692 A | 2/2000 | Galen et al. |
| 6,028,413 A | 2/2000 | Brockmann |
| 6,032,059 A | 2/2000 | Henning et al. |
| 6,032,199 A | 2/2000 | Lim et al. |
| 6,033,866 A | 3/2000 | Guo et al. |
| 6,035,237 A | 3/2000 | Schulman et al. |
| 6,040,194 A | 3/2000 | Chick et al. |
| 6,041,253 A | 3/2000 | Kost et al. |
| 6,043,437 A | 3/2000 | Schulman et al. |
| 6,049,727 A | 4/2000 | Crothall |
| 6,052,565 A | 4/2000 | Ishikura et al. |
| 6,055,316 A | 4/2000 | Perlman et al. |
| 6,056,718 A | 5/2000 | Funderburk et al. |
| 6,063,459 A | 5/2000 | Velte |
| 6,066,243 A | 5/2000 | Anderson et al. |
| 6,066,448 A | 5/2000 | Wohlstadter et al. |
| 6,067,474 A | 5/2000 | Schulman et al. |
| 6,068,615 A | 5/2000 | Brown et al. |
| 6,071,249 A | 6/2000 | Cunningham et al. |
| 6,071,251 A | 6/2000 | Cunningham et al. |
| 6,071,294 A | 6/2000 | Simons et al. |
| 6,071,391 A | 6/2000 | Gotoh et al. |
| 6,073,031 A | 6/2000 | Helstab et al. |
| 6,081,736 A | 6/2000 | Colvin et al. |
| 6,083,710 A | 7/2000 | Heller et al. |
| 6,084,523 A | 7/2000 | Gelnovatch et al. |
| 6,088,608 A | 7/2000 | Schulman et al. |
| 6,091,975 A | 7/2000 | Daddona et al. |
| 6,091,976 A | 7/2000 | Pfeiffer et al. |
| 6,093,156 A | 7/2000 | Cunningham et al. |
| 6,093,167 A | 7/2000 | Houben et al. |
| 6,093,172 A | 7/2000 | Funderburk et al. |
| 6,096,364 A | 8/2000 | Bok et al. |
| 6,097,480 A | 8/2000 | Kaplan |
| 6,097,831 A | 8/2000 | Wieck et al. |
| 6,099,484 A | 8/2000 | Douglas et al. |
| 6,101,478 A | 8/2000 | Brown |
| 6,103,033 A | 8/2000 | Say et al. |
| 6,106,780 A | 8/2000 | Douglas et al. |
| 6,110,148 A | 8/2000 | Brown et al. |
| 6,110,152 A | 8/2000 | Kovelman |
| 6,113,578 A | 9/2000 | Brown |
| 6,117,290 A | 9/2000 | Say et al. |
| 6,119,028 A | 9/2000 | Schulman et al. |
| 6,120,676 A | 9/2000 | Heller et al. |
| 6,121,009 A | 9/2000 | Heller et al. |
| 6,121,611 A | 9/2000 | Lindsay et al. |
| 6,122,351 A | 9/2000 | Schlueter, Jr. et al. |
| 6,125,978 A | 10/2000 | Ando et al. |
| 6,134,461 A | 10/2000 | Say et al. |
| 6,134,504 A | 10/2000 | Douglas et al. |
| 6,139,718 A | 10/2000 | Kurnik et al. |
| 6,141,573 A | 10/2000 | Kurnik et al. |
| 6,142,939 A | 11/2000 | Eppstein et al. |
| 6,143,164 A | 11/2000 | Heller et al. |
| 6,144,837 A | 11/2000 | Quy |
| 6,144,869 A | 11/2000 | Berner et al. |
| 6,144,922 A | 11/2000 | Douglas et al. |
| 6,148,094 A | 11/2000 | Kinsella |
| 6,150,128 A | 11/2000 | Uretsky |
| 6,151,517 A | 11/2000 | Honigs et al. |
| 6,151,586 A | 11/2000 | Brown |
| 6,153,062 A | 11/2000 | Saito et al. |
| 6,153,069 A | 11/2000 | Pottgen et al. |
| 6,159,147 A | 12/2000 | Lichter et al. |
| 6,161,095 A | 12/2000 | Brown |
| 6,162,611 A | 12/2000 | Heller et al. |
| 6,162,639 A | 12/2000 | Douglas |
| 6,164,284 A | 12/2000 | Schulman et al. |
| 6,167,362 A | 12/2000 | Brown et al. |
| 6,168,563 B1 | 1/2001 | Brown |
| 6,168,957 B1 | 1/2001 | Matzinger et al. |
| 6,170,318 B1 | 1/2001 | Lewis |
| 6,175,752 B1 | 1/2001 | Say et al. |
| 6,180,416 B1 | 1/2001 | Kurnik et al. |
| 6,186,145 B1 | 2/2001 | Brown |
| 6,192,891 B1 | 2/2001 | Gravel et al. |
| 6,193,873 B1 | 2/2001 | Ohara et al. |
| 6,196,970 B1 | 3/2001 | Brown |
| 6,198,957 B1 | 3/2001 | Green |
| 6,200,265 B1 | 3/2001 | Walsh et al. |
| 6,201,979 B1 | 3/2001 | Kurnik et al. |
| 6,201,980 B1 | 3/2001 | Darrow et al. |
| 6,203,495 B1 | 3/2001 | Bardy et al. |
| 6,206,841 B1 | 3/2001 | Cunningham et al. |
| 6,207,400 B1 | 3/2001 | Kwon |
| 6,208,894 B1 | 3/2001 | Schulman et al. |
| 6,210,272 B1 | 4/2001 | Brown |
| 6,210,976 B1 | 4/2001 | Sabbadini |
| 6,212,416 B1 | 4/2001 | Ward et al. |
| 6,212,417 B1 | 4/2001 | Ikeda et al. |
| 6,218,809 B1 | 4/2001 | Downs et al. |
| 6,219,565 B1 | 4/2001 | Cupp et al. |
| 6,219,574 B1 | 4/2001 | Cormier et al. |
| 6,224,745 B1 | 5/2001 | Baltruschat |
| 6,232,130 B1 | 5/2001 | Wolf |
| 6,232,370 B1 | 5/2001 | Kubota et al. |
| 6,233,471 B1 | 5/2001 | Berner et al. |
| 6,233,539 B1 | 5/2001 | Brown |
| 6,237,394 B1 | 5/2001 | Harris et al. |

(56) References Cited

U.S. PATENT DOCUMENTS

| | | |
|---|---|---|
| 6,239,925 B1 | 5/2001 | Ardrey et al. |
| 6,241,862 B1 | 6/2001 | McAleer et al. |
| 6,246,330 B1 | 6/2001 | Nielsen |
| 6,246,992 B1 | 6/2001 | Brown |
| 6,248,065 B1 | 6/2001 | Brown |
| 6,248,067 B1 | 6/2001 | Causey, III et al. |
| 6,248,093 B1 | 6/2001 | Moberg |
| 6,251,260 B1 | 6/2001 | Heller et al. |
| 6,252,032 B1 | 6/2001 | Van Antwerp et al. |
| 6,253,804 B1 | 7/2001 | Safabash |
| 6,254,586 B1 | 7/2001 | Mann et al. |
| 6,256,643 B1 | 7/2001 | Cork et al. |
| 6,259,587 B1 | 7/2001 | Sheldon et al. |
| 6,259,937 B1 | 7/2001 | Schulman et al. |
| 6,260,022 B1 | 7/2001 | Brown |
| 6,266,645 B1 | 7/2001 | Simpson |
| 6,267,724 B1 | 7/2001 | Taylor |
| 6,268,161 B1 | 7/2001 | Han et al. |
| 6,270,445 B1 | 8/2001 | Dean, Jr. et al. |
| 6,270,455 B1 | 8/2001 | Brown |
| 6,272,364 B1 | 8/2001 | Kurnik |
| 6,275,717 B1 | 8/2001 | Gross et al. |
| 6,280,416 B1 | 8/2001 | Van Antwerp et al. |
| 6,280,587 B1 | 8/2001 | Matsumoto |
| 6,281,006 B1 | 8/2001 | Heller et al. |
| 6,283,943 B1 | 9/2001 | Dy et al. |
| 6,284,126 B1 | 9/2001 | Kurnik et al. |
| 6,284,478 B1 | 9/2001 | Heller et al. |
| 6,293,925 B1 | 9/2001 | Safabash et al. |
| 6,294,281 B1 | 9/2001 | Heller |
| 6,295,463 B1 | 9/2001 | Stenzler |
| 6,295,506 B1 | 9/2001 | Heinonen et al. |
| 6,298,254 B2 | 10/2001 | Tamada |
| 6,299,347 B1 | 10/2001 | Pompei |
| 6,299,578 B1 | 10/2001 | Kurnik et al. |
| 6,299,757 B1 | 10/2001 | Feldman et al. |
| 6,301,499 B1 | 10/2001 | Carlson et al. |
| 6,304,766 B1 | 10/2001 | Colvin, Jr. et al. |
| 6,306,104 B1 | 10/2001 | Cunningham et al. |
| 6,307,867 B1 | 10/2001 | Roobol et al. |
| 6,309,351 B1 | 10/2001 | Kurnik et al. |
| 6,309,884 B1 | 10/2001 | Cooper et al. |
| 6,313,749 B1 | 11/2001 | Horne et al. |
| 6,314,317 B1 | 11/2001 | Willis |
| 6,315,721 B2 | 11/2001 | Schulman et al. |
| 6,319,540 B1 | 11/2001 | Van Antwerp et al. |
| 6,326,160 B1 | 12/2001 | Dunn et al. |
| 6,329,161 B1 | 12/2001 | Heller et al. |
| 6,329,929 B1 | 12/2001 | Weijand et al. |
| 6,330,426 B2 | 12/2001 | Brown et al. |
| 6,330,464 B1 | 12/2001 | Colvin, Jr. et al. |
| 6,331,518 B2 | 12/2001 | Hemm et al. |
| 6,334,778 B1 | 1/2002 | Brown |
| 6,336,900 B1 | 1/2002 | Alleckson et al. |
| 6,338,790 B1 | 1/2002 | Feldman et al. |
| 6,340,421 B1 | 1/2002 | Vachon et al. |
| 6,341,232 B1 | 1/2002 | Conn et al. |
| 6,356,776 B1 | 3/2002 | Berner et al. |
| 6,359,270 B1 | 3/2002 | Bridson |
| 6,359,594 B1 | 3/2002 | Junod |
| 6,360,888 B1 | 3/2002 | McIvor et al. |
| 6,366,793 B1 | 4/2002 | Bell et al. |
| 6,366,794 B1 | 4/2002 | Moussy et al. |
| 6,368,141 B1 | 4/2002 | Van Antwerp et al. |
| 6,368,274 B1 | 4/2002 | Van Antwerp et al. |
| 6,370,410 B2 | 4/2002 | Kurnik et al. |
| 6,377,828 B1 | 4/2002 | Chaiken et al. |
| 6,379,301 B1 | 4/2002 | Worthington et al. |
| 6,383,767 B1 | 5/2002 | Polak |
| 6,385,473 B1 | 5/2002 | Haines et al. |
| 6,387,048 B1 | 5/2002 | Schulman et al. |
| 6,391,643 B1 | 5/2002 | Chen et al. |
| 6,393,318 B1 | 5/2002 | Conn et al. |
| 6,398,562 B1 | 6/2002 | Butler et al. |
| 6,400,974 B1 | 6/2002 | Lesho |
| 6,405,066 B1 | 6/2002 | Essenpreis et al. |
| 6,413,393 B1 | 7/2002 | Van Antwerp et al. |
| 6,416,471 B1 | 7/2002 | Kumar et al. |
| 6,418,332 B1 | 7/2002 | Mastrototaro et al. |
| 6,424,847 B1 | 7/2002 | Mastrototaro et al. |
| 6,427,088 B1 | 7/2002 | Bowman, IV et al. |
| 6,434,409 B1 | 8/2002 | Pfeiffer et al. |
| 6,438,414 B1 | 8/2002 | Conn et al. |
| 6,440,068 B1 | 8/2002 | Brown et al. |
| 6,442,637 B1 | 8/2002 | Hawkins et al. |
| 6,442,672 B1 | 8/2002 | Ganapathy |
| 6,443,942 B2 | 9/2002 | Van Antwerp et al. |
| 6,449,255 B1 | 9/2002 | Waclawsky et al. |
| 6,454,710 B1 | 9/2002 | Ballerstadt et al. |
| 6,462,162 B2 | 10/2002 | Van Antwerp et al. |
| 6,464,848 B1 | 10/2002 | Matsumoto |
| 6,466,810 B1 | 10/2002 | Ward et al. |
| 6,468,222 B1 | 10/2002 | Mault et al. |
| 6,471,689 B1 | 10/2002 | Joseph et al. |
| 6,472,122 B1 | 10/2002 | Schulman et al. |
| 6,475,372 B1 | 11/2002 | Ohara et al. |
| 6,475,750 B1 | 11/2002 | Han et al. |
| 6,477,395 B2 | 11/2002 | Schulman et al. |
| 6,478,736 B1 | 11/2002 | Mault |
| 6,480,730 B2 | 11/2002 | Darrow et al. |
| 6,480,744 B2 | 11/2002 | Ferek-Petric |
| 6,482,156 B2 | 11/2002 | Iliff |
| 6,482,158 B2 | 11/2002 | Mault |
| 6,482,604 B2 | 11/2002 | Kwon |
| 6,484,045 B1 | 11/2002 | Holker et al. |
| 6,484,046 B1 | 11/2002 | Say et al. |
| 6,485,138 B1 | 11/2002 | Kubota et al. |
| 6,493,069 B1 | 12/2002 | Nagashimada et al. |
| 6,494,830 B1 | 12/2002 | Wessel |
| 6,496,728 B2 | 12/2002 | Li et al. |
| 6,505,059 B1 | 1/2003 | Kollias et al. |
| 6,505,121 B1 | 1/2003 | Russel |
| 6,512,939 B1 | 1/2003 | Colvin et al. |
| 6,513,532 B2 | 2/2003 | Mault et al. |
| 6,514,718 B2 | 2/2003 | Heller et al. |
| 6,515,593 B1 | 2/2003 | Stark et al. |
| 6,520,326 B2 | 2/2003 | McIvor et al. |
| 6,522,903 B1 | 2/2003 | Berman et al. |
| 6,529,755 B2 | 3/2003 | Kurnik et al. |
| 6,529,772 B2 | 3/2003 | Carlson et al. |
| 6,530,915 B1 | 3/2003 | Eppstein et al. |
| 6,533,733 B1 | 3/2003 | Ericson et al. |
| 6,534,322 B1 | 3/2003 | Sabbadini |
| 6,534,323 B1 | 3/2003 | Sabbadini |
| 6,535,753 B1 | 3/2003 | Raskas |
| 6,537,243 B1 | 3/2003 | Henning et al. |
| 6,540,675 B2 | 4/2003 | Aceti et al. |
| 6,541,266 B2 | 4/2003 | Modzelweskei et al. |
| 6,544,212 B2 | 4/2003 | Galley et al. |
| 6,546,268 B1 | 4/2003 | Ishikawa et al. |
| 6,546,269 B1 | 4/2003 | Kurnik |
| 6,549,796 B2 | 4/2003 | Sohrab |
| 6,551,276 B1 | 4/2003 | Mann et al. |
| 6,551,494 B1 | 4/2003 | Heller et al. |
| 6,553,244 B2 | 4/2003 | Lesho et al. |
| 6,554,798 B1 | 4/2003 | Mann et al. |
| 6,558,320 B1 | 5/2003 | Causey, III et al. |
| 6,558,321 B1 | 5/2003 | Burd et al. |
| 6,558,351 B1 | 5/2003 | Steil et al. |
| 6,560,471 B1 * | 5/2003 | Heller ............... A61B 5/076 600/347 |
| 6,561,978 B1 | 5/2003 | Conn et al. |
| 6,562,001 B2 | 5/2003 | Lebel et al. |
| 6,564,105 B2 | 5/2003 | Starkweather et al. |
| 6,564,807 B1 | 5/2003 | Schulman et al. |
| 6,565,509 B1 * | 5/2003 | Say ............... H01L 23/3107 600/347 |
| 6,571,128 B2 | 5/2003 | Lebel et al. |
| 6,571,200 B1 | 5/2003 | Mault |
| 6,572,545 B2 | 6/2003 | Knobbe et al. |
| 6,576,101 B1 | 6/2003 | Heller et al. |
| 6,576,117 B1 | 6/2003 | Iketaki et al. |
| 6,577,899 B2 | 6/2003 | Lebel et al. |
| 6,579,498 B1 | 6/2003 | Eglise |

(56) References Cited

U.S. PATENT DOCUMENTS

| | | |
|---|---|---|
| 6,579,690 B1 | 6/2003 | Bonnecaze et al. |
| 6,580,364 B1 | 6/2003 | Munch et al. |
| 6,584,335 B1 | 6/2003 | Haar et al. |
| 6,585,644 B2 | 7/2003 | Lebel et al. |
| 6,587,704 B1 | 7/2003 | Fine et al. |
| 6,587,705 B1 | 7/2003 | Kim et al. |
| 6,591,125 B1 | 7/2003 | Buse et al. |
| 6,591,126 B2 | 7/2003 | Roeper et al. |
| 6,594,514 B2 | 7/2003 | Berner et al. |
| 6,595,919 B2 | 7/2003 | Berner et al. |
| 6,595,929 B2 | 7/2003 | Stivoric et al. |
| 6,599,243 B2 | 7/2003 | Woltermann et al. |
| 6,602,678 B2 | 8/2003 | Kwon et al. |
| 6,602,909 B1 | 8/2003 | Jarowski |
| 6,605,200 B1 | 8/2003 | Mao et al. |
| 6,605,201 B1 | 8/2003 | Mao et al. |
| 6,607,509 B2 | 8/2003 | Bobroff et al. |
| 6,608,562 B1 | 8/2003 | Kimura et al. |
| 6,610,012 B2 | 8/2003 | Mault |
| 6,611,206 B2 | 8/2003 | Eshelman et al. |
| 6,612,306 B1 | 9/2003 | Mault |
| 6,615,078 B1 | 9/2003 | Burson et al. |
| 6,616,613 B1 | 9/2003 | Goodman |
| 6,618,603 B2 | 9/2003 | Varalli et al. |
| 6,620,106 B2 | 9/2003 | Mault |
| 6,627,058 B1 | 9/2003 | Chan |
| 6,627,154 B1 | 9/2003 | Goodman et al. |
| 6,629,934 B2 | 10/2003 | Mault et al. |
| 6,633,772 B2 | 10/2003 | Ford et al. |
| 6,635,014 B2 | 10/2003 | Starkweather et al. |
| 6,641,533 B2 | 11/2003 | Causey, III et al. |
| 6,642,015 B2 | 11/2003 | Vachon et al. |
| 6,645,142 B2 | 11/2003 | Braig et al. |
| 6,645,368 B1 | 11/2003 | Beaty et al. |
| 6,648,821 B2 | 11/2003 | Lebel et al. |
| 6,653,091 B1 | 11/2003 | Dunn et al. |
| 6,654,625 B1 | 11/2003 | Say et al. |
| 6,656,114 B1 | 12/2003 | Poulson et al. |
| 6,658,396 B1 | 12/2003 | Tang et al. |
| 6,659,948 B2 | 12/2003 | Lebel et al. |
| 6,668,196 B1 | 12/2003 | Villegas et al. |
| 6,671,554 B2 | 12/2003 | Gibson et al. |
| 6,673,625 B2 | 1/2004 | Satcher, Jr. et al. |
| 6,682,938 B1 | 1/2004 | Satcher, Jr. et al. |
| 6,683,040 B2 | 1/2004 | Bragulla et al. |
| 6,687,522 B2 | 2/2004 | Tamada |
| 6,687,546 B2 | 2/2004 | Lebel et al. |
| 6,689,056 B1 | 2/2004 | Kilcoyne et al. |
| 6,690,276 B1 | 2/2004 | Marino |
| 6,692,446 B2 | 2/2004 | Hoek |
| 6,693,069 B2 | 2/2004 | Korber et al. |
| 6,694,158 B2 | 2/2004 | Polak |
| 6,694,191 B2 | 2/2004 | Starkweather et al. |
| 6,695,860 B1 | 2/2004 | Ward et al. |
| 6,698,269 B2 | 3/2004 | Baber et al. |
| 6,701,270 B1 | 3/2004 | Miller et al. |
| 6,702,857 B2 | 3/2004 | Brauker et al. |
| 6,704,587 B1 | 3/2004 | Kumar et al. |
| 6,708,057 B2 | 3/2004 | Marganroth |
| 6,711,423 B2 | 3/2004 | Colvin, Jr. |
| 6,723,046 B2 | 4/2004 | Lichtenstein et al. |
| 6,728,560 B2 | 4/2004 | Kollias et al. |
| 6,730,025 B1 | 5/2004 | Platt |
| 6,731,976 B2 | 5/2004 | Penn et al. |
| 6,733,446 B2 | 5/2004 | Lebel et al. |
| 6,734,162 B2 | 5/2004 | Van Antwerp et al. |
| 6,735,479 B2 | 5/2004 | Fabian et al. |
| 6,736,777 B2 | 5/2004 | Kim et al. |
| 6,736,797 B1 | 5/2004 | Larsen et al. |
| 6,737,401 B2 | 5/2004 | Kim et al. |
| 6,738,654 B2 | 5/2004 | Sohrab |
| 6,740,075 B2 | 5/2004 | Lebel et al. |
| 6,741,163 B1 | 5/2004 | Roberts |
| 6,741,876 B1 | 5/2004 | Scecina et al. |
| 6,741,877 B1 | 5/2004 | Shults et al. |
| 6,746,582 B2 | 6/2004 | Heller et al. |
| 6,748,445 B1 | 6/2004 | Darcey et al. |
| 6,749,587 B2 | 6/2004 | Flaherty |
| 6,750,311 B1 | 6/2004 | Van Antwerp et al. |
| 6,758,810 B2 | 7/2004 | Lebel et al. |
| 6,766,183 B2 | 7/2004 | Walsh et al. |
| 6,766,201 B2 | 7/2004 | Von Arx et al. |
| 6,768,425 B2 | 7/2004 | Flaherty et al. |
| 6,770,030 B1 | 8/2004 | Schaupp et al. |
| 6,770,729 B2 | 8/2004 | Van Antwerp et al. |
| 6,771,995 B2 | 8/2004 | Kurnik et al. |
| 6,773,563 B2 | 8/2004 | Matsumoto |
| 6,780,156 B2 | 8/2004 | Haueter et al. |
| 6,780,297 B2 | 8/2004 | Matsumoto et al. |
| 6,780,871 B2 | 8/2004 | Glick et al. |
| 6,784,274 B2 | 8/2004 | Van Antwerp et al. |
| 6,790,178 B1 | 9/2004 | Mault et al. |
| 6,794,195 B2 | 9/2004 | Colvin, Jr. |
| 6,800,451 B2 | 10/2004 | Daniloff et al. |
| 6,804,544 B2 | 10/2004 | Van Antwerp et al. |
| 6,809,507 B2 | 10/2004 | Morgan et al. |
| 6,809,653 B1 | 10/2004 | Mann et al. |
| 6,810,290 B2 | 10/2004 | Lebel et al. |
| 6,810,309 B2 | 10/2004 | Sadler et al. |
| 6,811,533 B2 | 11/2004 | Lebel et al. |
| 6,811,534 B2 | 11/2004 | Bowman, IV et al. |
| 6,811,659 B2 | 11/2004 | Vachon |
| 6,812,031 B1 | 11/2004 | Carlsson |
| 6,813,519 B2 | 11/2004 | Lebel et al. |
| 6,816,742 B2 | 11/2004 | Kim et al. |
| 6,835,553 B2 | 12/2004 | Han et al. |
| RE38,681 E | 1/2005 | Kurnik et al. |
| 6,840,912 B2 | 1/2005 | Kloepfer et al. |
| 6,844,023 B2 | 1/2005 | Schulman et al. |
| 6,849,237 B2 | 2/2005 | Housefield et al. |
| 6,850,790 B2 | 2/2005 | Berner et al. |
| 6,850,859 B1 | 2/2005 | Schuh |
| 6,852,104 B2 | 2/2005 | Blomquist |
| 6,852,500 B1 | 2/2005 | Hoss et al. |
| 6,852,694 B2 | 2/2005 | Van Antwerp et al. |
| 6,853,854 B1 | 2/2005 | Proniewicz et al. |
| 6,856,928 B2 | 2/2005 | Harmon |
| 6,858,403 B2 | 2/2005 | Han et al. |
| 6,862,465 B2 | 3/2005 | Shults et al. |
| 6,862,466 B2 | 3/2005 | Ackerman |
| 6,872,200 B2 | 3/2005 | Mann et al. |
| 6,873,268 B2 | 3/2005 | Lebel et al. |
| 6,881,551 B2 | 4/2005 | Heller et al. |
| 6,882,940 B2 | 4/2005 | Potts et al. |
| 6,885,883 B2 | 4/2005 | Parris et al. |
| 6,889,331 B2 | 5/2005 | Soerensen et al. |
| 6,892,085 B2 | 5/2005 | McIvor et al. |
| 6,893,396 B2 | 5/2005 | Schulze et al. |
| 6,895,263 B2 | 5/2005 | Shin et al. |
| 6,895,265 B2 | 5/2005 | Silver |
| 6,899,683 B2 | 5/2005 | Mault et al. |
| 6,899,684 B2 | 5/2005 | Mault et al. |
| 6,902,207 B2 | 6/2005 | Lickliter |
| 6,902,905 B2 | 6/2005 | Burson et al. |
| 6,904,301 B2 | 6/2005 | Raskas |
| 6,907,127 B1 | 6/2005 | Kravitz et al. |
| 6,915,147 B2 | 7/2005 | Lebel et al. |
| 6,918,874 B1 | 7/2005 | Hatch et al. |
| 6,922,578 B2 | 7/2005 | Eppstein et al. |
| RE38,775 E | 8/2005 | Kurnik et al. |
| 6,923,764 B2 | 8/2005 | Aceti et al. |
| 6,923,936 B2 | 8/2005 | Swanson et al. |
| 6,926,670 B2 | 8/2005 | Rich et al. |
| 6,927,246 B2 | 8/2005 | Noronha et al. |
| 6,931,327 B2 | 8/2005 | Goode, Jr. et al. |
| 6,932,894 B2 | 8/2005 | Mao et al. |
| 6,936,006 B2 | 8/2005 | Sabra |
| 6,936,029 B2 | 8/2005 | Mann et al. |
| 6,937,222 B2 | 8/2005 | Numao |
| 6,940,590 B2 | 9/2005 | Colvin, Jr. et al. |
| 6,941,163 B2 | 9/2005 | Ford et al. |
| 6,950,708 B2 | 9/2005 | Bowman IV et al. |
| 6,952,603 B2 | 10/2005 | Gelber et al. |
| 6,954,673 B2 | 10/2005 | Von Arx et al. |

(56) References Cited

U.S. PATENT DOCUMENTS

| | | |
|---|---|---|
| 6,955,650 B2 | 10/2005 | Mault et al. |
| 6,957,102 B2 | 10/2005 | Silver et al. |
| 6,957,107 B2 | 10/2005 | Rogers et al. |
| 6,958,705 B2 | 10/2005 | Lebel et al. |
| 6,968,294 B2 | 11/2005 | Gutta et al. |
| 6,968,375 B1 | 11/2005 | Brown |
| 6,971,274 B2 | 12/2005 | Olin |
| 6,974,437 B2 | 12/2005 | Lebel et al. |
| 6,978,182 B2 | 12/2005 | Mazar et al. |
| 6,979,326 B2 | 12/2005 | Mann et al. |
| 6,983,176 B2 | 1/2006 | Gardner et al. |
| 6,985,870 B2 | 1/2006 | Martucci et al. |
| 6,987,474 B2 | 1/2006 | Freeman et al. |
| 6,990,317 B2 | 1/2006 | Arnold |
| 6,990,366 B2 | 1/2006 | Say et al. |
| 6,991,096 B2 | 1/2006 | Gottlieb et al. |
| 6,997,907 B2 | 2/2006 | Safabash et al. |
| 6,997,920 B2 | 2/2006 | Mann et al. |
| 6,998,247 B2 | 2/2006 | Monfre et al. |
| 6,999,810 B2 | 2/2006 | Berner et al. |
| 7,003,336 B2 | 2/2006 | Holker et al. |
| 7,003,340 B2 | 2/2006 | Say et al. |
| 7,003,341 B2 | 2/2006 | Say et al. |
| 7,004,901 B2 | 2/2006 | Fish |
| 7,005,857 B2 | 2/2006 | Stiene et al. |
| 7,011,630 B2 | 3/2006 | Desai et al. |
| 7,018,366 B2 | 3/2006 | Easter |
| 7,018,568 B2 | 3/2006 | Tierney |
| 7,022,072 B2 | 4/2006 | Fox et al. |
| 7,024,236 B2 | 4/2006 | Ford et al. |
| 7,024,245 B2 | 4/2006 | Lebel et al. |
| 7,025,743 B2 | 4/2006 | Mann et al. |
| 7,027,621 B1 | 4/2006 | Prokoski |
| 7,027,931 B1 | 4/2006 | Jones et al. |
| 7,029,444 B2 | 4/2006 | Shin et al. |
| 7,039,810 B1 | 5/2006 | Nichols |
| 7,041,068 B2 | 5/2006 | Freeman et al. |
| 7,041,468 B2 | 5/2006 | Drucker et al. |
| 7,049,277 B2 | 5/2006 | Bagulla et al. |
| 7,052,251 B2 | 5/2006 | Nason et al. |
| 7,052,472 B1 | 5/2006 | Miller et al. |
| 7,052,483 B2 | 5/2006 | Wojcik |
| 7,056,302 B2 | 6/2006 | Douglas |
| 7,060,030 B2 | 6/2006 | Von Arx et al. |
| 7,068,227 B2 | 6/2006 | Ying |
| 7,074,307 B2 | 7/2006 | Simpson et al. |
| 7,081,195 B2 | 7/2006 | Simpson et al. |
| 7,089,780 B2 * | 8/2006 | Sunshine ............ G01N 33/0073 340/541 |
| 7,098,803 B2 | 8/2006 | Mann et al. |
| 7,108,778 B2 | 9/2006 | Simpson et al. |
| 7,113,821 B1 | 9/2006 | Sun et al. |
| 7,114,502 B2 | 10/2006 | Schulman et al. |
| 7,124,027 B1 | 10/2006 | Ernst et al. |
| 7,125,382 B2 | 10/2006 | Zhou et al. |
| 7,133,710 B2 | 11/2006 | Acosta et al. |
| 7,134,999 B2 | 11/2006 | Brauker et al. |
| 7,136,689 B2 | 11/2006 | Shults et al. |
| 7,150,975 B2 | 12/2006 | Tamada et al. |
| 7,154,398 B2 | 12/2006 | Chen et al. |
| 7,155,112 B2 | 12/2006 | Uno et al. |
| 7,155,290 B2 | 12/2006 | Von Arx et al. |
| 7,163,511 B2 | 1/2007 | Conn et al. |
| 7,167,818 B2 | 1/2007 | Brown |
| 7,171,274 B2 | 1/2007 | Starkweather et al. |
| 7,174,199 B2 | 2/2007 | Berner et al. |
| 7,181,505 B2 | 2/2007 | Haller et al. |
| 7,183,068 B2 | 2/2007 | Burson et al. |
| 7,183,102 B2 | 2/2007 | Monfre et al. |
| 7,189,341 B2 | 3/2007 | Li et al. |
| 7,190,988 B2 | 3/2007 | Say et al. |
| 7,192,450 B2 | 3/2007 | Brauker et al. |
| 7,198,606 B2 | 4/2007 | Boecker et al. |
| 7,220,387 B2 | 5/2007 | Flaherty et al. |
| 7,221,977 B1 | 5/2007 | Weaver et al. |
| 7,222,054 B2 | 5/2007 | Geva |
| 7,226,442 B2 | 6/2007 | Sheppard et al. |
| 7,226,978 B2 | 6/2007 | Tapsak et al. |
| 7,228,162 B2 | 6/2007 | Ward et al. |
| 7,228,163 B2 | 6/2007 | Ackerman |
| 7,233,817 B2 | 6/2007 | Yen |
| 7,241,266 B2 | 7/2007 | Zhou et al. |
| 7,258,665 B2 | 8/2007 | Kohls et al. |
| 7,261,691 B1 | 8/2007 | Asomani |
| 7,267,665 B2 | 9/2007 | Steil et al. |
| 7,276,029 B2 | 10/2007 | Goode, Jr. et al. |
| 7,278,983 B2 | 10/2007 | Ireland et al. |
| 7,286,894 B1 | 10/2007 | Grant et al. |
| 7,291,107 B2 | 11/2007 | Hellwig et al. |
| 7,295,867 B2 | 11/2007 | Berner et al. |
| 7,297,112 B2 | 11/2007 | Zhou et al. |
| 7,299,082 B2 | 11/2007 | Feldman et al. |
| 7,310,544 B2 | 12/2007 | Brister et al. |
| 7,324,012 B2 | 1/2008 | Mann et al. |
| 7,335,294 B2 | 2/2008 | Heller et al. |
| 7,354,420 B2 | 4/2008 | Steil et al. |
| 7,364,592 B2 | 4/2008 | Carr-Brendel et al. |
| 7,366,556 B2 | 4/2008 | Brister et al. |
| 7,379,765 B2 | 5/2008 | Petisce et al. |
| 7,398,183 B2 | 7/2008 | Holland et al. |
| 7,402,153 B2 | 7/2008 | Steil et al. |
| 7,408,132 B2 | 8/2008 | Wambsganss et al. |
| 7,424,318 B2 | 9/2008 | Brister et al. |
| 7,460,898 B2 | 12/2008 | Brister et al. |
| 7,467,003 B2 | 12/2008 | Brister et al. |
| 7,471,972 B2 | 12/2008 | Rhodes et al. |
| 7,479,910 B1 * | 1/2009 | Heinks .................. H03M 3/382 341/172 |
| 7,491,303 B2 | 2/2009 | Sakata et al. |
| 7,494,465 B2 | 2/2009 | Brister et al. |
| 7,497,827 B2 | 3/2009 | Brister et al. |
| 7,506,046 B2 | 3/2009 | Rhodes |
| 7,519,408 B2 | 4/2009 | Rasdal et al. |
| 7,547,281 B2 | 6/2009 | Hayes et al. |
| 7,569,030 B2 | 8/2009 | Lebel et al. |
| 7,632,228 B2 | 12/2009 | Brauker et al. |
| 7,637,868 B2 | 12/2009 | Saint et al. |
| 7,640,048 B2 | 12/2009 | Dobbles et al. |
| 7,651,596 B2 | 1/2010 | Petisce et al. |
| 7,653,425 B2 | 1/2010 | Hayter et al. |
| 7,654,956 B2 | 2/2010 | Brister et al. |
| 7,657,297 B2 | 2/2010 | Simpson et al. |
| 7,699,775 B2 | 4/2010 | Desai et al. |
| 7,701,052 B2 | 4/2010 | Borland et al. |
| 7,711,402 B2 | 5/2010 | Shults et al. |
| 7,713,574 B2 | 5/2010 | Brister et al. |
| 7,715,893 B2 | 5/2010 | Kamath et al. |
| 7,766,829 B2 | 8/2010 | Sloan et al. |
| 7,768,387 B2 | 8/2010 | Fennell et al. |
| 7,775,444 B2 | 8/2010 | DeRocco et al. |
| 7,804,197 B2 | 9/2010 | Iisaka et al. |
| 7,811,231 B2 | 10/2010 | Jin et al. |
| 7,813,809 B2 | 10/2010 | Strother et al. |
| 7,826,382 B2 | 11/2010 | Sicurello et al. |
| 7,833,151 B2 | 11/2010 | Khait et al. |
| 7,889,069 B2 | 2/2011 | Fifolt et al. |
| 7,948,369 B2 | 5/2011 | Fennell et al. |
| 7,978,063 B2 | 7/2011 | Baldus et al. |
| 8,000,918 B2 | 8/2011 | Fjield et al. |
| 8,010,174 B2 | 8/2011 | Goode et al. |
| 8,010,256 B2 | 8/2011 | Oowada |
| 8,123,686 B2 | 2/2012 | Fennell et al. |
| 8,233,456 B1 | 7/2012 | Kopikare et al. |
| 8,260,393 B2 | 9/2012 | Kamath et al. |
| 8,282,549 B2 | 10/2012 | Brauker et al. |
| 8,396,670 B2 | 3/2013 | St-Pierre |
| 8,417,312 B2 | 4/2013 | Kamath et al. |
| 8,461,985 B2 | 6/2013 | Fennell et al. |
| 8,478,389 B1 | 7/2013 | Brockway et al. |
| 8,560,037 B2 | 10/2013 | Goode, Jr. et al. |
| 8,597,188 B2 | 12/2013 | Bernstein et al. |
| 8,622,903 B2 | 1/2014 | Jin et al. |
| 8,638,411 B2 | 1/2014 | Park et al. |
| 8,849,459 B2 | 9/2014 | Ramey et al. |

(56) References Cited

U.S. PATENT DOCUMENTS

| | | |
|---|---|---|
| 8,914,090 B2 | 12/2014 | Jain et al. |
| 8,937,540 B2 | 1/2015 | Fennell |
| 9,241,631 B2 | 1/2016 | Valdes et al. |
| 9,402,584 B2 | 8/2016 | Fennell |
| 9,743,866 B2 | 8/2017 | Fennell et al. |
| 10,827,954 B2 | 11/2020 | Hoss et al. |
| 10,945,647 B2 | 3/2021 | Mazza et al. |
| 10,973,443 B2 | 4/2021 | Funderburk et al. |
| 10,980,461 B2 | 4/2021 | Simpson et al. |
| 11,000,213 B2 | 5/2021 | Kamath et al. |
| 11,000,216 B2 | 5/2021 | Curry et al. |
| 11,020,031 B1 | 6/2021 | Simpson et al. |
| 11,064,917 B2 | 7/2021 | Simpson et al. |
| 11,141,084 B2 | 10/2021 | Funderburk et al. |
| 2001/0011224 A1 | 8/2001 | Brown |
| 2001/0011795 A1 | 8/2001 | Ohtsuka et al. |
| 2001/0016310 A1 | 8/2001 | Brown et al. |
| 2001/0016682 A1 | 8/2001 | Berner et al. |
| 2001/0016683 A1 | 8/2001 | Darrow et al. |
| 2001/0020124 A1 | 9/2001 | Tamada |
| 2001/0029340 A1 | 10/2001 | Mault et al. |
| 2001/0032278 A1 | 10/2001 | Brown et al. |
| 2001/0037060 A1 | 11/2001 | Thompson et al. |
| 2001/0037069 A1 | 11/2001 | Carlson et al. |
| 2001/0037366 A1 | 11/2001 | Webb et al. |
| 2001/0039504 A1 | 11/2001 | Linberg et al. |
| 2001/0041830 A1 | 11/2001 | Varalli et al. |
| 2001/0041831 A1 | 11/2001 | Starkweather et al. |
| 2001/0044581 A1 | 11/2001 | Mault |
| 2001/0044588 A1 | 11/2001 | Mault |
| 2001/0047125 A1 | 11/2001 | Quy |
| 2001/0047127 A1 | 11/2001 | New et al. |
| 2001/0049096 A1 | 12/2001 | Brown |
| 2001/0049470 A1 | 12/2001 | Mault et al. |
| 2002/0002326 A1 | 1/2002 | Causey, III et al. |
| 2002/0002328 A1 | 1/2002 | Tamada |
| 2002/0004640 A1 | 1/2002 | Conn et al. |
| 2002/0010390 A1 | 1/2002 | Guice et al. |
| 2002/0010414 A1 | 1/2002 | Coston et al. |
| 2002/0013522 A1 | 1/2002 | Lay et al. |
| 2002/0013538 A1 | 1/2002 | Teller |
| 2002/0016530 A1 | 2/2002 | Brown |
| 2002/0016719 A1 | 2/2002 | Nemeth et al. |
| 2002/0018013 A1 | 2/2002 | Nakao et al. |
| 2002/0019022 A1 | 2/2002 | Dunn et al. |
| 2002/0019584 A1 | 2/2002 | Schulze et al. |
| 2002/0019586 A1 | 2/2002 | Teller et al. |
| 2002/0019748 A1 | 2/2002 | Brown |
| 2002/0023852 A1 | 2/2002 | McIvor et al. |
| 2002/0026111 A1 | 2/2002 | Ackerman |
| 2002/0026937 A1 | 3/2002 | Mault |
| 2002/0027164 A1 | 3/2002 | Mault et al. |
| 2002/0028995 A1 | 3/2002 | Mault |
| 2002/0040208 A1 | 4/2002 | Flaherty et al. |
| 2002/0042090 A1 | 4/2002 | Heller et al. |
| 2002/0043651 A1 | 4/2002 | Darrow et al. |
| 2002/0045808 A1 | 4/2002 | Ford et al. |
| 2002/0046300 A1 | 4/2002 | Hanko et al. |
| 2002/0047867 A1 | 4/2002 | Mault et al. |
| 2002/0049482 A1 | 4/2002 | Fabian et al. |
| 2002/0053637 A1 | 5/2002 | Conn et al. |
| 2002/0062069 A1 | 5/2002 | Mault |
| 2002/0063060 A1 | 5/2002 | Gascoyne et al. |
| 2002/0065454 A1 | 5/2002 | Lebel et al. |
| 2002/0068858 A1 | 6/2002 | Braig et al. |
| 2002/0072784 A1 | 6/2002 | Sheppard et al. |
| 2002/0072858 A1 | 6/2002 | Cheng |
| 2002/0074162 A1 | 6/2002 | Su et al. |
| 2002/0077765 A1 | 6/2002 | Mault |
| 2002/0077766 A1 | 6/2002 | Mault |
| 2002/0081559 A1 | 6/2002 | Brown et al. |
| 2002/0083461 A1 | 6/2002 | Hutcheson et al. |
| 2002/0084196 A1 | 7/2002 | Liamos et al. |
| 2002/0085719 A1 | 7/2002 | Crosbie |
| 2002/0087056 A1 | 7/2002 | Aceti et al. |
| 2002/0091312 A1 | 7/2002 | Berner et al. |
| 2002/0091796 A1 | 7/2002 | Higginson et al. |
| 2002/0093969 A1 | 7/2002 | Lin et al. |
| 2002/0099854 A1 | 7/2002 | Jorgensen |
| 2002/0103425 A1 | 8/2002 | Mault |
| 2002/0103499 A1 | 8/2002 | Perez et al. |
| 2002/0106709 A1 | 8/2002 | Potts et al. |
| 2002/0107433 A1 | 8/2002 | Mault |
| 2002/0107476 A1 | 8/2002 | Mann et al. |
| 2002/0109600 A1 | 8/2002 | Mault et al. |
| 2002/0109621 A1 | 8/2002 | Khair et al. |
| 2002/0117639 A1 | 8/2002 | Paolini et al. |
| 2002/0118528 A1 | 8/2002 | Su et al. |
| 2002/0119711 A1 | 8/2002 | Van Antwerp et al. |
| 2002/0124017 A1 | 9/2002 | Mault |
| 2002/0126036 A1 | 9/2002 | Flaherty et al. |
| 2002/0128594 A1 | 9/2002 | Das et al. |
| 2002/0130042 A1 | 9/2002 | Moerman et al. |
| 2002/0133378 A1 | 9/2002 | Mault et al. |
| 2002/0147135 A1 | 10/2002 | Schnell |
| 2002/0161286 A1 | 10/2002 | Gelber et al. |
| 2002/0161288 A1 | 10/2002 | Shin et al. |
| 2002/0169394 A1 | 11/2002 | Eppstein et al. |
| 2002/0169635 A1 | 11/2002 | Shillingburg |
| 2002/0173830 A1 | 11/2002 | Starkweather et al. |
| 2002/0177764 A1 | 11/2002 | Sohrab |
| 2002/0185130 A1 | 12/2002 | Wright et al. |
| 2002/0188748 A1 | 12/2002 | Blackwell et al. |
| 2002/0193679 A1 | 12/2002 | Malave et al. |
| 2003/0003524 A1 | 1/2003 | Taniike et al. |
| 2003/0004403 A1 | 1/2003 | Drinan et al. |
| 2003/0009203 A1 | 1/2003 | Lebel et al. |
| 2003/0023182 A1 | 1/2003 | Mault et al. |
| 2003/0023317 A1 | 1/2003 | Brauker et al. |
| 2003/0028089 A1 | 2/2003 | Galley et al. |
| 2003/0028120 A1 | 2/2003 | Mault et al. |
| 2003/0032077 A1 | 2/2003 | Itoh et al. |
| 2003/0032867 A1 | 2/2003 | Crothall et al. |
| 2003/0032868 A1 | 2/2003 | Graskov et al. |
| 2003/0032874 A1 | 2/2003 | Rhodes et al. |
| 2003/0035371 A1 | 2/2003 | Reed et al. |
| 2003/0040683 A1 | 2/2003 | Rule et al. |
| 2003/0042137 A1 | 3/2003 | Mao et al. |
| 2003/0050537 A1 | 3/2003 | Wessel |
| 2003/0050546 A1 | 3/2003 | Desai et al. |
| 2003/0060689 A1 | 3/2003 | Kohls et al. |
| 2003/0060692 A1 | 3/2003 | Ruchti et al. |
| 2003/0060753 A1 | 3/2003 | Starkweather et al. |
| 2003/0065257 A1 | 4/2003 | Mault et al. |
| 2003/0065273 A1 | 4/2003 | Mault et al. |
| 2003/0065274 A1 | 4/2003 | Mault et al. |
| 2003/0065275 A1 | 4/2003 | Mault et al. |
| 2003/0065308 A1 | 4/2003 | Lebel et al. |
| 2003/0076082 A1 | 4/2003 | Morgan et al. |
| 2003/0076792 A1 | 4/2003 | Theimer |
| 2003/0081370 A1 | 5/2003 | Haskell et al. |
| 2003/0100040 A1 | 5/2003 | Bonnecaze et al. |
| 2003/0100821 A1 | 5/2003 | Heller et al. |
| 2003/0105407 A1 | 6/2003 | Pearce et al. |
| 2003/0108976 A1 | 6/2003 | Braig et al. |
| 2003/0114897 A1 | 6/2003 | Von Arx et al. |
| 2003/0119457 A1 | 6/2003 | Standke |
| 2003/0122021 A1 | 7/2003 | McConnell et al. |
| 2003/0125612 A1 | 7/2003 | Fox et al. |
| 2003/0130616 A1 | 7/2003 | Steil et al. |
| 2003/0134347 A1 | 7/2003 | Heller et al. |
| 2003/0135100 A1 | 7/2003 | Kim et al. |
| 2003/0135333 A1 | 7/2003 | Aceti et al. |
| 2003/0144579 A1 | 7/2003 | Buss |
| 2003/0144581 A1 | 7/2003 | Conn et al. |
| 2003/0146841 A1 | 8/2003 | Koenig |
| 2003/0153820 A1 | 8/2003 | Berner et al. |
| 2003/0153821 A1 | 8/2003 | Berner et al. |
| 2003/0158472 A1 | 8/2003 | Sohrab |
| 2003/0158707 A1 | 8/2003 | Doi |
| 2003/0168338 A1 | 9/2003 | Gao et al. |
| 2003/0175806 A1 | 9/2003 | Rule et al. |
| 2003/0175992 A1 | 9/2003 | Toranto et al. |
| 2003/0176183 A1 | 9/2003 | Drucker et al. |

(56) References Cited

U.S. PATENT DOCUMENTS

| | | |
|---|---|---|
| 2003/0176933 A1 | 9/2003 | Lebel et al. |
| 2003/0179705 A1 | 9/2003 | Kojima |
| 2003/0181851 A1 | 9/2003 | Mann et al. |
| 2003/0181852 A1 | 9/2003 | Mann et al. |
| 2003/0187338 A1 | 10/2003 | Say et al. |
| 2003/0187525 A1 | 10/2003 | Mann et al. |
| 2003/0191376 A1 | 10/2003 | Samuels et al. |
| 2003/0191431 A1 | 10/2003 | Mann et al. |
| 2003/0195403 A1 | 10/2003 | Berner et al. |
| 2003/0195462 A1 | 10/2003 | Mann et al. |
| 2003/0199790 A1 | 10/2003 | Boecker et al. |
| 2003/0199791 A1 | 10/2003 | Boecker et al. |
| 2003/0199903 A1 | 10/2003 | Boecker et al. |
| 2003/0203498 A1 | 10/2003 | Neel et al. |
| 2003/0204290 A1 | 10/2003 | Sadler et al. |
| 2003/0208110 A1 | 11/2003 | Mault et al. |
| 2003/0208113 A1 | 11/2003 | Mault et al. |
| 2003/0208114 A1 | 11/2003 | Ackerman |
| 2003/0208133 A1 | 11/2003 | Mault |
| 2003/0208409 A1 | 11/2003 | Mault |
| 2003/0212317 A1 | 11/2003 | Kovatchev et al. |
| 2003/0212364 A1 | 11/2003 | Mann et al. |
| 2003/0212379 A1 | 11/2003 | Bylund et al. |
| 2003/0212579 A1 | 11/2003 | Brown et al. |
| 2003/0216630 A1 | 11/2003 | Jersey-Willuhn et al. |
| 2003/0217966 A1 | 11/2003 | Tapsak et al. |
| 2003/0226695 A1 | 12/2003 | Mault |
| 2003/0229514 A2 | 12/2003 | Brown |
| 2003/0232370 A1 | 12/2003 | Trifiro |
| 2003/0235817 A1 | 12/2003 | Bartkowiak et al. |
| 2004/0010207 A1 | 1/2004 | Flaherty et al. |
| 2004/0011671 A1 | 1/2004 | Shults et al. |
| 2004/0017300 A1 | 1/2004 | Kotzin et al. |
| 2004/0018486 A1 | 1/2004 | Dunn et al. |
| 2004/0022438 A1 | 2/2004 | Hibbard |
| 2004/0030226 A1 | 2/2004 | Quy |
| 2004/0030531 A1 | 2/2004 | Miller et al. |
| 2004/0030581 A1 | 2/2004 | Levin et al. |
| 2004/0034289 A1 | 2/2004 | Teller et al. |
| 2004/0039255 A1 | 2/2004 | Simonsen et al. |
| 2004/0039256 A1 | 2/2004 | Kawatahara et al. |
| 2004/0039298 A1 | 2/2004 | Abreu et al. |
| 2004/0040840 A1 | 3/2004 | Mao et al. |
| 2004/0045879 A1 | 3/2004 | Shults et al. |
| 2004/0054263 A1 | 3/2004 | Moerman et al. |
| 2004/0059201 A1 | 3/2004 | Ginsberg |
| 2004/0063435 A1 | 4/2004 | Sakamoto et al. |
| 2004/0064068 A1 | 4/2004 | DeNuzzio et al. |
| 2004/0069164 A1 | 4/2004 | Nakamura et al. |
| 2004/0072357 A1 | 4/2004 | Stiene et al. |
| 2004/0073095 A1 | 4/2004 | Causey, III et al. |
| 2004/0096959 A1 | 5/2004 | Stiene et al. |
| 2004/0100376 A1 | 5/2004 | Lye et al. |
| 2004/0105411 A1 | 6/2004 | Boatwright et al. |
| 2004/0106858 A1 | 6/2004 | Say et al. |
| 2004/0106859 A1 | 6/2004 | Say et al. |
| 2004/0108226 A1 | 6/2004 | Polychronakos et al. |
| 2004/0116786 A1 | 6/2004 | Iijima et al. |
| 2004/0122353 A1 | 6/2004 | Shahmirian et al. |
| 2004/0122489 A1 | 6/2004 | Mazar et al. |
| 2004/0122530 A1 | 6/2004 | Hansen et al. |
| 2004/0127777 A1 | 7/2004 | Ruchti et al. |
| 2004/0128161 A1 | 7/2004 | Mazar et al. |
| 2004/0133164 A1 | 7/2004 | Funderburk et al. |
| 2004/0133390 A1 | 7/2004 | Osorio et al. |
| 2004/0136361 A1 | 7/2004 | Holloway et al. |
| 2004/0136377 A1 | 7/2004 | Miyazaki et al. |
| 2004/0138588 A1 | 7/2004 | Saikiey et al. |
| 2004/0146909 A1 | 7/2004 | Duong et al. |
| 2004/0147872 A1 | 7/2004 | Thompson |
| 2004/0152622 A1 | 8/2004 | Keith et al. |
| 2004/0152961 A1 | 8/2004 | Carlson et al. |
| 2004/0153585 A1 | 8/2004 | Kawatahara et al. |
| 2004/0162473 A1 | 8/2004 | Sohrab |
| 2004/0164961 A1 | 8/2004 | Bal et al. |
| 2004/0167383 A1 | 8/2004 | Kim et al. |
| 2004/0167464 A1 | 8/2004 | Ireland et al. |
| 2004/0167801 A1* | 8/2004 | Say ..................... A61B 5/7445 705/2 |
| 2004/0171921 A1 | 9/2004 | Say et al. |
| 2004/0172284 A1 | 9/2004 | Sullivan et al. |
| 2004/0176672 A1 | 9/2004 | Silver et al. |
| 2004/0176913 A1 | 9/2004 | Kawatahara et al. |
| 2004/0186362 A1 | 9/2004 | Brauker et al. |
| 2004/0186365 A1 | 9/2004 | Jin et al. |
| 2004/0193020 A1 | 9/2004 | Chiba et al. |
| 2004/0193025 A1 | 9/2004 | Steil et al. |
| 2004/0193090 A1 | 9/2004 | Lebel et al. |
| 2004/0197846 A1 | 10/2004 | Hockersmith et al. |
| 2004/0199056 A1 | 10/2004 | Husemann et al. |
| 2004/0199059 A1 | 10/2004 | Brauker et al. |
| 2004/0202576 A1 | 10/2004 | Aceti et al. |
| 2004/0204055 A1 | 10/2004 | Nousiainen |
| 2004/0204687 A1 | 10/2004 | Mogensen et al. |
| 2004/0204868 A1 | 10/2004 | Maynard et al. |
| 2004/0206916 A1 | 10/2004 | Colvin, Jr. et al. |
| 2004/0208780 A1 | 10/2004 | Faries, Jr. et al. |
| 2004/0212536 A1 | 10/2004 | Mori et al. |
| 2004/0221057 A1 | 11/2004 | Darcey et al. |
| 2004/0225199 A1 | 11/2004 | Evanyk et al. |
| 2004/0225338 A1 | 11/2004 | Lebel et al. |
| 2004/0235446 A1 | 11/2004 | Flaherty et al. |
| 2004/0236200 A1 | 11/2004 | Say et al. |
| 2004/0244151 A1 | 12/2004 | Sakata et al. |
| 2004/0248204 A1 | 12/2004 | Moerman |
| 2004/0249250 A1 | 12/2004 | McGee et al. |
| 2004/0249253 A1 | 12/2004 | Racchini et al. |
| 2004/0249254 A1 | 12/2004 | Racchini et al. |
| 2004/0249999 A1 | 12/2004 | Connolly et al. |
| 2004/0253736 A1 | 12/2004 | Stout et al. |
| 2004/0254429 A1 | 12/2004 | Yang |
| 2004/0254433 A1 | 12/2004 | Bandis et al. |
| 2004/0254434 A1 | 12/2004 | Goodnow et al. |
| 2004/0260363 A1 | 12/2004 | Arx et al. |
| 2004/0260478 A1 | 12/2004 | Schwamm |
| 2004/0263354 A1 | 12/2004 | Mann et al. |
| 2004/0267300 A1 | 12/2004 | Mace |
| 2005/0001024 A1 | 1/2005 | Kusaka et al. |
| 2005/0003470 A1 | 1/2005 | Nelson et al. |
| 2005/0004439 A1 | 1/2005 | Shin et al. |
| 2005/0004494 A1 | 1/2005 | Perez et al. |
| 2005/0010087 A1 | 1/2005 | Banet et al. |
| 2005/0010269 A1 | 1/2005 | Lebel et al. |
| 2005/0016276 A1 | 1/2005 | Guan et al. |
| 2005/0017864 A1 | 1/2005 | Tsoukalis |
| 2005/0027177 A1 | 2/2005 | Shin et al. |
| 2005/0027179 A1 | 2/2005 | Berner et al. |
| 2005/0027180 A1 | 2/2005 | Goode, Jr. et al. |
| 2005/0027181 A1 | 2/2005 | Goode, Jr. et al. |
| 2005/0027462 A1 | 2/2005 | Goode, Jr. et al. |
| 2005/0027463 A1 | 2/2005 | Goode, Jr. et al. |
| 2005/0031689 A1 | 2/2005 | Shults et al. |
| 2005/0033132 A1 | 2/2005 | Shults et al. |
| 2005/0038332 A1 | 2/2005 | Saidara et al. |
| 2005/0038680 A1 | 2/2005 | McMahon |
| 2005/0043598 A1 | 2/2005 | Goode, Jr. et al. |
| 2005/0043894 A1 | 2/2005 | Fernandez |
| 2005/0049179 A1 | 3/2005 | Davidson et al. |
| 2005/0049473 A1 | 3/2005 | Desai et al. |
| 2005/0054909 A1 | 3/2005 | Petisce et al. |
| 2005/0059372 A1 | 3/2005 | Arayashiki et al. |
| 2005/0059871 A1 | 3/2005 | Gough et al. |
| 2005/0065464 A1 | 3/2005 | Talbot et al. |
| 2005/0069892 A1 | 3/2005 | Iyengar et al. |
| 2005/0070777 A1 | 3/2005 | Cho et al. |
| 2005/0090607 A1 | 4/2005 | Tapsak et al. |
| 2005/0096511 A1 | 5/2005 | Fox et al. |
| 2005/0096512 A1 | 5/2005 | Fox et al. |
| 2005/0096516 A1 | 5/2005 | Soykan et al. |
| 2005/0112169 A1 | 5/2005 | Brauker et al. |
| 2005/0112544 A1* | 5/2005 | Xu ..................... G01N 27/02 435/287.1 |
| 2005/0113648 A1 | 5/2005 | Yang et al. |
| 2005/0113653 A1 | 5/2005 | Fox et al. |

(56) References Cited

U.S. PATENT DOCUMENTS

| | | |
|---|---|---|
| 2005/0113657 A1 | 5/2005 | Alarcon et al. |
| 2005/0113658 A1 | 5/2005 | Jacobson et al. |
| 2005/0113886 A1 | 5/2005 | Fischell et al. |
| 2005/0114068 A1 | 5/2005 | Chey et al. |
| 2005/0116683 A1 | 6/2005 | Cheng et al. |
| 2005/0118726 A1 | 6/2005 | Schultz et al. |
| 2005/0121322 A1 | 6/2005 | Say et al. |
| 2005/0124873 A1 | 6/2005 | Shults et al. |
| 2005/0131346 A1 | 6/2005 | Douglas |
| 2005/0137471 A1 | 6/2005 | Haar et al. |
| 2005/0137530 A1 | 6/2005 | Campbell et al. |
| 2005/0143635 A1 | 6/2005 | Kamath et al. |
| 2005/0143636 A1 | 6/2005 | Zhang et al. |
| 2005/0148003 A1 | 7/2005 | Kieth et al. |
| 2005/0151976 A1 | 7/2005 | Toma |
| 2005/0154271 A1 | 7/2005 | Rasdal et al. |
| 2005/0161346 A1 | 7/2005 | Simpson et al. |
| 2005/0171503 A1 | 8/2005 | Van Den Berghe et al. |
| 2005/0171513 A1 | 8/2005 | Mann et al. |
| 2005/0173245 A1 | 8/2005 | Feldman et al. |
| 2005/0176136 A1 | 8/2005 | Burd et al. |
| 2005/0177036 A1 | 8/2005 | Shults et al. |
| 2005/0177398 A1 | 8/2005 | Watanabe et al. |
| 2005/0181012 A1 | 8/2005 | Saint et al. |
| 2005/0182306 A1 | 8/2005 | Sloan |
| 2005/0182358 A1 | 8/2005 | Veit et al. |
| 2005/0182451 A1 | 8/2005 | Griffin et al. |
| 2005/0187720 A1 | 8/2005 | Goode, Jr. et al. |
| 2005/0192494 A1 | 9/2005 | Ginsberg |
| 2005/0192557 A1 | 9/2005 | Brauker et al. |
| 2005/0195930 A1 | 9/2005 | Spital et al. |
| 2005/0199494 A1 | 9/2005 | Say et al. |
| 2005/0203360 A1 | 9/2005 | Brauker et al. |
| 2005/0203707 A1 | 9/2005 | Tsutsui et al. |
| 2005/0204134 A1 | 9/2005 | Von Arx et al. |
| 2005/0214892 A1 | 9/2005 | Kovatchev et al. |
| 2005/0215871 A1 | 9/2005 | Feldman et al. |
| 2005/0215872 A1 | 9/2005 | Berner et al. |
| 2005/0221504 A1 | 10/2005 | Petruno et al. |
| 2005/0236361 A1 | 10/2005 | Ufer et al. |
| 2005/0239154 A1 | 10/2005 | Feldman et al. |
| 2005/0239156 A1 | 10/2005 | Drucker et al. |
| 2005/0241957 A1 | 11/2005 | Mao et al. |
| 2005/0242479 A1 | 11/2005 | Petisce et al. |
| 2005/0245795 A1 | 11/2005 | Goode, Jr. et al. |
| 2005/0245799 A1 | 11/2005 | Brauker et al. |
| 2005/0245839 A1 | 11/2005 | Stivoric et al. |
| 2005/0245904 A1 | 11/2005 | Estes et al. |
| 2005/0251033 A1 | 11/2005 | Scarantino et al. |
| 2005/0251083 A1 | 11/2005 | Carr-Brendel et al. |
| 2005/0259514 A1 | 11/2005 | Iseli et al. |
| 2005/0261660 A1 | 11/2005 | Choi |
| 2005/0267780 A1 | 12/2005 | Ray et al. |
| 2005/0271546 A1 | 12/2005 | Gelber et al. |
| 2005/0271547 A1 | 12/2005 | Gelber et al. |
| 2005/0272640 A1 | 12/2005 | Doyle, III et al. |
| 2005/0272985 A1 | 12/2005 | Kotulla et al. |
| 2005/0277164 A1 | 12/2005 | Drucker et al. |
| 2005/0277912 A1 | 12/2005 | John |
| 2005/0287620 A1 | 12/2005 | Heller et al. |
| 2006/0001538 A1 | 1/2006 | Kraft et al. |
| 2006/0001550 A1 | 1/2006 | Mann et al. |
| 2006/0001551 A1 | 1/2006 | Kraft et al. |
| 2006/0003398 A1 | 1/2006 | Heller et al. |
| 2006/0004270 A1 | 1/2006 | Bedard et al. |
| 2006/0004271 A1 | 1/2006 | Peyser et al. |
| 2006/0007017 A1 | 1/2006 | Mann et al. |
| 2006/0015020 A1 | 1/2006 | Neale et al. |
| 2006/0015024 A1 | 1/2006 | Brister et al. |
| 2006/0016700 A1 | 1/2006 | Brister et al. |
| 2006/0019327 A1 | 1/2006 | Brister et al. |
| 2006/0020186 A1 | 1/2006 | Brister et al. |
| 2006/0020187 A1 | 1/2006 | Brister et al. |
| 2006/0020188 A1 | 1/2006 | Kamath et al. |
| 2006/0020189 A1 | 1/2006 | Brister et al. |
| 2006/0020190 A1 | 1/2006 | Kamath et al. |
| 2006/0020191 A1 | 1/2006 | Brister et al. |
| 2006/0020192 A1 | 1/2006 | Brister et al. |
| 2006/0020300 A1 | 1/2006 | Nghiem et al. |
| 2006/0025663 A1 | 2/2006 | Talbot et al. |
| 2006/0029177 A1 | 2/2006 | Cranford, Jr. et al. |
| 2006/0031094 A1 | 2/2006 | Cohen et al. |
| 2006/0036139 A1 | 2/2006 | Brister et al. |
| 2006/0036140 A1 | 2/2006 | Brister et al. |
| 2006/0036141 A1 | 2/2006 | Kamath et al. |
| 2006/0036142 A1 | 2/2006 | Brister et al. |
| 2006/0036143 A1 | 2/2006 | Brister et al. |
| 2006/0036144 A1 | 2/2006 | Brister et al. |
| 2006/0036145 A1 | 2/2006 | Brister et al. |
| 2006/0036187 A1 | 2/2006 | Vos et al. |
| 2006/0040402 A1 | 2/2006 | Brauker et al. |
| 2006/0052679 A1 | 3/2006 | Kotulla et al. |
| 2006/0058588 A1 | 3/2006 | Zdeblick |
| 2006/0058602 A1 | 3/2006 | Kwiatkowski et al. |
| 2006/0063218 A1 | 3/2006 | Bartkowiak et al. |
| 2006/0074564 A1 | 4/2006 | Bartowiak et al. |
| 2006/0094944 A1 | 5/2006 | Chuang |
| 2006/0094945 A1 | 5/2006 | Barman et al. |
| 2006/0129733 A1 | 6/2006 | Solbelman |
| 2006/0142651 A1 | 6/2006 | Brister et al. |
| 2006/0154642 A1 | 7/2006 | Scannell |
| 2006/0155180 A1 | 7/2006 | Brister et al. |
| 2006/0166629 A1 | 7/2006 | Reggiardo |
| 2006/0173260 A1 | 8/2006 | Gaoni et al. |
| 2006/0173406 A1 | 8/2006 | Hayes et al. |
| 2006/0173444 A1 | 8/2006 | Choy et al. |
| 2006/0183984 A1 | 8/2006 | Dobbles et al. |
| 2006/0183985 A1 | 8/2006 | Brister et al. |
| 2006/0189863 A1* | 8/2006 | Peyser ............... A61B 5/742 128/903 |
| 2006/0193375 A1 | 8/2006 | Lee et al. |
| 2006/0195029 A1 | 8/2006 | Shults et al. |
| 2006/0198426 A1 | 9/2006 | Partyka |
| 2006/0200112 A1 | 9/2006 | Paul |
| 2006/0202859 A1* | 9/2006 | Mastrototaro ...... A61B 5/14532 340/870.07 |
| 2006/0222566 A1 | 10/2006 | Brauker et al. |
| 2006/0224109 A1 | 10/2006 | Steil et al. |
| 2006/0224141 A1 | 10/2006 | Rush et al. |
| 2006/0226985 A1 | 10/2006 | Goodnow et al. |
| 2006/0229512 A1 | 10/2006 | Petisce et al. |
| 2006/0247508 A1 | 11/2006 | Fennell |
| 2006/0247985 A1 | 11/2006 | Liamos et al. |
| 2006/0253296 A1 | 11/2006 | Liisberg et al. |
| 2006/0258918 A1 | 11/2006 | Burd et al. |
| 2006/0258929 A1 | 11/2006 | Goode, Jr. et al. |
| 2006/0258959 A1 | 11/2006 | Sode |
| 2006/0263763 A1 | 11/2006 | Simpson et al. |
| 2006/0264785 A1 | 11/2006 | Dring et al. |
| 2006/0264888 A1 | 11/2006 | Moberg et al. |
| 2006/0270922 A1 | 11/2006 | Brauker et al. |
| 2006/0272652 A1 | 12/2006 | Stocker et al. |
| 2006/0276714 A1 | 12/2006 | Holt et al. |
| 2006/0281985 A1 | 12/2006 | Ward et al. |
| 2006/0290496 A1 | 12/2006 | Peeters et al. |
| 2006/0293576 A1 | 12/2006 | Van Antwerp et al. |
| 2006/0293607 A1 | 12/2006 | Alt et al. |
| 2007/0007133 A1 | 1/2007 | Mang et al. |
| 2007/0016381 A1 | 1/2007 | Kamath et al. |
| 2007/0017983 A1 | 1/2007 | Frank et al. |
| 2007/0026440 A1 | 2/2007 | Broderick et al. |
| 2007/0027381 A1 | 2/2007 | Stafford |
| 2007/0027507 A1 | 2/2007 | Burdett et al. |
| 2007/0032706 A1 | 2/2007 | Kamath et al. |
| 2007/0033074 A1 | 2/2007 | Nitzan et al. |
| 2007/0038044 A1 | 2/2007 | Dobbles et al. |
| 2007/0053341 A1 | 3/2007 | Lizzi |
| 2007/0060814 A1 | 3/2007 | Stafford |
| 2007/0060869 A1 | 3/2007 | Tolle et al. |
| 2007/0066873 A1 | 3/2007 | Kamath et al. |
| 2007/0066877 A1 | 3/2007 | Arnold et al. |
| 2007/0071681 A1 | 3/2007 | Gadkar et al. |
| 2007/0073129 A1 | 3/2007 | Shah et al. |
| 2007/0078320 A1 | 4/2007 | Stafford |

(56) References Cited

U.S. PATENT DOCUMENTS

| | | |
|---|---|---|
| 2007/0078321 A1 | 4/2007 | Mazza et al. |
| 2007/0078322 A1 | 4/2007 | Stafford |
| 2007/0078323 A1 | 4/2007 | Reggiardo et al. |
| 2007/0090511 A1 | 4/2007 | Borland et al. |
| 2007/0093786 A1 | 4/2007 | Goldsmith et al. |
| 2007/0100222 A1 | 5/2007 | Mastrototaro et al. |
| 2007/0106133 A1 | 5/2007 | Satchwell et al. |
| 2007/0106135 A1 | 5/2007 | Sloan et al. |
| 2007/0118030 A1 | 5/2007 | Bruce et al. |
| 2007/0124002 A1 | 5/2007 | Estes et al. |
| 2007/0135697 A1 | 6/2007 | Reggiardo |
| 2007/0149873 A1 | 6/2007 | Say et al. |
| 2007/0149874 A1 | 6/2007 | Say et al. |
| 2007/0149875 A1 | 6/2007 | Ouyang et al. |
| 2007/0151869 A1 | 7/2007 | Heller et al. |
| 2007/0153705 A1 | 7/2007 | Rosar et al. |
| 2007/0156094 A1 | 7/2007 | Safabash et al. |
| 2007/0161879 A1 | 7/2007 | Say et al. |
| 2007/0161880 A1 | 7/2007 | Say et al. |
| 2007/0163880 A1 | 7/2007 | Woo et al. |
| 2007/0168224 A1 | 7/2007 | Letzt et al. |
| 2007/0170893 A1 | 7/2007 | Kao et al. |
| 2007/0173706 A1 | 7/2007 | Neinast et al. |
| 2007/0173712 A1 | 7/2007 | Shah et al. |
| 2007/0173761 A1 | 7/2007 | Kanderian et al. |
| 2007/0179349 A1 | 8/2007 | Hoyme et al. |
| 2007/0179352 A1 | 8/2007 | Randlov et al. |
| 2007/0179370 A1 | 8/2007 | Say et al. |
| 2007/0179372 A1 | 8/2007 | Say et al. |
| 2007/0191699 A1 | 8/2007 | Say et al. |
| 2007/0191700 A1 | 8/2007 | Say et al. |
| 2007/0191701 A1 | 8/2007 | Feldman et al. |
| 2007/0191702 A1 | 8/2007 | Yodfat et al. |
| 2007/0203407 A1 | 8/2007 | Hoss et al. |
| 2007/0203408 A1 | 8/2007 | Say et al. |
| 2007/0203410 A1 | 8/2007 | Say et al. |
| 2007/0203411 A1 | 8/2007 | Say et al. |
| 2007/0203966 A1 | 8/2007 | Brauker et al. |
| 2007/0208245 A1 | 9/2007 | Brauker et al. |
| 2007/0208247 A1 | 9/2007 | Say et al. |
| 2007/0213610 A1 | 9/2007 | Say et al. |
| 2007/0213657 A1 | 9/2007 | Jennewine et al. |
| 2007/0215491 A1 | 9/2007 | Heller et al. |
| 2007/0218097 A1 | 9/2007 | Heller et al. |
| 2007/0219496 A1 | 9/2007 | Kamen et al. |
| 2007/0222609 A1 | 9/2007 | Duron et al. |
| 2007/0232877 A1 | 10/2007 | He |
| 2007/0235331 A1 | 10/2007 | Simpson et al. |
| 2007/0244380 A1 | 10/2007 | Say et al. |
| 2007/0249919 A1 | 10/2007 | Say et al. |
| 2007/0249920 A1 | 10/2007 | Say et al. |
| 2007/0249922 A1 | 10/2007 | Peyser et al. |
| 2007/0255321 A1 | 11/2007 | Gelber et al. |
| 2007/0255348 A1 | 11/2007 | Holtzclaw |
| 2007/0271285 A1 | 11/2007 | Eichhorn et al. |
| 2007/0299617 A1* | 12/2007 | Willis ............ A61B 5/7225 204/403.01 |
| 2008/0004515 A1 | 1/2008 | Jennewine et al. |
| 2008/0004601 A1 | 1/2008 | Jennewine et al. |
| 2008/0009304 A1 | 1/2008 | Fry |
| 2008/0009692 A1 | 1/2008 | Stafford |
| 2008/0012701 A1 | 1/2008 | Kass et al. |
| 2008/0017522 A1 | 1/2008 | Heller et al. |
| 2008/0021436 A1* | 1/2008 | Wolpert ............ A61B 5/4839 600/365 |
| 2008/0021666 A1 | 1/2008 | Goode, Jr. et al. |
| 2008/0021972 A1 | 1/2008 | Huelskamp et al. |
| 2008/0027586 A1 | 1/2008 | Hern et al. |
| 2008/0029391 A1 | 2/2008 | Mao et al. |
| 2008/0033254 A1 | 2/2008 | Kamath et al. |
| 2008/0039702 A1 | 2/2008 | Hayter et al. |
| 2008/0045824 A1 | 2/2008 | Tapsak et al. |
| 2008/0055070 A1 | 3/2008 | Bange et al. |
| 2008/0057484 A1 | 3/2008 | Miyata et al. |
| 2008/0058625 A1 | 3/2008 | McGarraugh et al. |
| 2008/0058626 A1 | 3/2008 | Miyata et al. |
| 2008/0058678 A1 | 3/2008 | Miyata et al. |
| 2008/0060955 A1 | 3/2008 | Goodnow |
| 2008/0062055 A1 | 3/2008 | Cunningham et al. |
| 2008/0064937 A1 | 3/2008 | McGarraugh et al. |
| 2008/0067627 A1 | 3/2008 | Boeck et al. |
| 2008/0071156 A1 | 3/2008 | Brister et al. |
| 2008/0071157 A1 | 3/2008 | McGarraugh et al. |
| 2008/0071158 A1 | 3/2008 | McGarraugh et al. |
| 2008/0076997 A1* | 3/2008 | Peyser ............ H01L 23/49548 600/345 |
| 2008/0081977 A1* | 4/2008 | Hayter ............ A61B 5/1495 600/365 |
| 2008/0083617 A1 | 4/2008 | Simpson et al. |
| 2008/0086042 A1 | 4/2008 | Brister et al. |
| 2008/0086044 A1 | 4/2008 | Brister et al. |
| 2008/0086273 A1 | 4/2008 | Shults et al. |
| 2008/0092638 A1 | 4/2008 | Brenneman et al. |
| 2008/0097289 A1 | 4/2008 | Steil et al. |
| 2008/0108942 A1 | 5/2008 | Brister et al. |
| 2008/0154513 A1 | 6/2008 | Kovatchev et al. |
| 2008/0161666 A1 | 7/2008 | Feldman et al. |
| 2008/0167543 A1 | 7/2008 | Say et al. |
| 2008/0172205 A1 | 7/2008 | Breton et al. |
| 2008/0179187 A1 | 7/2008 | Ouyang et al. |
| 2008/0183060 A1 | 7/2008 | Steil et al. |
| 2008/0183061 A1 | 7/2008 | Goode et al. |
| 2008/0183399 A1 | 7/2008 | Goode et al. |
| 2008/0188731 A1 | 8/2008 | Brister et al. |
| 2008/0188796 A1 | 8/2008 | Steil et al. |
| 2008/0189051 A1 | 8/2008 | Goode et al. |
| 2008/0194934 A1 | 8/2008 | Ray et al. |
| 2008/0194935 A1 | 8/2008 | Brister et al. |
| 2008/0194936 A1 | 8/2008 | Goode et al. |
| 2008/0194937 A1 | 8/2008 | Goode et al. |
| 2008/0194938 A1 | 8/2008 | Brister et al. |
| 2008/0195232 A1 | 8/2008 | Carr-Brendel et al. |
| 2008/0195967 A1 | 8/2008 | Goode et al. |
| 2008/0197024 A1 | 8/2008 | Simpson et al. |
| 2008/0200788 A1 | 8/2008 | Brister et al. |
| 2008/0200789 A1 | 8/2008 | Brister et al. |
| 2008/0200791 A1 | 8/2008 | Simpson et al. |
| 2008/0208025 A1 | 8/2008 | Shults et al. |
| 2008/0208113 A1 | 8/2008 | Damian et al. |
| 2008/0212600 A1 | 9/2008 | Yoo |
| 2008/0214900 A1 | 9/2008 | Fennell et al. |
| 2008/0214915 A1 | 9/2008 | Brister et al. |
| 2008/0214918 A1 | 9/2008 | Brister et al. |
| 2008/0228051 A1 | 9/2008 | Shults et al. |
| 2008/0228054 A1 | 9/2008 | Shults et al. |
| 2008/0234943 A1 | 9/2008 | Ray et al. |
| 2008/0242961 A1* | 10/2008 | Brister ............ A61B 5/0002 600/345 |
| 2008/0254544 A1 | 10/2008 | Modzelewski et al. |
| 2008/0255434 A1 | 10/2008 | Hayter et al. |
| 2008/0255437 A1 | 10/2008 | Hayter |
| 2008/0255808 A1 | 10/2008 | Hayter |
| 2008/0256048 A1 | 10/2008 | Hayter |
| 2008/0262469 A1 | 10/2008 | Brister et al. |
| 2008/0267823 A1 | 10/2008 | Wang et al. |
| 2008/0275313 A1 | 11/2008 | Brister et al. |
| 2008/0278331 A1 | 11/2008 | Hayter et al. |
| 2008/0278332 A1 | 11/2008 | Fennell et al. |
| 2008/0278333 A1 | 11/2008 | Fennell et al. |
| 2008/0281171 A1 | 11/2008 | Fennell et al. |
| 2008/0281179 A1 | 11/2008 | Fennell et al. |
| 2008/0281840 A1 | 11/2008 | Fennell et al. |
| 2008/0287761 A1 | 11/2008 | Hayter |
| 2008/0287762 A1 | 11/2008 | Hayter |
| 2008/0287763 A1 | 11/2008 | Hayter |
| 2008/0287764 A1 | 11/2008 | Rasdal et al. |
| 2008/0287765 A1 | 11/2008 | Rasdal et al. |
| 2008/0287766 A1 | 11/2008 | Rasdal et al. |
| 2008/0288180 A1 | 11/2008 | Hayter |
| 2008/0288204 A1 | 11/2008 | Hayter et al. |
| 2008/0294024 A1 | 11/2008 | Cosentino et al. |
| 2008/0296155 A1 | 12/2008 | Shults et al. |
| 2008/0300919 A1 | 12/2008 | Charlton et al. |
| 2008/0300920 A1 | 12/2008 | Brown et al. |

(56) References Cited

U.S. PATENT DOCUMENTS

| | | |
|---|---|---|
| 2008/0301158 A1 | 12/2008 | Brown et al. |
| 2008/0301436 A1 | 12/2008 | Yao et al. |
| 2008/0301665 A1 | 12/2008 | Charlton et al. |
| 2008/0306368 A1 | 12/2008 | Goode et al. |
| 2008/0306434 A1 | 12/2008 | Dobbles et al. |
| 2008/0306435 A1 | 12/2008 | Kamath et al. |
| 2008/0306444 A1 | 12/2008 | Brister et al. |
| 2008/0312841 A1 | 12/2008 | Hayter |
| 2008/0312842 A1 | 12/2008 | Hayter |
| 2008/0312844 A1 | 12/2008 | Hayter et al. |
| 2008/0312845 A1 | 12/2008 | Hayter et al. |
| 2008/0319295 A1 | 12/2008 | Bernstein et al. |
| 2008/0319296 A1 | 12/2008 | Bernstein et al. |
| 2008/0320587 A1 | 12/2008 | Vauclair et al. |
| 2009/0005665 A1 | 1/2009 | Hayter et al. |
| 2009/0006034 A1 | 1/2009 | Hayter et al. |
| 2009/0012379 A1 | 1/2009 | Goode et al. |
| 2009/0018424 A1 | 1/2009 | Kamath et al. |
| 2009/0030294 A1 | 1/2009 | Petisce et al. |
| 2009/0033482 A1 | 2/2009 | Hayter et al. |
| 2009/0036747 A1 | 2/2009 | Hayter et al. |
| 2009/0036758 A1 | 2/2009 | Brauker et al. |
| 2009/0036760 A1 | 2/2009 | Hayter |
| 2009/0036763 A1 | 2/2009 | Brauker et al. |
| 2009/0040022 A1 | 2/2009 | Finkenzeller |
| 2009/0043181 A1 | 2/2009 | Brauker et al. |
| 2009/0043182 A1 | 2/2009 | Brauker et al. |
| 2009/0043525 A1 | 2/2009 | Brauker et al. |
| 2009/0043541 A1 | 2/2009 | Brauker et al. |
| 2009/0043542 A1 | 2/2009 | Brauker et al. |
| 2009/0045055 A1 | 2/2009 | Rhodes et al. |
| 2009/0048503 A1 | 2/2009 | Dalal et al. |
| 2009/0054747 A1 | 2/2009 | Fennell |
| 2009/0055149 A1 | 2/2009 | Hayter et al. |
| 2009/0062633 A1 | 3/2009 | Brauker et al. |
| 2009/0062635 A1 | 3/2009 | Brauker et al. |
| 2009/0062767 A1 | 3/2009 | VanAntwerp et al. |
| 2009/0063187 A1 | 3/2009 | Johnson et al. |
| 2009/0063402 A1 | 3/2009 | Hayter |
| 2009/0076356 A1 | 3/2009 | Simpson et al. |
| 2009/0076359 A1 | 3/2009 | Peyser et al. |
| 2009/0076360 A1 | 3/2009 | Brister et al. |
| 2009/0076361 A1 | 3/2009 | Kamath et al. |
| 2009/0079606 A1* | 3/2009 | Terry .................. A61N 1/3704 341/143 |
| 2009/0079607 A1* | 3/2009 | Denison ............... A61B 5/316 341/166 |
| 2009/0085873 A1 | 4/2009 | Betts et al. |
| 2009/0093687 A1 | 4/2009 | Telfort et al. |
| 2009/0094680 A1 | 4/2009 | Gupta et al. |
| 2009/0099436 A1 | 4/2009 | Brister et al. |
| 2009/0102678 A1 | 4/2009 | Mazza et al. |
| 2009/0105570 A1 | 4/2009 | Sloan et al. |
| 2009/0105571 A1 | 4/2009 | Fennell et al. |
| 2009/0105636 A1 | 4/2009 | Hayter et al. |
| 2009/0124877 A1 | 5/2009 | Goode, Jr. et al. |
| 2009/0124878 A1 | 5/2009 | Goode et al. |
| 2009/0124879 A1 | 5/2009 | Brister et al. |
| 2009/0124964 A1 | 5/2009 | Leach et al. |
| 2009/0131768 A1 | 5/2009 | Simpson et al. |
| 2009/0131769 A1 | 5/2009 | Leach et al. |
| 2009/0131776 A1 | 5/2009 | Simpson et al. |
| 2009/0131777 A1 | 5/2009 | Simpson et al. |
| 2009/0137886 A1 | 5/2009 | Shariati et al. |
| 2009/0137887 A1 | 5/2009 | Shariati et al. |
| 2009/0143659 A1 | 6/2009 | Li et al. |
| 2009/0143660 A1 | 6/2009 | Brister et al. |
| 2009/0146826 A1 | 6/2009 | Gofman et al. |
| 2009/0149717 A1 | 6/2009 | Brauer et al. |
| 2009/0156919 A1 | 6/2009 | Brister et al. |
| 2009/0156924 A1 | 6/2009 | Shariati et al. |
| 2009/0163789 A1 | 6/2009 | Say et al. |
| 2009/0163790 A1 | 6/2009 | Brister et al. |
| 2009/0163791 A1 | 6/2009 | Brister et al. |
| 2009/0164190 A1 | 6/2009 | Hayter |
| 2009/0164239 A1 | 6/2009 | Hayter et al. |
| 2009/0164251 A1 | 6/2009 | Hayter |
| 2009/0178459 A1 | 7/2009 | Li et al. |
| 2009/0182217 A1 | 7/2009 | Li et al. |
| 2009/0192366 A1 | 7/2009 | Mensinger et al. |
| 2009/0192380 A1 | 7/2009 | Shariati et al. |
| 2009/0192722 A1 | 7/2009 | Shariati et al. |
| 2009/0192724 A1 | 7/2009 | Brauker et al. |
| 2009/0192745 A1 | 7/2009 | Kamath et al. |
| 2009/0192751 A1* | 7/2009 | Kamath ............ A61B 5/0004 73/1.02 |
| 2009/0198118 A1 | 8/2009 | Hayter et al. |
| 2009/0203981 A1 | 8/2009 | Brauker et al. |
| 2009/0204340 A1 | 8/2009 | Feldman et al. |
| 2009/0204341 A1 | 8/2009 | Brauker et al. |
| 2009/0216100 A1 | 8/2009 | Ebner et al. |
| 2009/0216103 A1 | 8/2009 | Brister et al. |
| 2009/0237216 A1 | 9/2009 | Twitchell, Jr. |
| 2009/0240120 A1 | 9/2009 | Mensinger et al. |
| 2009/0240128 A1 | 9/2009 | Mensinger et al. |
| 2009/0240193 A1 | 9/2009 | Mensinger et al. |
| 2009/0242399 A1 | 10/2009 | Kamath et al. |
| 2009/0242425 A1 | 10/2009 | Kamath et al. |
| 2009/0247855 A1 | 10/2009 | Boock et al. |
| 2009/0247856 A1 | 10/2009 | Boock et al. |
| 2009/0247857 A1 | 10/2009 | Harper et al. |
| 2009/0287073 A1 | 11/2009 | Boock et al. |
| 2009/0287074 A1 | 11/2009 | Shults et al. |
| 2009/0296742 A1 | 12/2009 | Sicurello et al. |
| 2009/0298182 A1 | 12/2009 | Schulat et al. |
| 2009/0299155 A1 | 12/2009 | Yang et al. |
| 2009/0299156 A1 | 12/2009 | Simpson et al. |
| 2009/0299162 A1 | 12/2009 | Brauker et al. |
| 2009/0299276 A1 | 12/2009 | Brauker et al. |
| 2009/0318789 A1 | 12/2009 | Fennell et al. |
| 2009/0318792 A1 | 12/2009 | Fennell et al. |
| 2010/0010324 A1 | 1/2010 | Brauker et al. |
| 2010/0010329 A1 | 1/2010 | Taub et al. |
| 2010/0010331 A1 | 1/2010 | Brauker et al. |
| 2010/0010332 A1 | 1/2010 | Brauker et al. |
| 2010/0014626 A1 | 1/2010 | Fennell et al. |
| 2010/0016687 A1 | 1/2010 | Brauker et al. |
| 2010/0016698 A1 | 1/2010 | Rasdal et al. |
| 2010/0022855 A1 | 1/2010 | Brauker et al. |
| 2010/0025238 A1 | 2/2010 | Gottlieb et al. |
| 2010/0030038 A1 | 2/2010 | Brauker et al. |
| 2010/0030053 A1 | 2/2010 | Goode, Jr. et al. |
| 2010/0030484 A1 | 2/2010 | Brauker et al. |
| 2010/0030485 A1 | 2/2010 | Brauker et al. |
| 2010/0036215 A1 | 2/2010 | Goode, Jr. et al. |
| 2010/0036216 A1 | 2/2010 | Goode, Jr. et al. |
| 2010/0036222 A1 | 2/2010 | Goode, Jr. et al. |
| 2010/0036223 A1 | 2/2010 | Goode, Jr. et al. |
| 2010/0036225 A1 | 2/2010 | Goode, Jr. et al. |
| 2010/0041971 A1 | 2/2010 | Goode, Jr. et al. |
| 2010/0045465 A1 | 2/2010 | Brauker et al. |
| 2010/0049024 A1 | 2/2010 | Saint et al. |
| 2010/0198034 A1 | 2/2010 | Thomas et al. |
| 2010/0057040 A1 | 3/2010 | Hayter |
| 2010/0057041 A1 | 3/2010 | Hayter |
| 2010/0057042 A1 | 3/2010 | Hayter |
| 2010/0057044 A1 | 3/2010 | Hayter |
| 2010/0057057 A1 | 3/2010 | Hayter et al. |
| 2010/0063373 A1 | 3/2010 | Kamath et al. |
| 2010/0076283 A1 | 3/2010 | Simpson et al. |
| 2010/0081908 A1 | 4/2010 | Dobbles et al. |
| 2010/0081910 A1 | 4/2010 | Brister et al. |
| 2010/0087724 A1 | 4/2010 | Brauker et al. |
| 2010/0094111 A1 | 4/2010 | Heller et al. |
| 2010/0096259 A1 | 4/2010 | Zhang et al. |
| 2010/0099970 A1 | 4/2010 | Shults et al. |
| 2010/0099971 A1 | 4/2010 | Shults et al. |
| 2010/0105999 A1 | 4/2010 | Dixon et al. |
| 2010/0110931 A1 | 5/2010 | Shim et al. |
| 2010/0119693 A1 | 5/2010 | Tapsak et al. |
| 2010/0119881 A1 | 5/2010 | Patel et al. |
| 2010/0121169 A1 | 5/2010 | Petisce et al. |
| 2010/0152554 A1 | 6/2010 | Steine et al. |
| 2010/0160759 A1 | 6/2010 | Celentano et al. |

(56) References Cited

U.S. PATENT DOCUMENTS

| | | | |
|---|---|---|---|
| 2010/0168538 A1 | 7/2010 | Keenan et al. |
| 2010/0168545 A1 | 7/2010 | Kamath et al. |
| 2010/0174266 A1 | 7/2010 | Estes |
| 2010/0185071 A1 | 7/2010 | Simpson et al. |
| 2010/0185175 A1 | 7/2010 | Kamen et al. |
| 2010/0191085 A1 | 7/2010 | Budiman |
| 2010/0198142 A1 | 8/2010 | Sloan et al. |
| 2010/0213080 A1 | 8/2010 | Celentano et al. |
| 2010/0230285 A1 | 9/2010 | Hoss et al. |
| 2010/0235439 A1 | 9/2010 | Goodnow et al. |
| 2010/0267161 A1 | 10/2010 | Wu et al. |
| 2010/0274515 A1 | 10/2010 | Hoss et al. |
| 2010/0275108 A1 | 10/2010 | Sloan et al. |
| 2010/0277342 A1 | 11/2010 | Sicurello et al. |
| 2010/0313105 A1 | 12/2010 | Nekoomaram et al. |
| 2010/0324403 A1 | 12/2010 | Brister et al. |
| 2010/0331646 A1 | 12/2010 | Hoss et al. |
| 2010/0332142 A1 | 12/2010 | Shadforth et al. |
| 2011/0031986 A1 | 2/2011 | Bhat et al. |
| 2011/0060530 A1 | 3/2011 | Fennell |
| 2011/0074349 A1 | 3/2011 | Ghovanloo |
| 2011/0125040 A1 | 5/2011 | Crawford et al. |
| 2011/0148905 A1 | 6/2011 | Simmons et al. |
| 2011/0184268 A1 | 7/2011 | Taub |
| 2011/0191059 A1 | 8/2011 | Farrell et al. |
| 2011/0230741 A1 | 9/2011 | Liang et al. |
| 2011/0257895 A1 | 10/2011 | Brauker et al. |
| 2011/0270112 A1 | 11/2011 | Manera et al. |
| 2011/0287528 A1 | 11/2011 | Fern et al. |
| 2012/0108931 A1 | 5/2012 | Taub et al. |
| 2012/0148054 A1 | 6/2012 | Rank et al. |
| 2012/0190989 A1 | 7/2012 | Kaiser et al. |
| 2012/0215092 A1 | 8/2012 | Harris, III et al. |
| 2013/0035575 A1 | 2/2013 | Mayou et al. |
| 2013/0235166 A1 | 9/2013 | Jones et al. |
| 2015/0005601 A1 | 1/2015 | Hoss et al. |
| 2019/0274598 A1 | 9/2019 | Scott et al. |

FOREIGN PATENT DOCUMENTS

| | | |
|---|---|---|
| EP | 1445893 | 8/2004 |
| EP | 1568309 | 8/2005 |
| EP | 1666091 | 6/2006 |
| EP | 1703697 | 9/2006 |
| EP | 1704893 | 9/2006 |
| EP | 1897487 | 11/2009 |
| EP | 1897492 | 11/2009 |
| EP | 2113864 | 11/2009 |
| EP | 1897488 | 12/2009 |
| EP | 1681992 | 4/2010 |
| EP | 1448489 | 8/2010 |
| EP | 1971396 | 8/2010 |
| EP | 2201969 | 3/2011 |
| EP | 1 413 879 | 1/2012 |
| EP | 2153382 | 2/2012 |
| EP | 2284773 | 2/2012 |
| EP | 3 575 796 | 12/2019 |
| GB | 1394171 | 5/1975 |
| GB | 1579690 | 11/1980 |
| GB | 1599241 | 9/1981 |
| GB | 2073891 | 10/1981 |
| GB | 2154003 | 8/1985 |
| GB | 2194892 | 3/1988 |
| GB | 2204408 | 11/1988 |
| GB | 2225637 | 6/1990 |
| GB | 2254436 | 10/1992 |
| GB | 2409951 | 7/2005 |
| JP | 54-041191 | 4/1979 |
| JP | 55-010581 | 1/1980 |
| JP | 55-010583 | 1/1980 |
| JP | 55-010584 | 1/1980 |
| JP | 57-070448 | 4/1982 |
| JP | 60-173457 | 9/1985 |
| JP | 60-173458 | 9/1985 |
| JP | 60-173459 | 9/1985 |
| JP | 62-085855 | 4/1987 |
| JP | 62-114747 | 5/1987 |
| JP | 63-058149 | 3/1988 |
| JP | 63-128252 | 5/1988 |
| JP | 63-139246 | 6/1988 |
| JP | 63-294799 | 12/1988 |
| JP | 63-317757 | 12/1988 |
| JP | 3-028752 | 2/1991 |
| JP | 5-072171 | 3/1993 |
| JP | H-5-196595 | 8/1993 |
| JP | H-6-190050 | 7/1994 |
| JP | 7-072585 | 3/1995 |
| JP | H-8-154903 | 6/1996 |
| JP | H-9-101280 | 4/1997 |
| SU | 1281988 | 1/1987 |
| WO | WO-1985/005119 | 11/1985 |
| WO | WO-1986/000513 | 1/1986 |
| WO | WO-1987/000513 | 1/1987 |
| WO | WO-1987/006040 | 10/1987 |
| WO | WO-1989/002246 | 3/1989 |
| WO | WO-1989/005119 | 6/1989 |
| WO | WO-1989/008713 | 9/1989 |
| WO | WO-1990/000367 | 1/1990 |
| WO | WO-1990/005300 | 5/1990 |
| WO | WO-1990/005910 | 5/1990 |
| WO | WO-1991/001680 | 2/1991 |
| WO | WO-1991/004704 | 4/1991 |
| WO | WO-1991/015993 | 10/1991 |
| WO | WO-1992/001947 | 2/1992 |
| WO | WO-1992/013271 | 8/1992 |
| WO | WO-1994/020602 | 9/1994 |
| WO | WO-1994/027140 | 11/1994 |
| WO | WO-1995/028878 | 2/1995 |
| WO | WO-1995/006240 | 3/1995 |
| WO | WO-1996/007908 | 3/1996 |
| WO | WO-1996/025089 | 8/1996 |
| WO | WO-1996/030431 | 10/1996 |
| WO | WO-1996/035370 | 11/1996 |
| WO | WO-1997/002847 | 1/1997 |
| WO | WO-1997/019344 | 5/1997 |
| WO | WO-1997/020207 | 6/1997 |
| WO | WO-1997/033513 | 9/1997 |
| WO | WO-1997/041421 | 11/1997 |
| WO | WO-1997/042882 | 11/1997 |
| WO | WO-1997/042883 | 11/1997 |
| WO | WO-1997/042886 | 11/1997 |
| WO | WO-1997/042888 | 11/1997 |
| WO | WO-1997/043962 | 11/1997 |
| WO | WO-1997/046868 | 12/1997 |
| WO | WO-1998/009167 | 3/1998 |
| WO | WO-1998/024366 | 6/1998 |
| WO | WO-1998/035053 | 8/1998 |
| WO | WO-1998/052045 | 11/1998 |
| WO | WO-1998/052293 | 11/1998 |
| WO | WO-1999/005966 | 2/1999 |
| WO | WO-1999/032883 | 7/1999 |
| WO | WO-1999/056613 | 11/1999 |
| WO | WO-2000/013580 | 3/2000 |
| WO | WO-2000/018294 | 4/2000 |
| WO | WO-2000/019887 | 4/2000 |
| WO | WO-2000/020626 | 4/2000 |
| WO | WO-2000/033065 | 6/2000 |
| WO | WO 00/49941 | 8/2000 |
| WO | WO-2000/059370 | 10/2000 |
| WO | WO-2000/060350 | 10/2000 |
| WO | WO-2000/062665 | 10/2000 |
| WO | WO-2000/074753 | 12/2000 |
| WO | WO-2000/078210 | 12/2000 |
| WO | WO-2000/078992 | 12/2000 |
| WO | WO-2001/024038 | 4/2001 |
| WO | WO-2001/052935 | 7/2001 |
| WO | WO-2001/057238 | 8/2001 |
| WO | WO-2002/016905 | 2/2002 |
| WO | WO-2002/017210 | 2/2002 |
| WO | WO-2002/058537 | 8/2002 |
| WO | WO 03/012422 | 2/2003 |
| WO | WO 03/032411 | 4/2003 |
| WO | WO-2003/076893 | 9/2003 |
| WO | WO-2003/082091 | 10/2003 |

(56) References Cited

FOREIGN PATENT DOCUMENTS

| WO | WO-2003/085372 | 10/2003 |
|---|---|---|
| WO | WO 03/094714 | 11/2003 |
| WO | WO-2004/047445 | 6/2004 |
| WO | WO-2004/061420 | 7/2004 |
| WO | WO-2004/098405 | 11/2004 |
| WO | WO-2005/010756 | 2/2005 |
| WO | WO 2005/011489 | 2/2005 |
| WO | WO-2005/045744 | 5/2005 |
| WO | WO 2005/070287 | 8/2005 |
| WO | WO-2005/089103 | 9/2005 |
| WO | WO-2005/117269 | 12/2005 |
| WO | WO-2006/024671 | 3/2006 |
| WO | WO 2006/026741 | 3/2006 |
| WO | WO-2006/032653 | 3/2006 |
| WO | WO-2006/037109 | 4/2006 |
| WO | WO-2006/064397 | 6/2006 |
| WO | WO-2007/002189 | 1/2007 |
| WO | WO-2007/007459 | 1/2007 |
| WO | WO-2007/027381 | 3/2007 |
| WO | WO-2007/126444 | 11/2007 |
| WO | WO-2007/053832 | 12/2007 |
| WO | WO-2007/143225 | 12/2007 |
| WO | WO-2008/001366 | 1/2008 |
| WO | WO 2008/021913 | 2/2008 |
| WO | WO-2008/042760 | 4/2008 |
| WO | WO-2008/150428 | 12/2008 |
| WO | WO-2008/153825 | 12/2008 |
| WO | WO-2010/077329 | 8/2010 |
| WO | WO 2010/099507 | 9/2010 |
| WO | WO 2011/011643 | 1/2011 |
| WO | WO 2012/142502 | 10/2012 |

OTHER PUBLICATIONS

S. J. Alcock and A. P. F. Turner, "Continuous analyte monitoring to aid clinical practice," in IEEE Engineering in Medicine and Biology Magazine, vol. 13, No. 3, pp. 319-325, June-Jul. 1994, doi: 10.1109/51.294001. (Year: 1994).*

Nan-Fu Chiu et al., "An Implantable Multifunctional Needle Type Biosensor with Integrated RF Capability," 2005 IEEE Engineering in Medicine and Biology 27th Annual Conference, Shanghai, 2005, pp. 1933-1936, doi: 10.1109/IEMBS.2005.1616830. (Year: 2005).*

Daniels, Jorg, et al. "A/D conversion using an asynchronous delta-sigma modulator and a time-to-digital converter." 2008 IEEE International Symposium on Circuits and Systems. IEEE, 2008. (Year: 2008).*

Hafed, Mohamed, and Gordon W. Roberts. "Sigma-delta techniques for integrated test and measurement." IMTC 2001. Proceedings of the 18th IEEE Instrumentation and Measurement Technology Conference. Rediscovering Measurement in the Age of Informatics (Cat. No. 01CH 37188). Vol. 3. IEEE, 2001. (Year: 2001).*

Davis, Henry, Robert Fine, and Denis Regimbal. "Merging data converters and DSPs for mixed-signal processors." IEEE Micro 10.5 (1990): 17-27. (Year: 1990).*

U.S. Appl. No. 61/227,967, filed Jul. 23, 2009, Hoss, et al.

"In Vivo Glucose Sensing", Chemical Analysis, A Series of Monographs on Analytical Chemistry and its Applications, vol. 174, 466 pages (2010).

Abel, et al., "Biosensors for in vivo glucose measurement: can we cross the experimental stage", Biosensors and Bioelectronics, 17:1059-1070 (2002).

Bard, et al., Electrochemical Methods, Fundamentals and Applications, pp. 174-175 (1980).

Bequette, "Continuous Glucose Monitoring: Real Time Algorithms for Calibration, Filtering, and Alarms", Journal of Diabetes Science and Technology, 4(2):404-418 (2010).

Cengiz, et al., "A Tale of Two Compartments: Interstitial Versus Blood Glucose Monitoring", Diabetes Technology & Therapeutics, 11(1):S-11-S16 (2009).

Chen, et al., "Defining the Period of Recovery of the Glucose Concentration after Its Local Perturbation by the Implantation of a Miniature Sensor", Clin Chem Lab Med, 40(8):786-789 (2002).

Chen, et al., "Glucose microbiosensor based on alumina sol gel matrix/eletropolymerized composite membrane", Biosensors and Bioelectronics, 17:1005-1013 (2002).

Chen, et al., "In Situ Assembled Mass-Transport Controlling Micromembranes and Their Application in Implanted Amperometric Glucose Sensors", Analytical Chemistry, 72(16):3757-3763 (2000).

Chen, et al., "In vivo Glucose Monitoring with Miniature "Wired" Glucose Oxidase Electrodes", Analytical Sciences, 17:i297-i300 (2001).

Choleau, et al., "Calibration of a subcutaneous amperometric glucose sensor Part 1. Effect of measurement uncertainties on the determination of sensor sensitivity and background current", Biosensors and Bioelectronics, 17:641-646 (2002).

Chung, "In vitro Evaluation of the Continuous Monitoring Glucose Sensors with Perfluorinated Tetrafluoroethylene Coatings", Bull. Korean Chem. Soc., 24(4):514-516 (2003).

De Block, et al., "Minimally-Invasive and Non-Invasive Continuous Glucose Monitoring Systems: Indications, Advantages, Limitations and Clinical Aspects", Current Diabetes Reviews, 4:159-168 (2008).

Facchinetti, et al., "Enhanced Accuracy of Continuous Glucose Monitoring by Online Extended Kalman Filtering", Diabetes Technology & Therapeutics, 12(5):353-363 (2010).

Fischer, "Fundamentals of Glucose Sensors", Diabetic Medicine, 8:309-321 (1991).

Fraser, "An Introduction to in vivo Biosensing: Progress and Problems", Biosensors in the Body: Continuous in vivo Monitoring, pp. 1-56 (1997).

FreeStyle Navigator Continuous Glucose Monitoring System, Summary of Safety and Effectiveness Data in support of Pre-Market Approval (PMA) No. P050020, Abbott Diabetes Care, 27 pages (2008).

FreeStyle Navigator Continuous Glucose Monitoring System, User Guide, Abbott Diabetes Care Inc., 195 pages (2008).

Frost, et al., "Implantable chemical sensors for real-time clinical monitoring: progress and challenges", Current Opinion in Chemical Biology, 6:633-641 (2002).

Gerritsen, et al., "Subcutaneously implantable glucose sensors in patients with diabetes mellitus; still many problems", Dutch Journal of Medicine, 146(28):1313-1316 (2002) (with English Machine Translation).

Guardian® Real-Time, Continuous Glucose Monitoring System, User Guide, Medtronic MiniMed, Inc., 181 pages (2006).

Guardian® RT, Continuous Glucose Monitoring System, REF MMT-7900, User Guide, Medtronic MiniMed, 128 pages (2005).

Heinemann, "Continuous Glucose Monitoring by Means of the Microdialysis Technique: Underlying Fundamental Aspects", Diabetes Technology & Therapeutics, 5(4):545-561 (2003).

Heise, et al., "Hypoglycemia Warning Signal and Glucose Sensors: Requirements and Concepts", Diabetes Technology & Therapeutics, 5(4):563-571 (2003).

Heller, "Implanted Electrochemical Glucose Sensors for the Management of Diabetes", Annu. Rev. Biomed. Eng., 01:153-175 (1999).

Heller, et al., "Electrochemical Glucose Sensors and Their Applications in Diabetes Management", Chemical Reviews, 108(7):2482-2505 (2008).

Jiménez, et al., "Glucose sensor based on an amperometric microelectrode with a photopolymerizable enzyme membrane", Sensors and Actuators B, 26-27:421-424 (1995).

Johnson, et al., "Reduction of Electrooxidizable Interferent Effects: Optimization of the Applied Potential for Amperometric Glucose Sensors", Electroanalysis, 6:321-326 (1994).

Knobbe, et al., "The Extended Kalman Filter for Continuous Glucose Monitoring", Diabetes Technology & Therapeutics, 7(1):15-27 (2005).

Koudelka-Hep, "Electrochemical Sensors for in vivo Glucose Sensing", Biosensors in the Body: Continuous in vivo Monitoring, pp. 57-77 (1997).

Kuure-Kinsey, et al., "A Dual-Rate Kalman Filter for Continuous Glucose Monitoring", Proceedings of the 28th IEEE, EMBS Annual International Conference, pp. 63-66 (2006).

(56) References Cited

OTHER PUBLICATIONS

Kvist, et al., "Recent Advances in Continuous Glucose Monitoring: Biocompatibility of Glucose Sensors for Implantation in Subcutis", Journal of Diabetes Science and Technology, 1(5):746-752 (2007).
Ming Li, et al., "Implantable Electrochemical Sensors for Biomedical and Clinical Applications: Progress, Problems, and Future Possibilities", Current Medicinal Chemistry, 14:937-951 (2007).
Nishida, et al., "Development of a ferrocene-mediated needle-type glucose sensor covered with newly designed biocompatible membrane, 2-methacryloyloxyethyl phosphorylcholine-co-n-butyl methacrylate", Medical Progress through Technology, 21:91-103 (1995).
Onuki, et al., "A Review of the Biocompatibility of Implantable Devices: Current Challenges to Overcome Foreign Body Response", Journal of Diabetes Science and Technology, 2(6):1003-1015 (2008).
Palerm, et al., "Hypoglycemia Prediction and Detection Using Optimal Estimation", Diabetes Technology & Therapeutics, 7(1):3-14 (2005).
Rebrin, et al., "Subcutaneous glucose predicts plasma glucose independent of insulin: implications for continuous monitoring", American Journal of Physiology-Endocrinology and Metabolism, 277(3):E561-E571 (1999).
Renard, "Implantable glucose sensors for diabetes monitoring", Min Invas Ther & Allied Technol, 13(2):78-86 (2004).
Rhodes, et al., "Prediction of Pocket-Portable and Implantable Glucose Enzyme Electrode Performance from Combined Species Permeability and Digital Simulation Analysis", Analytical Chemistry, 66(9):1520-1529 (1994).
Robert, "Continuous Monitoring of Blood Glucose", Horm Res 57(suppl 1):81-84 (2002).
Schlosser, et al., "Biocompatibility of Active Implantable Devices", Biosensors in the Body: Continuous in vivo Monitoring, pp. 139-170 (1997).
Schmidtke, et al., "Accuracy of the One-Point in Vivo Calibration of "Wired" Glucose Oxidase Electrodes Implanted in Jugular Veins of Rats in Periods of Rapid Rise and Decline of the Glucose Concentration", Anal. Chem., 70:2149-2155 (1998).
Tierney, et al., "Effect of Acetaminophen on the Accuracy of Glucose Measurements Obtained with the GlucoWatch Biographer", Diabetes Technology & Therapeutics, 2(2):199-207 (2000).
Voskerician, et al., "Sensor Biocompatibility and Biofouling in Real-Time Monitoring", Wiley Encyclopedia of Biomedical Engineering, (John Wiley & Sons, Inc.), pp. 1-19 (2006).
Ward, "A Review of the Foreign-body Response to Subcutaneously-implanted Devices: The Role of Macrophages and Cytokines in Biofouling and Fibrosis", Journal of Diabetes Science and Technology, 2(5):768-777 (2008).
Ward, et al., "A new amperometric glucose microsensor: in vitro and short-term in vivo evaluation", Biosensors & Bioelectronics, 17:181-189 (2002).
Yang, et al., "Glucose Biosensors Based on Oxygen Electrode with Sandwich-Type Membranes", Annals of Biomedical Engineering, 23:833-839 (1995).
Yang, et al., "Glucose Biosensors with Enzyme Entrapped in Polymer Coating", Biomedical Instrumentation & Technology, 29(2):125-133 (1995).
U.S. Appl. No. 15/953,378 (U.S. Pat. No. 11,045,147) filed Apr. 13, 2018 (Jun. 29, 2021).
U.S. Appl. No. 15/090,610 (U.S. Pat. No. 9,968,302) filed Apr. 4, 2016 (May 15, 2018).
U.S. Appl. No. 12/873,294 (U.S. Pat. No. 9,314,195) filed Aug. 31, 2010 (Apr. 19, 2016).
U.S. Appl. No. 15/953,378, filed May 24, 2021, Issue Fee Payment.
U.S. Appl. No. 15/953,378, filed Feb. 22, 2021, Notice of Allowance.
U.S. Appl. No. 15/953,378, filed Oct. 30, 2020, Response to Non-Final Office Action.
U.S. Appl. No. 15/953,378, filed Aug. 24, 2020, Non-Final Office Action.

Abruna, H. D., et al., "Rectifying Interfaces Using Two-Layer Films of Electrochemically Polymerized Vinylpyridine and Vinylbipyridine Complexes of Ruthenium and Iron on Electrodes", Journal of the American Chemical Society, vol. 103, No. 1, 1981, pp. 1-5.
Albery, W. J., et al., "Amperometric Enzyme Electrodes Part II: Conducting Salts as Electrode Materials for the Oxidation of Glucose Oxidase", Journal of ElectroAnalytical Chemistry, vol. 194, 1985, pp. 223-235.
Albery, W. J., et al., "Amperometric Enzyme Electrodes", Philosophical Transactions Of The Royal Society of London, vol. 316, 1987, pp. 107-119.
Alcock, S. J., et al., "Continuous Analyte Monitoring to Aid Clinical Practice", IEEE Engineering in Medicine and Biology Magazine, 1994, pp. 319-325.
Anderson, L. B., et al., "Thin-Layer Electrochemistry: Steady-State Methods of Studying Rate Processes", Journal of ElectroAnalytical Chemistry, vol. 10, 1965, pp. 295-305.
Armour, J. C., et al., "Application of Chronic Intravascular Blood Glucose Sensor in Dogs", Diabetes, vol. 39, 1990, pp. 1519-1526.
Bartlett, P. N., et al., "Covalent Binding of Electron Relays to Glucose Oxidase", Journal of the Chemical Society, Chemical Communications, 1987, pp. 1603-1604.
Bartlett, P. N., et al., "Modification of Glucose Oxidase by Tetrathiafulvalene", Journal of the Chemical Society, Chemical Communications, 1990, pp. 1135-1136.
Bartlett, P. N., et al., "Strategies for the Development of Amperometric Enzyme Electrodes", Biosensors, vol. 3, 1987/88, pp. 359-379.
Bennion, N., et al., "Alternate Site Glucose Testing: A Crossover Design", Diabetes Technology & Therapeutics, vol. 4, No. 1, 2002, pp. 25-33.
Bindra, D. S., et al., "Design and in Vitro Studies of a Needle-Type Glucose Sensor for Subcutaneous Monitoring", Analytical Chemistry, vol. 63, No. 17, 1991, pp. 1692-1696.
Blank, T. B., et al., "Clinical Results From a Non-Invasive Blood Glucose Monitor", Optical Diagnostics and Sensing of Biological Fluids and Glucose and Cholesterol Monitoring II, Proceedings of SPIE, vol. 4624, 2002, pp. 1-10.
Bobbioni-Harsch, E., et al., "Lifespan of Subcutaneous Glucose Sensors and Their Performances During Dynamic Glycaemia Changes in Rats", Journal of Biomedical Engineering, vol. 15, 1993, pp. 457-463.
Boedeker Plastics, Inc., "Polyethylene Specifications", Web Page of Boedeker.com, 2007, pp. 1-3.
Brandt, J., et al., "Covalent Attachment of Proteins to Polysaccharide Carriers by Means of Benzoquinone", Biochimica et Biophysica Acta, vol. 386, 1975, pp. 196-202.
Brooks, S. L., et al., "Development of an On-Line Glucose Sensor for Fermentation Monitoring", Biosensors, vol. 3, 1987/88, pp. 45-56.
Brownlee, M., et al., "A Glucose-Controlled Insulin-Delivery System: Semisynthetic Insulin Bound to Lectin", Science, vol. 206, 1979, 1190-1191.
Cass, A. E., et al., "Ferricinum Ion As An Electron Acceptor for Oxido-Reductases", Journal of ElectroAnalytical Chemistry, vol. 190, 1985, pp. 117-127.
Cass, A. E., et al., "Ferrocene-Medicated Enzyme Electrode for Amperometric Determination of Glucose", Analytical Chemistry, vol. 56, No. 4, 1984, 667-671.
Castner, J. F., et al., "Mass Transport and Reaction Kinetic Parameters Determined Electrochemically for Immobilized Glucose Oxidase", Biochemistry, vol. 23 No. 10, 1984, 2203-2210.
Cheyne, E. H., et al., "Performance of a Continuous Glucose Monitoring System During Controlled Hypoglycaemia in Healthy Volunteers", Diabetes Technology & Therapeutics, vol. 4, No. 5, 2002, pp. 607-613.
Claremont, D. J., et al., "Biosensors for Continuous In Vivo Glucose Monitoring", Proceedings of the Annual International Conference of the IEEE Engineering in Medicine and Biology Society, vol. 10, 1988.
Clark Jr., L. C., et al., "Differential Anodic Enzyme Polarography for the Measurement of Glucose", Oxygen Transport to Tissue: Instrumentation, Methods, and Physiology, 1973, pp. 127-133.

(56) References Cited

OTHER PUBLICATIONS

Clark Jr., L. C., et al., "Electrode Systems for Continuous Monitoring in Cardiovascular Surgery", Annals New York Academy of Sciences, 1962, pp. 29-45.

Clark Jr., L. C., et al., "Long-term Stability of Electroenzymatic Glucose Sensors Implanted in Mice", American Society of Artificial Internal Organs Transactions, vol. XXXIV, 1988, pp. 259-265.

Clarke, W. L., et al., "Evaluating Clinical Accuracy of Systems for Self-Monitoring of Blood Glucose", Diabetes Care, vol. 10, No. 5, 1987, pp. 622-628.

Csoregi, E., et al., "Design and Optimization of a Selective Subcutaneously Implantable Glucose Electrode Based on 'Wired' Glucose Oxidase", Analytical Chemistry, vol. 67, No. 7, 1995, pp. 1240-1244.

Csoregi, E., et al., "Design, Characterization, and One-Point in Vivo Calibration of a Subcutaneously Implanted Glucose Electrode", Analytical Chemistry, vol. 66 No. 19, 1994, pp. 3131-3138.

Csoregi, E., et al., "On-Line Glucose Monitoring by Using Microdialysis Sampling and Amperometric Detection Based on 'Wired' Glucose Oxidase in Carbon Paste", Mikrochimica Acta, vol. 121, 1995, pp. 31-40.

Dai, W. S., et al., "Hydrogel Membranes with Mesh Size Asymmetry Based on the Gradient Crosslinking of Poly(vinyl alcohol)," Journal of Membrane Science, vol. 156, 1999, pp. 67-79.

Davis, G., "Electrochemical Techniques for the Development of Amperometric Biosensors", Biosensors, vol. 1, 1985, pp. 161-178.

Degani, Y., et al., "Direct Electrical Communication Between Chemically Modified Enzymes and Metal Electrodes. 1. Electron Transfer from Glucose Oxidase to Metal Electrodes via Electron Relays, Bound Covalently to the Enzyme", The Journal of Physical Chemistry, vol. 91, No. 6, 1987, pp. 1285-1289.

Degani, Y., et al., "Direct Electrical Communication Between Chemically Modified Enzymes and Metal Electrodes. 2. Methods for Bonding Electron-Transfer Relays to Glucose Oxidase and D-Amino-Acid Oxidase", Journal of American Chemical Society, vol. 110, No. 8, 1988, pp. 2615-2620.

Degani, Y., et al., "Electrical Communication Between Redox Centers of Glucose Oxidase and Electrodes via Electrostatically and Covalently Bound Redox Polymers", Journal of the American Chemical Society, vol. 111, 1989, pp. 2357-2358.

Denisevich, P., et al., "Unidirectional Current Flow and Charge State Trapping at Redox Polymer Interfaces on Bilayer Electrodes: Principles, Experimental Demonstration, and Theory", Journal of the American Chemical Society, vol. 103, 1981, pp. 4727-4737.

Dicks, J. M., et al., "Ferrocene Modified Polypyrrole with Immobilised Glucose Oxidase and its Application in Amperometric Glucose Microbiosensors", Annales de Biologie Clinique, vol. 47, 1989, pp. 607-619.

Diem, P., et al., "Clinical Performance of a Continuous Viscometric Affinity Sensor for Glucose", Diabetes Technology & Therapeutics, vol. 6, 2004, pp. 790-799.

Ellis, C. D., et al., "Selectivity and Directed Charge Transfer through an Electroactive Metallopolymer Film", Journal of the American Chemical Society, vol. 103, No. 25, 1981, pp. 7480-7483.

Engstrom, R. C., "Electrochemical Pretreatment of Glassy Carbon Electrodes", Analytical Chemistry, vol. 54, No. 13, 1982, pp. 2310-2314.

Engstrom, R. C., et al., "Characterization of Electrochemically Pretreated Glassy Carbon Electrodes", Analytical Chemistry, vol. 56, No. 2, 1984, pp. 136-141.

Feldman, B., et al., "A Continuous Glucose Sensor Based on Wired EnzymeTm Technology -Results from a 3-Day Trial in Patients with Type 1 Diabetes", Diabetes Technology & Therapeutics, vol. 5, No. 5, 2003, pp. 769-779.

Feldman, B., et al., "Correlation of Glucose Concentrations in Interstitial Fluid and Venous Blood During Periods of Rapid Glucose Change", Abbott Diabetes Care, Inc. Freestyle Navigator Continuous Glucose Monitor Pamphlet, 2004.

Feldman, B., et al., "Electron Transfer Kinetics at Redox Polymer/Solution Interfaces Using Microelectrodes and Twin Electrode Thin Layer Cells", Journal of ElectroAnalytical Chemistry, vol. 194, 1985, pp. 63-81.

Fischer, H., et al., "Intramolecular Electron Transfer Medicated by 4,41-Bypyridine and Related Bridging Groups", Journal of the American Chemical Society, vol. 98, No. 18, 1976, pp. 5512-5517.

Flentge, F., et al., "An Enzyme-Reactor for Electrochemical Monitoring of Choline and Acetylcholine: Applications in High-Performance Liquid Chromatography, Bran Tissue, Microdialysis and Cerebrospinal Fluid," Analytical Biochemistry, vol. 204, 1992, pp. 305-310.

Foulds, N. C., et al., "Enzyme Entrapment in Electrically Conducting Polymers: Immobilisation of Glucose Oxidase in Polypyrrole and its Application in Amperometric Glucose Sensors", Journal of the Chemical Society, Faraday Transactions 1, vol. 82, 1986, pp. 1259-1264.

Foulds, N. C., et al., "Immobilization of Glucose Oxidase in Ferrocene-Modified Pyrrole Polymers", Analytical Chemistry, vol. 60, No. 22, 1988, pp. 2473-2478.

Frew, J. E., et al., "Electron-Transfer Biosensors", Philosophical Transactions of The Royal Society of London, vol. 316, 1987, pp. 95-106.

Garg, S., et al., "Improvement in Glycemic Excursions with a Transcutaneous, Real- Time Continuous Glucose Sensor", Diabetes Care, vol. 29, No. 1, 2006, pp. 44-50.

Godsland, I. F., et al., "Maximizing the Success Rate of Minimal Model Insulin Sensitivity Measurement in Humans: The Importance of Basal Glucose Levels," Clinical Science, vol. 101, 2001, pp. 1-9.

Gorton, L., et al., "Selective Detection in Flow Analysis Based on the Combination of Immobilized Enzymes and Chemically Modified Electrodes", Analytica Chimica Acta, vol. 250, 1991, pp. 203-248.

Graham, N. B., "Poly(ethylene oxide) and Related Hydrogels," Hydrogels in Medicine and Pharmacy, vol. II: Polymers, Chapter 4, 1987, pp. 95-113.

Gregg, B. A., et al., "Cross-Linked Redox Gels Containing Glucose Oxidase for Amperometric Bionsensor Applications", Analytical Chemistry, vol. 62, No. 3, 1990, pp. 258-263.

Gregg, B. A., et al., "Redox Polymer Films Containing Enzymes. 1. A Redox- Conducting Epoxy Cement: Synthesis, Characterization, and Electrocatalytic Oxidation of Hydroquinone", Journal of Physical Chemistry, vol. 95, No. 15, 1991, 5970-5975.

Hale, p. D., et al., "A New Class of Amperometric Biosensor Incorporating a Polymeric Electron-Transfer Mediator", Journal of the American Chemical Society, vol. 111, No. 9, 1989, pp. 3482-3484.

Harrison, D. J., et al., "Characterization of Perfluorosulfonic Acid Polymer Coated Enzyme Electrodes and a Miniatureized Integrated Potentiostat for Glucose Analysis in Whole Blood", Analytical Chemistry, vol. 60, No. 19, 1988, pp. 2002-2007.

Hawkridge, F. M., et al., "Indirect Coulometric Titration of Biological Electron Transport Components", Analytical Chemistry, vol. 45, No. 7, 1973, pp. 1021-1027.

Heller, A., "Electrical Connection Enzyme Redox Centers to Electrodes", Journal of Physical Chemistry, vol. 96, No. 9, 1990, pp. 3579-3587.

Heller, A., "Electrical Wiring of Redox Enzymes", Accounts of Chemical Research vol. 23, No. 5, 1990, 128-134.

Heller, A., et al., "Amperometric Biosensors Based on Three-Dimensional Hydrogel- Forming Epoxy Networks", Sensors and Actuators B, vol. 13-14, 1993, pp. 180-183.

Ianniello, R. M., et al., "Immobilized Enzyme Chemically Modified Electrode as an Amperometric Sensor", Analytical Chemistry, vol. 53, No. 13, 1981, pp. 2090-2095.

Ianniello, R. M., et al., "Differential Pulse Voltammetric Study of Direct Electron Transfer in Glucose Oxidase Chemically Modified Graphite Electrodes", Analytical Chemistry, vol. 54, No. 7, 1982, pp. 1098-1101.

Ikeda, T., et al., "Kinetics of Outer-Sphere Electron Transfers Between Metal Complexes in Solutions and Polymeric Films on Modified Electrodes", Journal of the American Chemical Society, vol. 103, No. 25, 1981, pp. 7422-7425.

(56) References Cited

OTHER PUBLICATIONS

Ikeda, T., et al., "Glucose Oxidase-Immobilized Benzoquinone-Carbon Paste Electrode as a Glucose Sensor", Agricultural and Biological Chemistry, vol. 49, No. 2, 1985, pp. 541-543.
Isermann, R., "Supervision, Fault-Detection and Fault-Diagnosis Methods—An Introduction", Control Engineering Practice, vol. 5, No. 5, 1997, pp. 639-652.
Isermann, R., et al., "Trends in the Application of Model-Based Fault Detection and Diagnosis of Technical Processes", Control Engineering Practice, vol. 5, No. 5, 1997, pp. 709-719.
Johnson, J. M., et al., "Potential-Dependent Enzymatic Activity in an Enzyme Thin- Layer Cell", Analytical Chemistry, vol. 54, No. 8, 1982, pp. 1377-1383.
Johnson, K. W., "Reproducible Electrodeposition of Biomolecules for the Fabrication of Miniature Electroenzymatic Biosensors", Sensors and Actuators B, vol. 5, 1991, pp. 85-89.
Johnson, K. W., et al., "In vivo Evaluation of an Electroenzymatic Glucose Sensor Implanted in Subcutaneous Tissue", Biosensors & Bioelectronics, vol. 7, 1992, pp. 709-714.
Johnson, P. C., "Peripheral Circulation", John Wiley & Sons, 1978, pp. 198.
Jonsson, G., et al., "An Amperometric Glucose Sensor Made by Modification of a Graphite Electrode Surface With Immobilized Glucose Oxidase and Adsorbed Mediator", Biosensors, vol. 1, 1985, pp. 355-368.
Josowicz, M., et al., "Electrochemical Pretreatment of Thin Film Platinum Electrodes", Journal of the Electrochemical Society, vol. 135 No. 1, 1988, pp. 112-115.
Jungheim, K., et al., "Risky Delay of Hypoglycemia Detection by Glucose Monitoring at the Arm", Diabetes Care, vol. 24, No. 7, 2001, pp. 1303-1304.
Jungheim, K., et al., "How Rapid Does Glucose Concentration Change in Daily Life of Patients with Type 1 Diabetes?", 2002, p. 250.
Kaplan, S. M., "Wiley Electrical and Electronics Engineering Dictionary", IEEE Press, 2004, pp. 141, 142, 548, 549.
Katakis, I., et al., "L-a-Glycerophosphate and L-Lactate Electrodes Based on the Electrochemical Wiring' of Oxidases", Analytical Chemistry, vol. 64, No. 9, 1992, pp. 1008-1013.
Katakis, I., et al., "Electrostatic Control of the Electron Transfer Enabling Binding of Recombinant Glucose Oxidase and Redox Polyelectrolytes", Journal of the American Chemical Society, vol. 116, No. 8, 1994, pp. 3617-3618.
Kemp, G. J., "Theoretical Aspects of One-Point Calibration: Causes and Effects of Some Potential Errors, and Their Dependence on Concentration," Clinical Chemistry, vol. 30, No. 7, 1984, pp. 1163-1167.
Kenausis, G., et al., -Wiring' of Glucose Oxidase and Lactate Oxidase Within a Hydrogel Made with Poly(vinyl pyridine) complexed with [Os(4,41-dimethoxy-2,2'- bipyridine)2C1]+/2+, Journal of the Chemical Society, Faraday Transactions, vol. 92, No. 20, 1996, pp. 4131-4136.
Kerner, W., et al., "The Function of a Hydrogen Peroxide-Detecting Electroenzymatic Glucose Electrode is Markedly Impaired in Human Subcutaneous Tissue and Plasma," Biosensors & Bioelectronics, vol. 8, 1993, pp. 473-482.
Kondepati, V., et al., "Recent Progress in Analytical Instrumentation for Glycemic Control in Diabetic and Critically III Patients", Analytical Bioanalytical Chemistry, vol. 388, 2007, pp. 545-563.
Korf, J., et al., "Monitoring of Glucose and Lactate Using Microdialysis: Applications in Neonates and Rat Brain," Developmental Neuroscience, vol. 15, 1993, pp. 240-246.
Koudelka, M., et al., "In-Vivo Behaviour of Hypodermically Implanted Microfabricated Glucose Sensors", Biosensors & Bioelectronics, vol. 6, 1991, pp. 31-36.
Kulys, J., et al., "Mediatorless Peroxidase Electrode and Preparation of Bienzyme Sensors", Bioelectrochemistry and Bioenergetics, vol. 24, 1990, pp. 305-311.
Lager, W., et al., "Implantable Electrocatalytic Glucose Sensor", Hormone Metabolic Research, vol. 26, 1994, pp. 526-530.
Laurell, T., "A Continuous Glucose Monitoring System Based on Microdialysis", Journal of Medical Engineering & Technology, vol. 16, No. 5, 1992, pp. 187-193.
Lindner, E., et al., "Flexible (Kapton-Based) Microsensor Arrays of High Stability for Cardiovascular Applications", Journal of the Chemical Society, Faraday Transactions, vol. 89, No. 2, 1993, pp. 361-367.
Lo, B., et al., "Key Technical Challenges and Current Implementations of Body Sensor Networks", Body Sensor Networks, 2005, pp. 1-5.
Lodwig, V., et al., "Continuous Glucose Monitoring with Glucose Sensors: Calibration and Assessment Criteria", Diabetes Technology & Therapeutics, vol. 5, No. 4, 2003, pp. 573-587.
Lortz, J., et al., "What is Bluetooth? We Explain The Newest Short-Range Connectivity Technology", Smart Computing Learning Series, Wireless Computing, vol. 8, Issue 5, 2002, pp. 72-74.
Maidan, R., et al., "Elimination of Electrooxidizable Interferant-Produced Currents in Amperometric Biosensors", Analytical Chemistry, vol. 64, No. 23, 1992, pp. 2889-2896.
Malin, S. F., et al., "Noninvasive Prediction of Glucose by Near-Infrared Diffuse Reflectance Spectoscopy", Clinical Chemistry, vol. 45, No. 9, 1999, pp. 1651-1658.
Marko-Varga, G., et al., "Enzyme-Based Biosensor as a Selective Detection Unit in col. Liquid Chromatography", Journal of Chromatography A, vol. 660, 1994, pp. 153-167.
Mastrototaro, J. J., et al., "An Electroenzymatic Glucose Sensor Fabricated on a Flexible Substrate", Sensors and Actuators B, vol. 5, 1991, pp. 139-144.
Mauras, N., et al., "Lack of Accuracy of Continuous Glucose Sensors in Healthy, Nondiabetic Children: Results of the Diabetes Research in Children Network (DirecNet) Accuracy Study," Journal of Pediatrics, 2004, pp. 770-775.
Mcgarraugh, G., et al., "Physiological Influences on Off-Finger Glucose Testing", Diabetes Technology & Therapeutics, vol. 3, No. 3, 2001, pp. 367-376.
Mcgarraugh, G., et al., "Glucose Measurements Using Blood Extracted from the Forearm and the Finger", TheraSense, Inc., 2001, 16 Pages.
Mckean, B. D., et al., "A Telemetry-Instrumentation System for Chronically Implanted Glucose and Oxygen Sensors", IEEE Transactions on Biomedical Engineering, vol. 35, No. 7, 1988, pp. 526-532.
Mcneil, C. J., et al., "Thermostable Reduced Nicotinamide Adenine Dinucleotide Oxidase: Application to Amperometric Enzyme Assay", Analytical Chemistry, vol. 61, No. 1, 1989, pp. 25-29.
Miyawaki, O., et al., "Electrochemical and Glucose Oxidase Coenzyme Activity of Flavin Adenine Dinucleotide Covalently Attached to Glassy Carbon at the Adenine Amino Group", Biochimica et Biophysica Acta, vol. 838, 1985, pp. 60-68.
Moatti-Sirat, D., et al., "Towards Continuous Glucose Monitoring: In Vivo Evaluation of a Miniaturized Glucose Sensor Implanted for Several Days in Rat Subcutaneous Tissue", Diabetologia, vol. 35, 1992, pp. 224-330.
Moatti-Sirat, D., et al., "Evaluating In Vitro and In Vivo the Interference of Ascorbate and Acetaminophen on Glucose Detection by a Needle-Type Glucose Sensor", Biosensors & Bioelectronics, vol. 7, 1992, pp. 345-352.
Moatti-Sirat, D., et al., "Reduction of Acetaminophen Interference in Glucose Sensors by a Composite Nafion Membrane: Demonstration in Rats and Man", Diabetologia, vol. 37, 1994, pp. 610-616.
Morbiducci, U, et al., "Improved Usability of the Minimal Model of Insulin Sensitivity Based on an Automated Approach and Genetic Algorithms for Parameter Estimation", Clinical Science, vol. 112 2007, pp. 257-263.
Mougiakakou, et al., "A Real Time Simulation Model of Glucose-Insulin Metabolism for Type 1 Diabetes Patients", Proceedings of the 2005 IEEE, 2005, pp. 298-301.
Nagy, G., et al., "A New Type of Enzyme Electrode: The Ascorbic Acid Eliminator Electrode", Life Sciences, vol. 31, No. 23, 1982, pp. 2611-2616.
Nakamura, S., et al., "Effect of Periodate Oxidation on the Structure and Properties of Glucose Oxidase", Biochimica et Biophysica Acta., vol. 445, 1976, pp. 294-308.

(56) References Cited

OTHER PUBLICATIONS

Narasimham, K., et al., "p. Benzoquinone Activation of Metal Oxide Electrodes for Attachment of Enzymes", Enzyme and Microbial Technology, vol. 7, 1985, pp. 283-286.
Ohara, T. J., et al., "Glucose Electrodes Based on Cross-Linked [OOPY)2C1]+/2+ Complexed Poly(1-Vinylimidazole) Films", Analytical Chemistry. Vol. 65 No. 23, 1993, pp. 3512-3517.
Ohara, T. J., et al.,—Wired' Enzyme Electrodes for Amperometric Determination of Glucose or Lactate in the Presence of Interfering Substances, Analytical Chemistry, vol. 66, No. 15, 1994, pp. 2451-2457.
Ohara, T. J., "Osmium Bipyridyl Redox Polymers Used in Enzyme Electrodes", Platinum Metals Review, vol. 39, No. 2, 1995, pp. 54-62.
Olievier, C. N., et al., "In Vivo Measurement of Carbon Dioxide Tension with a Miniature Electrodes", Pflugers Archiv: European Journal of Physiology, vol. 373, 1978, pp. 269-272.
Paddock, R. M., et al., "Electrocatalytic Reduction of Hydrogen Peroxide via Direct Electron Transfer From Pyrolytic Graphite Electrodes to Irreversibly Adsorbed Cyctochrome C Peroxidase", Journal of ElectroAnalytical Chemistry, vol. 260, 1989, pp. 487-494.
Palleschi, G., et al., "A Study of Interferences in Glucose Measurements in Blood by Hydrogen Peroxide Based Glucose Probes", Analytical Biochemistry, vol. 159, 1986, pp. 114-121.
Pankratov, I., et al., "Sol-Gel Derived Renewable-Surface Biosensors", Journal of ElectroAnalytical Chemistry, vol. 393, 1995, pp. 35-41.
Parker, R., et al., "Robust Hoe Glucose Control in Diabetes Using a Physiological Model", AIChE Journal, vol. 46, No. 12, 2000, pp. 2537-2549.
Pathak, C., et al., "Rapid Photopolymerization of Immunoprotective Gels in Contact with Cells and Tissue", Journal of the American Chemical Society, vol. 114, No. 21, 1992, pp. 8311-8312.
Pickup, J., et al., "Implantable Glucose Sensors: Choosing the Appropriate Sensing Strategy", Biosensors, vol. 3, 1987/88, pp. 335-346.
Pickup, J., et al., "Potentially-Implantable, Amperometric Glucose Sensors with Mediated Electron Transfer: Improving the Operating Stability", Biosensors, vol. 4, 1989, pp. 109-119.
Pickup, J., et al., "In Vivo Molecular Sensing in Diabetes Mellitus: An Implantable Glucose Sensor with Direct Electron Transfer", Diabetologia, vol. 32, 1989, pp. 213-217.
Pickup, J., "Developing Glucose Sensors for In Vivo Use", Tibtech, vol. 11, 1993, pp. 285-291.
Pishko, M. V., et al., "Amperometric Glucose Microelectrodes Prepared Through Immobilization of Glucose Oxidase in Redox Hydrogels", Analytical Chemistry, vol. 63, No. 20, 1991, pp. 2268-2272.
Poitout, V., et al., "In Vitro and In Vivo Evaluation in Dogs of a Miniaturized Glucose Sensor", ASAIO Transactions, vol. 37, No. 3, 1991, pp. M298-M300.
Poitout, V., et al., "Calibration in Dogs of a Subcutaneous Miniaturized Glucose Sensor Using a Glucose Meter for Blood Glucose Determination", Biosensors & Bioelectronics, vol. 7, 1992, pp. 587-592.
Poitout, V., et al., "A Glucose Monitoring System for On Line Estimation in Man of Blood Glucose Concentration Using a Miniaturized Glucose Sensor Implanted in the Subcutaneous Tissue and a Wearable Control Unit", Diabetolgia, vol. 36, 1993, pp. 658-663.
Pollak, A., et al., "Enzyme Immobilization by Condensation Copolymerization into Cross-Linked Polyacrylamide Gels", Journal of the American Chemical Society, vol. 102, No. 20, 1980, pp. 6324-6336.
Quinn, C. P., et al., "Kinetics of Glucose Delivery to Subcutaneous Tissue in Rats Measured with 0.3-mm Amperometric Microsensors", The American Physiological Society, 1995, E155- E161.
Reach, G., et al., "Can Continuous Glucose Monitoring Be Used for the Treatment of Diabetes?", Analytical Chemistry, vol. 64, No. 6, 1992, pp. 381-386.

Rebrin, K., et al., "Automated Feedback Control of Subcutaneous Glucose Concentration in Diabetic Dogs", Diabetologia, vol. 32, 1989, pp. 573-576.
Reusch, W., "Other Topics: Organometallic Chemistry: Organometallic Compounds: Main Group Organometallic Compounds," Virtual Textbook of Organic Chemistry, 1999, Rev. 2007, 25 pages.
Rodriguez, N., et al., "Flexible Communication and Control Protocol for Injectable Neuromuscular Interfaces", IEEE Transactions on Biomedical Circuits and Systems, vol. 1, No. 1, 2007, pp. 19-27.
Roe, J. N., et al., "Bloodless Glucose Measurements", Critical Review in Therapeutic Drug Carrier Systems, vol. 15, Issue 3, 1998, pp. 199-241.
Sacks (ED), "Guidelines and Recommendations for Laboratory Analysis in the Diagnosis and Management of Diabetes Mellitus," The National Academy of Clinical Biochemistry Presents Laboratory Medicine Practice Guidelines, vol. 13, 2002, pp. 8-11, 21-23, 52-56, 63.
Sakakida, M., et al., "Development of Ferrocene-Mediated Needle-Type Glucose Sensor as a Measure of True Subcutaneous Tissue Glucose Concentrations", Artificial Organs Today, vol. 2, No. 2, 1992, pp. 145-158.
Sakakida, M., et al., "Ferrocene-Mediated Needle-Type Glucose Sensor Covered with Newly Designed Biocompatible Membrane", Sensors and Actuators B, vol. 13-14, 1993, pp. 319-322.
Salditt, P., "Trends in Medical Device Design and Manufacturing", SMTA News and Journal of Surface Mount Technolou, vol. 17, 2004, pp. 19-24.
Salehi, C., et al., "A Telemetry-Instrumentation System for Long-Term Implantable Glucose and Oxygen Sensors", Analytical Letters, vol. 29, No. 13, 1996, pp. 2289-2308.
Samuels, G. J., et al., "An Electrode-Supported Oxidation Catalyst Based on Ruthenium (IV). pH Encapsulation' in a Polymer Film", Journal of the American Chemical Society, vol. 103, No. 2, 1981, pp. 307-312.
Sasso, S. V., et al., "Electropolymerized 1,2-Diaminobenzene as a Means to Prevent Interferences and Fouling and to Stabilize Immobilized Enzyme in Electrochemical Biosensors", Analytical Chemistry. vol. 62, No. 11, 1990, pp. 1111-1117.
Scheller, F., et al., "Enzyme Electrodes and Their Application", Philosophical Transactions of The Royal Society of London B, vol. 316, 1987, pp. 85-94.
Scheller, F. W., et al., "Second Generation Biosensors," Biosensors & Bioelectronics, vol. 6, 1991, pp. 245-253.
Schmehl, R. H., et al., "The Effect of Redox Site Concentration on the Rate of Mediated Oxidation of Solution Substrates by a Redox Copolymer Film", Journal of ElectroAnalytical Chemistry, vol. 152, 1983, pp. 97-109.
Schmidt, F. J., et al., "Calibration of a Wearable Glucose Sensor", The International Journal of Artificial Organs, vol. 15, No. 1, 1992, pp. 55-61.
Schmidtke, D. W., et al., "Measurement and Modeling of the Transient Difference Between Blood and Subcutaneous Glucose Concentrations in the Rat After Injection of Insulin", Proceedings of the National Academy of Sciences, vol. 95, 1998, pp. 294-299.
Shaw, G. W., et al., "In Vitro Testing of a Simply Constructed, Highly Stable Glucose Sensor Suitable for Implantation in Diabetic Patients", Biosensors & Bioelectronics, vol. 6, 1991, pp. 401-406.
Shichiri, M., et al., "Wearable Artificial Endocrine Pancreas With Needle-Type Glucose Sensor", The Lancet, 1982, pp. 1129-1131.
Shichiri, M., et al., "Glycaemic Control in Pancreatectomized Dogs with a Wearable Artificial Endocrine Pancreas", Diabetologia, vol. 24, 1983, pp. 179-184.
Shichiri, M., et al., "Needle-type Glucose Sensor for Wearable Artificial Endocrine Pancreas", Implantable Sensors for Closed-Loop Prosthetic Systems, Chapter 15, 1985, pp. 197-210.
Shichiri, M., et al., "Telemetry Glucose Monitoring Device With Needle-Type Glucose Sensor: A Useful Tool for Blood Glucose Monitoring in Diabetic Individuals", Diabetes Care, vol. 9, No. 2, 1986, pp. 298-301.
Shichiri, M., et al., "In Vivo Characteristics of Needle-Type Glucose Sensor - Measurements of Subcutaneous Glucose Concentrations in Human Volunteers", Hormone and Metabolic Research Supplement Series, vol. 20, 1988, pp. 17-20.

(56) References Cited

OTHER PUBLICATIONS

Shichiri, M., et al., "Membrane Design for Extending the Long-Life of an Implantable Glucose Sensor", Diabetes Nutrition and Metabolism, vol. 2, 1989, pp. 309-313.
Shults, M. C., et al., "A Telemetry-Instrumentation System for Monitoring Multiple Subcutaneously Implanted Glucose Sensors", IEEE Transactions on Biomedical Engineering, vol. 41, No. 10, 1994, pp. 937-942.
Sittampalam, G., et al., "Surface-Modified Electrochemical Detector for Liquid Chromatography", Analytical Chemistry. Vol. 55 No. 9, 1983, pp. 1608-1610.
Skoog, D. A., et al., "Evaluation of Analytical Data," Fundamentals of Analytical Chemistry, 1966, p. 55.
Slattery, C., et al., "A Reference Design for High-Performance, Low-Cost Weigh Scales", Analog Dialogue 39-12, 2005 pp. 1-6.
Soegijoko, S., et al., "External Artificial Pancreas: A New Control Unit Using Microprocessor", Hormone and Metabolic Research Supplement Series, vol. 12, 1982, pp. 165-169.
Sprules, S. D., et al., "Evaluation of a New Disposable Screen-Printed Sensor Strip for the Measurement of NADH and Its Modification to Produce a Lactate Biosensor Employing Microliter Volumes", Electroanalysis, vol. 8, No. 6, 1996, pp. 539-543.
Sternberg, F., et al., "Calibration Problems of Subcutaneous Glucosensors when Applied 'In-Situ' in Man", Hormone and Metabolic Research, vol. 26, 1994, pp. 523-526.
Sternberg, R., et al., "Covalent Enzyme Coupling on Cellulose Acetate Membranes for Glucose Sensor Development", Analytical Chemistry, vol. 60, No. 24, 1988, pp. 2781-2786.
Sternberg, R., et al., "Study and Development of Multilayer Needle-Type Enzyme- Based Glucose Microsensors", Biosensors, vol. 4, 1988, pp. 27-40.
Suekane, M., "Immobilization of Glucose Isomerase", Zettschrift fur Allgemeine Mikrobiologie, vol. 22, No. 8, 1982, pp. 565-576.
Tajima, S., et al., "Simultaneous Determination of Glucose and 1,5-Anydroglucitol", Chemical Abstracts, vol. 111, No. 25, 1989, pp. 394.
Takamura, A., et al., Drug release from Poly(vinyl alcohol) Gel Prepared by Freeze- Thaw Procedure, Journal of Controlled Release, vol. 20, 1992, pp. 21-27.
Tarasevich, M. R., "Bioelectrocatalysis", Comprehensive Treatise of Electrochemistry, vol. 10, 1985, pp. 231-295.
Tatsuma, T., et al., "Enzyme Monolayer—and Bilayer-Modified Tin Oxide Electrodes for the Determination of Hydrogen Peroxide and Glucose", Analytical Chemistry, vol. 61, No. 21, 1989, pp. 2352-2355.
Taylor, C., et al., "'Wiring' of Glucose Oxidase Within a Hydrogel Made with Polyvinyl Imidazole Complexed with [(Os-4,4'-dimethoxy-2,2'-bipyridine)Clr2+", Journal of ElectroAnalytical Chemistry, vol. 396, 1995, pp. 511-515.
Thompson, M., et al., "In Vivo Probes: Problems and Perspectives", Clinical Biochemistry, vol. 19, 1986, pp. 255-261.
Travenol Laboratories, Inc., An Introduction to "Eugly", Book 1, 1985, pp. 1-22.
Trojanowicz, M., et al., "Enzyme Entrapped Polypyrrole Modified Electrode for Flow-Injection Determination of Glucose", Biosensors & Bioelectronics, vol. 5, 1990, pp. 149-156.
Tsalikian, E., et al., "Accuracy of the GlucoWatch G2® Biographer and the Continuous Glucose Monitoring System During Hypoglycemia: Experience of the Diabetes Research in Children Network", Diabetes Care, vol. 27, No. 3, 2004, pp. 722-726.
Turner, A., et al., "Diabetes Mellitus: Biosensors for Research and Management", Biosensors, vol. 1, 1985, pp. 85-115.
Turner, R. F., et al., "A Biocompatible Enzyme Electrode for Continuous in vivo Glucose Monitoring in Whole Blood", Sensors and Actuators B, vol. 1, 1990, pp. 561-564.
Tuzhi, P., et al., "Constant Potential Pretreatment of Carbon Fiber Electrodes for In Vivo Electrochemistry", Analytical Letters, vol. 24, No. 6, 1991, pp. 935-945.
Umana, M., "Protein-Modified Electrochemically Active Biomaterial Surface", U.S. Army Research Office Analytical and Chemical Sciences Research Triangle Institute, 1988, pp. 1-9.
Updike, S. J., et al., "Principles of Long-Term Fully Implanted Sensors with Emphasis on Radiotelemetric Monitoring of Blood Glucose from Inside a Subcutaneous Foreign Body Capsule (FBC)", Biosensors in the Body: Continuous in vivo Monitoring, Chapter 4, 1997, pp. 117-137.
Urban, G., et al., "Miniaturized Thin-Film Biosensors Using Covalently Immobilized Glucose Oxidase", Biosensors & Bioelectronics, vol. 6, 1991, pp. 555-562.
Velho, G., et al., "In Vitro and In Vivo Stability of Electrode Potentials in Needle-Type Glucose Sensors", Diabetes, vol. 38, No. 2, 1989, pp. 164-171.
Velho, G., et al., "Strategies for Calibrating a Subcutaneous Glucose Sensor", Biomedica Biochimica Acta, vol. 48, 1989, pp. 957-964.
Von Woedtke, T., et al., "In Situ Calibration of Implanted Electrochemical Glucose Sensors", Biomedica Biochimica Acta, vol. 48, 1989, pp. 943-952.
Vreeke, M. S., et al., "Hydrogen Peroxide Electrodes Based on Electrical Connection of Redox Centers of Various Peroxidases to Electrodes through a Three-Dimensional Electron-Relaying Polymer Network", Diagnostic Biosensors Polymers, Chapter 15, 1993, pp. 180-193.
Vreeke, M., et al., "Hydrogen Peroxide and 0-Nicotinamide Adenine Dinucleotide Sensing Amperometric Electrodes Based on Electrical Connection of Horseradish Peroxidase Redox Centers to Electrodes through a Three-Dimensional Electron Relaying Polymer Network", Analytical Chemistry. Vol. 64 No. 24, 1992, pp. 3084-3090.
Wang, D. L., et al., "Miniaturized Flexible Amperometric Lactate Probe", Analytical Chemistry, vol. 65, No. 8, 1993, pp. 1069-1073.
Wang, J., et al., "Activation of Glassy Carbon Electrodes by Alternating Current Electrochemical Treatment", Analytica Chimica Acta, vol. 167, 1985, pp. 325-334.
Wang, J., et al., "Amperometric Biosensing of Organic Peroxides with Peroxidase-Modified Electrodes", Analytica Chimica Acta, vol. 254, 1991, pp. 81-88.
Wang, J., et al., "Screen-Printable Sol-Gel Enzyme-Containing Carbon Inks", Analytical Chemistry, vol. 68, No. 15, 1996, pp. 2705-2708.
Wang, J., et al., "Sol-Gel-Derived Metal-Dispersed Carbon Composite Amperometric Biosensors", Electroanalysis, vol. 9, No. 1, 1997, pp. 52-55.
Williams, D. L., et al., "Electrochemical-Enzymatic Analysis of Blood Glucose and Lactate", Analytical Chemistry, vol. 42, No. 1, 1970, pp. 118-121.
Wilson, G. S., et al., "Progress Toward the Development of an Implantable Sensor for Glucose", Clinical Chemistry, vol. 38, No. 9, 1992, pp. 1613-1617.
Yabuki, S., et al., "Electro-Conductive Enzyme Membrane", Journal of the Chemical Society, Chemical Communications, 1989, pp. 945-946.
Yang, C., et al., "A Comparison of Physical Properties and Fuel Cell Performance of Nafion and Zirconium Phosphate/Nafion Composite Membranes," Journal of Membrane Science, vol. 237, 2004, pp. 145-161.
Yao, T., "A Chemically-Modified Enzyme Membrane Electrode as an Amperometric Glucose Sensor", Analytica Chimica Acta, vol. 148, 1983, pp. 27-33.
Yao, S. J., et al., "The Interference of Ascorbate and Urea in Low-Potential Electrochemical Glucose Sensing", Proceedings of the Twelfth Annual International Conference of the IEEE Engineering in Medicine and Biology Society, vol. 12, Part 2, 1990, pp. 487-489.
Yang, L., et al., "Determination of Oxidase Enzyme Substrates Using Cross-Flow Thin- Layer Amperometry", Electroanalysis, vol. 8, No. 8-9, 1996, pp. 716-721.
Ye, L., et al., "High Current Density ' Wired' Quinoprotein Glucose Dehydrogenase Electrode", Analytical Chemistry, vol. 65, No. 3, 1993, pp. 238-241.
Yildiz, A., et al., "Evaluation of an Improved Thin-Layer Electrode", Analytical Chemistry, vol. 40, No. 7, 1968, pp. 1018-1024.

(56) References Cited

OTHER PUBLICATIONS

Zamzow, K., et al., "New Wearable Continuous Blood Glucose Monitor (BGM) and Artificial Pancreas (AP)", Diabetes, vol. 39, 1990, pp. 5A-20.
Zhang, Y., et al., "Application of Cell Culture Toxicity Tests to the Development of Implantable Biosensors", Biosensors & Bioelectronics, vol. 6, 1991, pp. 653-661.
Zhang, Y., et al., "Elimination of the Acetaminophen Interference in an Implantable Glucose Sensor", Analytical Chemistry, vol. 66, No. 7, 1994, pp. 1183-1188.
European Patent Application No. 10812781.2, Extended European Search Report mailed Mar. 12, 2014.
European Patent Application No. 10812781.2, Examination Report mailed Jul. 18, 2018.
PCT Application No. PCT/US2010/047411, International Search Report and Written Opinion of the International Searching Authority mailed Oct. 22, 2010.
PCT Application No. PCT/US2010/047411, Preliminary Report on Patentability and Written Opinion of the International Searching Authority mailed Mar. 15, 2012.
U.S. Appl. No. 12/873,294, Advisory Action mailed Feb. 3, 2015.
U.S. Appl. No. 12/873,294, Notice of Allowance mailed Dec. 23, 2015.
U.S. Appl. No. 12/873,294, Office Action mailed Apr. 17, 2015.
U.S. Appl. No. 12/873,294, Office Action mailed Dec. 11, 2013.
U.S. Appl. No. 12/873,294, Office Action mailed Jul. 27, 2015.
U.S. Appl. No. 12/873,294, Office Action mailed Jul. 9, 2014.
U.S. Appl. No. 12/873,294, Office Action mailed Sep. 16, 2014.
U.S. Appl. No. 15/090,610, Advisory Action mailed Aug. 11, 2017.
U.S. Appl. No. 15/090,610, Notice of Allowance mailed Jan. 22, 2018.
U.S. Appl. No. 15/090,610, Office Action mailed Feb. 10, 2017.
U.S. Appl. No. 15/090,610, Office Action mailed Jun. 1, 2017.
U.S. Appl. No. 60/687,199, filed Jun. 2, 2005, Ward, et al.
U.S. Appl. No. 61/155,889, filed Feb. 26, 2009, Hoss, et al.
Atanasov, et al., "Implantation of a refillable glucose monitoring-telemetry device"; Biosensors & Bioelectronics, 12(7):669-680 (1997).
Balakrishnan, et al., "A Primer on Statistical Distributions", John Wiley & Sons, Inc., 13 pages (2003).
Bindra, "Development of potentially implantable glucose sensors", The University of Arizona, 227 pages (1990).
Chen, et al., "A novel fault-tolerant sensor system for sensor drift compensation", Sensors and Actuators, A 147:623-632 (2008).
Choleau, et al., "Calibration of a subcutaneous amperometric glucose sensor implanted for 7 days in diabetic patients Part 2. Superiority of the one-point calibration method", Biosensors and Bioelectronics, 17 :647-654 (2002).
FreeStyle Navigator Continuous Glucose Monitoring System, User's Guide, Abbott Diabetes Care Inc., 38 pages (2008).
Gerritsen, et al., "Performance of subcutaneously implanted glucose sensors for continuous monitoring", The Netherlands Journal of Medicine, 54:167-179 (1999).
Guardian® REAL-Time, Continuous Glucose Monitoring System, User Guide, Medtronic MiniMed, Inc., 184 pages (2006).
Kalivas, et al., "Compensation for Drift and Interferences in Multicomponent Analysis", Laboratory for Chemometrics, Department of Chemistry, University of Washington, 38 pages (1982).
Koschinsky, et al., "Sensors for glucose monitoring: technical and clinical aspects", Diabetes/Metabolism Research and Reviews, 17:113-123 (2001).
Koschwanez, et al., "In Vitro, in Vivo and post explantation testing of glucose-detecting biosensors: Current methods and recommendations", Biomaterials, 28:3687-3703 (2007).
Moussy, et al. "Performance of Subcutaneously Implanted Needle-Type Glucose Sensors Employing aNovel Trilayer Coating", Anal. Chem, 65:2072-2077 (1993).
Pickup, et al., "In Vivo glucose sensing for diabetes management: progress towards non-invasive monitoring", BMJ, 319, pp. 1-4 (1999).
Pickup, et al., "Responses and calibration of amperometric glucose sensors implanted in the subcutaneous tissue of man", Acta Diabetol, 30:143-148 (1993).
Thévenot, et al., "Electrochemical Biosensors: Recommended Definitions and Classification (Technical Report)", Pure Appl. Chem. 71(12):2333-2348 (1999).
U.S. Appl. No. 12/842,013 Office Action mailed Aug. 26, 2015.
U.S. Appl. No. 12/842,013 Office Action mailed Mar. 23, 2016.
U.S. Appl. No. 12/842,013 Office Action mailed Nov. 6, 2014.
Walt, et al., "The chemistry of enzyme and protein immobilization with glutaraldehyde", Trends in Analytical Chemistry, 13(10):425-430 (1994).
Ward, et al., "Rise in background current over time in a subcutaneous glucose sensor in the rabbit: relevance to calibration and accuracy", Biosensors & Bioelectronics, 15:53-61 (2000).
Wilson, et al., "Biosensors for real-time in Vivo measurements", Biosensors and Bioelectronics, 20:2388-2403 (2005).
Wisniewski, et al., "Analyte flux through chronically implanted subcutaneous polyamide membranes differs in humans and rats", Am J Physiol Endocrinol Metab, 282zE1316-E1323 (2002).
Zhang, "Investigations of potentially implantable glucose sensors", University of Kansas, 24 pages (1991).
"Abbott Receives CE Mark for Freestyle® Libre, A Revolutionary Glucose Monitoring System for People with Diabetes," 8 pages (2023).
ATTD Program, 4 pages (2009).
Boise, Interview with Dexcom CEO, Dexcom CEO Kevin Sayer Explains G6, 9 pages (2018).
Dexcom (DXCM) Company Profile, 2017 /Q4 Earnings call transcript, 12 pages (2017).
Dexcom G6 Continuous Glucose Monitoring System User Guide, 7 pages (2020).
Email communication from Sophie Hood, Jan. 24, 2023, 6 pages.
Hall, Interview with Kevin Sayer, President and CEO of Dexcom About The New Dexcom G6, College Diabetes Network, 6 pages (2021).
Hoss et al., "Continuous glucose monitoring in the tissue: Do we really need to calibrate in-vivo?," Diabetes Technology & Therapeutics, vol. 11, No. 2, (2009).
Omnipod image, Exhibit 182, 2 pages Sep. 22, 2022.
Sayer, CGMS Changing Diabetes Management: Kevin Sayer, DIC Interview Transcript, Featuring Steve Freed, 11 pages (2019).
S&P Global Market Intelligence "DexCom, Inc. NasdaqGS:DXCM, Company Conference Presentation," 17 pages (2021).
S&P Global Market Intelligence "DexCom, Inc. NasdaqGS:DXCM, Company Conference Presentation," 10 pages (2020).
S&P Global Market Intelligence "DexCom, Inc. NasdaqGS:DXCM, Company Conference Presentation," 11 pages (2019).
Sonix, Dexcom CEO—Prime Position in Our Market—Mad Money—CNBC.mp4, 4 pages (2023).
U.S. Food & Drug Administration, "Deciding When to Submit a 510(k) for a Change to an Existing Device, Guidance for Industry and Food and Drug Administration Staff," 78 pages (2017).
U.S. Food & Drug Administration, "Deciding When to Submit a 510(k) for a Software Change to an Existing Device, Guidance for Industry and Food and Drug Administration Staff," 32 pages (2017).
Watkin, "An Introduction to Flash Glucose Monitoring," 16 pages (2013).
Dock, E. et al., "Multivariate data analysis of dynamic amperometric biosensor responses from binary analyte mixtures - application of sensitivity correction algorithms", Talanta, 65, 2005, pp. 298-305.
FreeStyle Navigator Continuous Glucose Monitoring System, Dept of Health & Human Services, Food and Drug Administration, Mar. 12, 2008, 8 pages.
Hoss, U. et al., "Continuous Glucose Monitoring in Subcutaneous Tissue Using Factory- Calibrated Sensors: A Pilot Study", 2010, vol. 12, No. 8, pp. 591-597.
Hoss, U. et al., "Factory-Calibrated Continuous Glucose Sensors: The Science Behind the Technology", Diabetes Technology & Therapeutics, 2017, vol. 19, Suppl. 2, pp. S-44-S-50.
Hanson, K. et al., "Comparison of Point Accuracy Between Two Widely Used Continuous Glucose Monitoring Systems", Journal of Diabetes Science and Technology, 2024, pp. 1-10.

(56) References Cited

OTHER PUBLICATIONS

Abbott Press Release—"Abbott Receives CE Mark for FreeStyle® Libre, A Revolutionary Glucose Monitoring System for People with Diabetes" retrieved from https://abbott.mediaroom.com/2014-09-03-Abbott-Receives-CE-Mark-for-FreeStyle-Libre-a-Revolutionary-Glucose-Monitoring-System-for-People-with-Diabetes/, Sep. 3, 2014, 3 pages.
Abbott Press Release—"Abbott Receives FDA Approval for the FreeStyle Libre Pro™ System, A Revolutionary Diabetes Sensing Technology for Healthcare Professionals to Use with their Patients" retrieved from https://abbott.mediaroom.com/2016-09-28-Abbott-Receives-FDA-Approval-for-the-FreeStyle-Libre-Pro-System-a-Revolutionary-Diabetes-Sensing-Technology-for-Healthcare-Professionals-to-use-with-their-Patients/, Sep. 28, 2016, 5 pages.
Abbott Press Release—"Abbott's FreeStyle® Libre 14 Day Flash Glucose Monitoring System Now Approved in U.S." retrieved from https://abbott.mediaroom.com/2018-07-27-Abbotts-FreeStyle-R-Libre-14-Day-Flash-Glucose-Monitoring-System-Now-Approved-in-U-S/, Jul. 27, 2018, 3 pages.
Anzhsn, National Horizon Scanning Unit Horizon Scanning Report, "GlucoWatch® G2 Biographer for the non-invasive monitoring of glucose levels", 46 pages, May 2004.
Cather, CGM Frustrations Survey dated June 2020, 37 pages in Abbott *Diabetes Care Inc., et al. v. Dexcom, Inc.*, Case No. 1:21-CV-00977-KAJ (District of Delaware).
Clinical Trials, Competitor and Ecosystem Players dated June 25, 2020, 29 pages in *Abbott Diabetes Care Inc, et al. v. Dexcom, Inc.*, Case No. 1:21-cv-O0977-KAJ (District of Delaware).
Declaration of Dr. Anthony Edward Cass in Support of Petition for Inter Parles Review of U.S. Pat. No. 11,020,031 in *Abbott Diabetes Care Inc. v. Dexcom, Inc.*, Case No. 1PR2024-00890, In the United States Patent and Trademark Office, Before the Patent Trial and Appeal Board, May 10, 2024, 138 pages.
Declaration of Karl R. Leinsing, MSME, PE, in Support of Abbott's Motion for Summary Judgment dated May 19, 2023, 81 pages in *Abbott Diabetes Care Inc., et al. V. Dexcom, Inc.*, Case No. 1:21-CV-00977-KAJ (District of Delaware).
Effectiveness and Safety Study of the DexComTM G4 Continuous Glucose Monitoring System, DeXCom, Inc, U.S. National Library of Medicine, ClinicalTrialsgov Identifier: NCT01111370, 4 pages (2017).
E-mail Communication from Christopher M. Dougherty regarding Bi Monthly Global Commercial Insights Meeting dated Dec. 17, 2019, 69 pages in *Abbott Diabetes Care Inc., et al. v. Dexcom, Inc.*, Case No. 1:21-cv-00977-KAJ (District of Delaware).
Design U.S. Appl. No. 29/101,218, filed Feb. 25, 1999, 11 pages.
U.S. Pat. No. 11,020,031 issued Jun. 1, 2021, 1058 pages.
FreeStyle Libre 2 HCP Pulse, Mar. 2021 Report, dated Mar. 1, 2021, 14 pages in *Abbott Diabetes Care Inc., et al. v. Dexcom, Inc.*, Case No. 1:21-CV-00977-KAJ (District of Delaware).
Godek, et al., Chapter 2, "The Macrophage in Wound Healing Surrounding Implanted Devices", In Vivo Glucose Sensing, 36 pages (2010).
Gross, et al., "Performance Evaluation of the MiniMed® Continuous Glucose Monitoring System During Patient Home Use", Diabetes Technology & Therapeutics, vol. 2, No. 1, pp. 49-56 (2000).
Heller, "Integrated Medical Feedback Systems for Drug Delivery", American Institute of Chemical Engineers Journal, vol. 51, No. 4, pp. 1054-1066 (2005).
Henning, Chapter 5, "Commercially Available Continuous Glucose Monitoring Systems", In Vivo Glucose Sensing, 50 pages (2010).
Kovatchev, et al., "Evaluating the Accuracy of Continuous Glucose-Monitoring Sensors", Diabetes Care, vol. 27, No. 8, pp. 1922-1928 (2004).
Lesperance, et al., "Calibration of the Continuous Glucose Monitoring System for Transient Glucose Monitoring", Diabetes Technology & Therapeutics, vol. 9, No. 2, pp. 183-190 (2007).
Project Status Update, Glucose Sensor Applicator Dexcom (project #2554), Design Concepts, Inc., 6 pages (2014).
Seagrove Partners, International Diabetes Device, 2022 Blue Book dated 2022, 143 pages in *Abbott Diabetes Care Inc., et al. v. Dexcom, Inc.*, Case No. 1:21-cv-00977-KAJ (District of Delaware).
Wilson, et al., Chapter 1, "Introduction to the Glucose Sensing Problem," In Vivo Glucose Sensing, 32 pages (2010).
Wisniewski, et al., "Characterization of implantable biosensor membrane biofouling", Fresenius J Anal Chem, 366:611-621 (2000).
Dorland's Illustrated Medical 31st Edition Dictionary, definition of "fluid, interstitial", (2007), 3 pages.
Forlenza, G.P., et al., "Factory-Calibrated Continuous Glucose Monitoring: How and Why It Works, and the Dangers of Reuse Beyond Approved Duration of Wear", Diabetes Technology & Therapeutics, vol. 21, No. 4, (2019) 13 pages.
Stephens Inc., Research Bulletin, "DexCom, Inc., A True Game Changer: The G6 Eliminates Fingersticks", (2018) 5 pages.
The American Heritage® Medical Dictionary, definition of "catheter" and "interstitial fluid", (2007), 4 pages.

\* cited by examiner

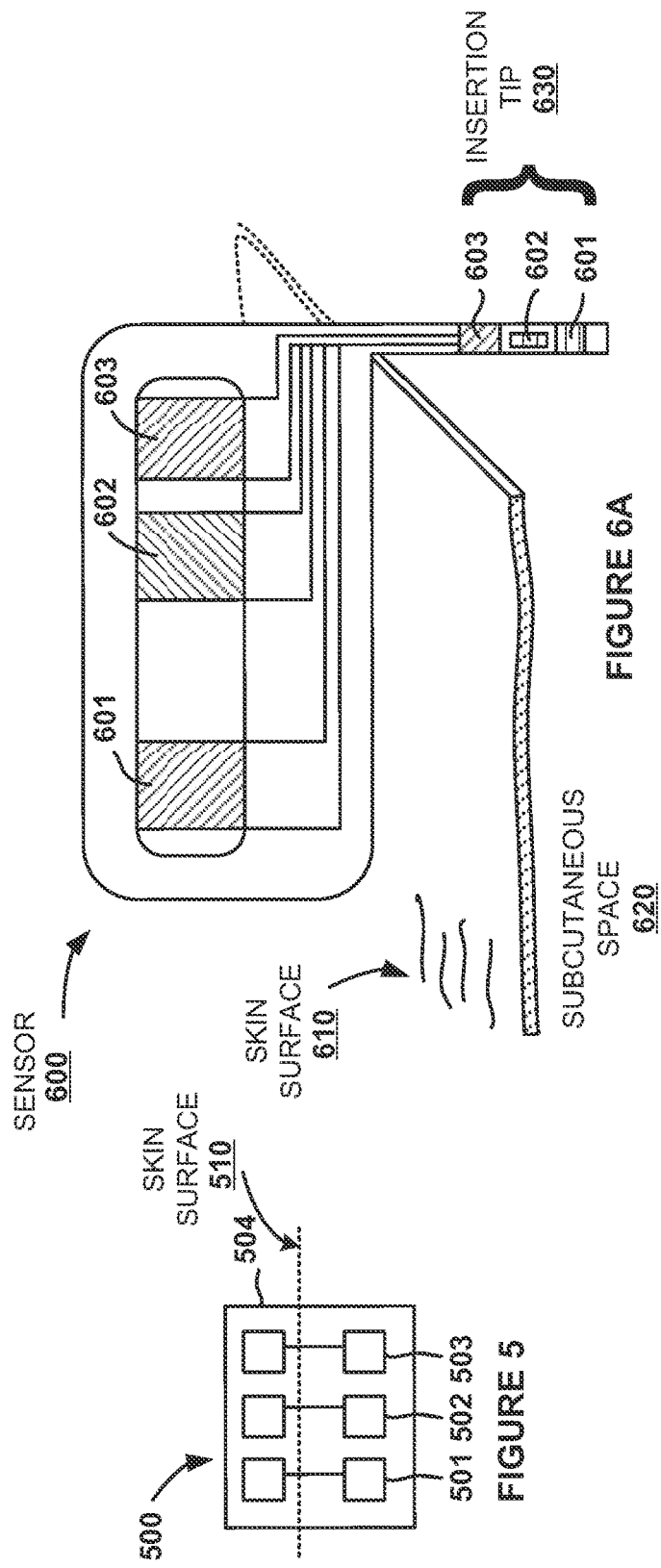
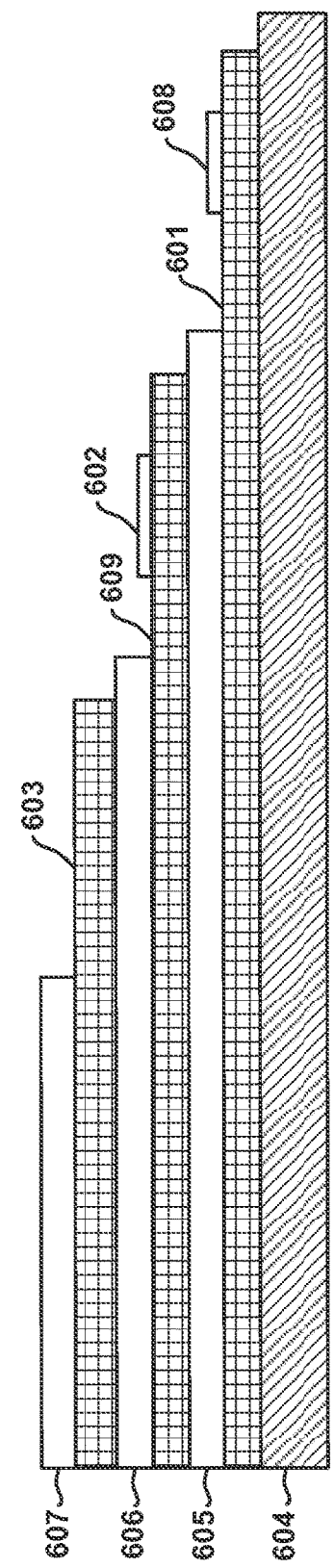

ANALYTE SIGNAL PROCESSING DEVICE AND METHODS

RELATED APPLICATIONS

The present application is a continuation of U.S. patent application Ser. No. 15/953,378 filed Apr. 13, 2018, now allowed, which is a continuation of U.S. patent application Ser. No. 15/090,610 filed Apr. 4, 2016, now U.S. Pat. No. 9,968,302, which is a continuation of U.S. patent application Ser. No. 12/873,294 filed Aug. 31, 2010, now U.S. Pat. No. 9,314,195, which claims the benefit of U.S. Provisional Application No. 61/238,658 filed Aug. 31, 2009, entitled "Analyte Signal Processing Device and Methods", the disclosures of each of which are incorporated herein by reference for all purposes.

BACKGROUND

The monitoring of the level of glucose or other analytes, such as lactate or oxygen, in certain individuals is vitally important to their health. High or low levels of glucose or other analytes may have detrimental effects. The monitoring of glucose is particularly important to individuals with diabetes, as they must determine when insulin is needed to reduce glucose levels in their bodies or when additional glucose is needed to raise the level of glucose in their bodies.

A conventional technique used by many diabetics for personally monitoring their blood glucose level includes the periodic drawing of blood, the application of that blood to a test strip, and the determination of the blood glucose level using colorimetric, electrochemical, or photometric detection. This technique does not permit continuous or automatic monitoring of glucose levels in the body, but typically must be performed manually on a periodic basis. Unfortunately, the consistency with which the level of glucose is checked varies widely among individuals. Many diabetics find the periodic testing inconvenient and they sometimes forget to test their glucose level or do not have time for a proper test. In addition, some individuals wish to avoid the pain associated with the test. These situations may result in hyperglycemic or hypoglycemic episodes. An in vivo glucose sensor that continuously or automatically monitors the individual's glucose level would enable individuals to more easily monitor their glucose, or other analyte, levels.

A variety of devices have been developed for continuous or automatic monitoring of analytes, such as glucose, in the blood stream or interstitial fluid. A number of these devices use electrochemical sensors which are directly implanted into a blood vessel or in the subcutaneous tissue of a patient. However, these devices are often difficult to reproducibly and inexpensively manufacture in large numbers. In addition, these devices are typically large, bulky, and/or inflexible, and many cannot be used effectively outside of a controlled medical facility, such as a hospital or a doctor's office, unless the patient is restricted in his activities.

The patient's comfort and the range of activities that can be performed while the sensor is implanted are important considerations in designing extended-use sensors for continuous or automatic in vivo monitoring of the level of an analyte, such as glucose. There is a need for a small, comfortable device which can continuously monitor the level of an analyte, such as glucose, while still permitting the patient to engage in normal activities. Continuous and/or automatic monitoring of the analyte can provide a warning to the patient when the level of the analyte is at or near a threshold level. For example, if glucose is the analyte, then the monitoring device might be configured to warn the patient of current or impending hyperglycemia or hypoglycemia. The patient can then take appropriate actions.

SUMMARY

An analyte signal processing method in one aspect of the present disclosure includes determining a measurement time period, receiving a plurality of signals associated with a monitored analyte level during the determined measurement time period from an analyte sensor, modulating the received plurality of signals to generate a data stream over the measurement time period, and accumulating the generated data stream to determine an analyte signal corresponding to the monitored analyte level associated with the measurement time period.

A signal processing device used for processing analyte related signals in accordance with another aspect includes an analyte sensor interface electronics for receiving a plurality of analyte related signals from an analyte sensor over a measurement time period, a data processing component operatively coupled to the analyte sensor interface electronics for processing the received plurality of analyte related signals, the data processing component including a signal filtering component to filter the received plurality of analyte related signals, a signal conversion component operatively coupled to the signal filtering component to convert the received filtered plurality of analyte related signals to determine an analyte level associated with a monitored analyte level during the measurement time period.

An analyte monitoring system in still another aspect includes an analyte sensor including a working electrode having a sensing layer at least a portion of which is configured for fluid contact with an interstitial fluid under a skin layer, and a data processing unit comprising an application specific integrated circuit (ASIC) in signal communication with the analyte sensor for receiving a plurality of signals related to a monitored analyte level from the sensor over a monitoring time period, the data processing unit including: a signal filtering component to filter the received plurality of signals; and a signal conversion component to convert the received filtered plurality of analyte related signals to determine a corresponding analyte level associated with a monitored analyte level during a measurement time period, said monitoring time period including multiple measurement time periods.

These and other features, objects and advantages of the various embodiments of the present disclosure will become apparent to those persons skilled in the art upon reading the details of the present disclosure as more fully described below.

BRIEF DESCRIPTION OF THE DRAWINGS

FIG. 5 shows a schematic diagram of an embodiment of an analyte sensor according to the present disclosure; and FIGS. 6A and 6B show a perspective view and a cross sectional view, respectively, of another embodiment of an analyte sensor.

INCORPORATED BY REFERENCE

Figure 1:
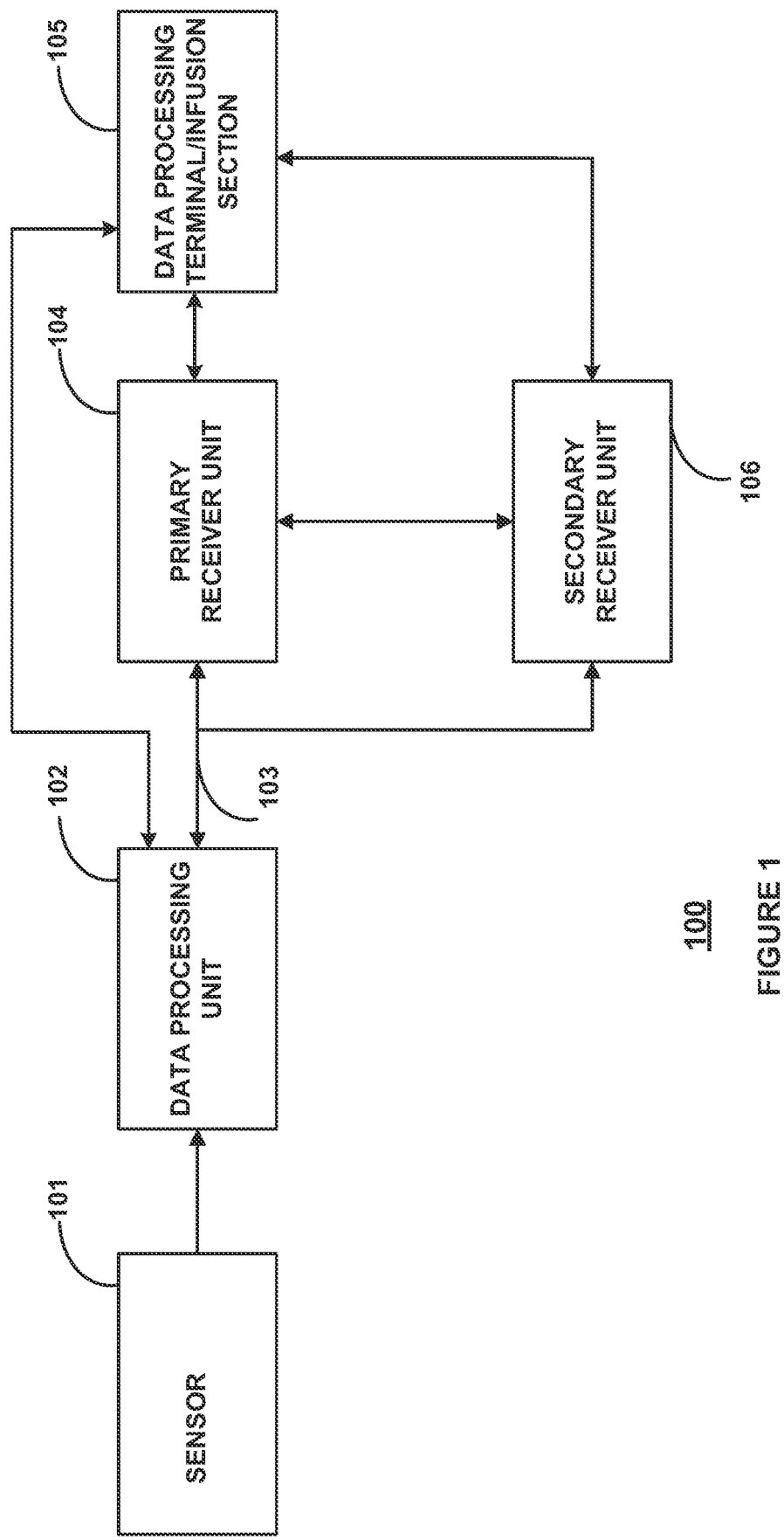
FIG. 1 shows a block diagram of an embodiment of a data monitoring and management system according to the present disclosure.

The following patents, applications and/or publications are incorporated herein by reference for all purposes: U.S. Pat. Nos. 5,262,035; 5,262,305; 5,264,104; 5,320,715; 5,543,326; 5,593,852; 6,103,033; 6,120,676; 6,134,461; 6,175,752; 6,284,478; 6,560,471; 6,579,690; 6,591,125; 6,605,200; 6,605,201; 6,650,471; 6,654,625; 6,676,819; 6,746,582; 6,881,551; 6,932,892; 6,932,894; 7,299,082; U.S. Published Patent Application Nos. 2004/0186365, now U.S. Pat. No. 7,811,231; 2005/0182306, now U.S. Pat. No. 8,771,183; 2007/0056858, now U.S. Pat. No. 8,298,389; 2007/0068807, now U.S. Pat. No. 7,846,311; 2007/0227911, now U.S. Pat. No. 7,887,682; 2007/0233013; 2008/0081977, now U.S. Pat. No. 7,618,369; 2008/0161666; and 2009/0054748, now U.S. Pat. No. 7,885,698; U.S. patent application Ser. No. 12/131,012; Ser. No. 12/242,823, now U.S. Pat. No. 8,219,173; and Ser. No. 12/363,712, now U.S. Pat. No. 8,346,335; and U.S. Provisional Application Nos. 61/149,639; 61/155,889; 61/155,891; 61/155,893; 61/165,499; 61/230,686; 61/227,967 and 61/238,461.

DETAILED DESCRIPTION

Before the present disclosure is described, it is to be understood that this disclosure is not limited to particular embodiments described, as such may, of course, vary. It is also to be understood that the terminology used herein is for the purpose of describing particular embodiments only, and is not intended to be limiting, since the scope of the present disclosure will be limited only by the appended claims.

Where a range of values is provided, it is understood that each intervening value, to the tenth of the unit of the lower limit unless the context clearly dictates otherwise, between the upper and lower limit of that range and any other stated or intervening value in that stated range, is encompassed within the disclosure. The upper and lower limits of these smaller ranges may independently be included in the smaller ranges as also encompassed within the disclosure, subject to any specifically excluded limit in the stated range. Where the stated range includes one or both of the limits, ranges excluding either or both of those included limits are also included in the disclosure.

It must be noted that as used herein and in the appended claims, the singular forms "a", "an", and "the" include plural referents unless the context clearly dictates otherwise.

As will be apparent to those of skill in the art upon reading this disclosure, each of the individual embodiments described and illustrated herein has discrete components and features which may be readily separated from or combined with the features of any of the other several embodiments without departing from the scope or spirit of the present disclosure.

The figures shown herein are not necessarily drawn to scale, with some components and features being exaggerated for clarity.

Generally, embodiments of the present disclosure relate to methods and devices for detecting at least one analyte such as glucose in body fluid. Embodiments relate to the continuous and/or automatic in vivo monitoring of the level of one or more analytes using a continuous analyte monitoring system that includes an analyte sensor at least a portion of which is to be positioned beneath a skin surface of a user for a period of time and/or the discrete monitoring of one or more analytes using an in vitro blood glucose ("BG") meter and an analyte test strip. Embodiments include combined or combinable devices, systems and methods and/or transferring data between an in vivo continuous system and a BG meter system.

Accordingly, embodiments include analyte monitoring devices and systems that include an analyte sensor—at least a portion of which is positionable beneath the skin of the user—for the in vivo detection, of an analyte, such as glucose, lactate, and the like, in a body fluid. Embodiments include wholly implantable analyte sensors and analyte sensors in which only a portion of the sensor is positioned under the skin and a portion of the sensor resides above the skin, e.g., for contact to a transmitter, receiver, transceiver, processor, etc. The sensor may be, for example, subcutaneously positionable in a patient for the continuous or periodic monitoring of a level of an analyte in a patient's interstitial fluid. For the purposes of this description, continuous monitoring and periodic monitoring will be used interchangeably, unless noted otherwise. The sensor response may be correlated and/or converted to analyte levels in blood or other fluids. In certain embodiments, an analyte sensor may be positioned in contact with interstitial fluid to detect the level of glucose, in which detected glucose may be used to infer the glucose level in the patient's bloodstream. Analyte sensors may be insertable into a vein, artery, or other portion of the body containing fluid. Embodiments of the analyte sensors of the subject disclosure may be configured for monitoring the level of the analyte over a time period which may range from minutes, hours, days, weeks, or longer.

Of interest are analyte sensors, such as glucose sensors, that are capable of in vivo detection of an analyte for about one hour or more, e.g., about a few hours or more, e.g., about a few days of more, e.g., about three or more days, e.g., about five days or more, e.g., about seven days or more, e.g., about several weeks or at least one month. Future analyte levels may be predicted based on information obtained, e.g., the current analyte level at time to, the rate of change of the analyte, etc. Predictive alarms may notify the user of a predicted analyte level that may be of concern in advance of the user's analyte level reaching the future level. This provides the user an opportunity to take corrective action.

FIG. 1 shows a data monitoring and management system such as, for example, an analyte (e.g., glucose) monitoring system 100 in accordance with certain embodiments. Embodiments of the subject disclosure are further described primarily with respect to glucose monitoring devices and systems, and methods of glucose detection, for convenience only and such description is in no way intended to limit the scope of the disclosure. It is to be understood that the analyte monitoring system may be configured to monitor a variety of analytes at the same time or at different times.

Analytes that may be monitored include, but are not limited to, acetyl choline, amylase, bilirubin, cholesterol, chorionic gonadotropin, creatine kinase (e.g., CK-MB), creatine, creatinine, DNA, fructosamine, glucose, glutamine, growth hormones, hormones, ketone bodies, lactate, peroxide, prostate-specific antigen, prothrombin, RNA, thyroid stimulating hormone, and troponin. The concentration of drugs, such as, for example, antibiotics (e.g., gentamicin, vancomycin, and the like), digitoxin, digoxin, drugs of abuse, theophylline, and warfarin, may also be monitored. In those embodiments that monitor more than one analyte, the analytes may be monitored at the same or different times.

The analyte monitoring system 100 includes a sensor 101, a data processing unit 102 connectable to sensor 101, and a primary receiver unit 104 which is configured to communicate with data processing unit 102 via a communication link 103. In certain embodiments, primary receiver unit 104 may be further configured to transmit data to a data processing terminal 105 to evaluate or otherwise process or format data received by primary receiver unit 104. Data processing terminal 105 may be configured to receive data directly from data processing unit 102 via a communication link which may optionally be configured for bi-directional communication. Further, data processing unit 102 may include a transmitter or a transceiver to transmit and/or receive data to and/or from primary receiver unit 104 and/or data processing terminal 105 and/or optionally the secondary receiver unit 106.

Also shown in FIG. 1 is an optional secondary receiver unit 106 which is operatively coupled to the communication link and configured to receive data transmitted from data processing unit 102. The secondary receiver unit 106 may be configured to communicate with primary receiver unit 104, as well as data processing terminal 105. The secondary receiver unit 106 may be configured for bi-directional wireless communication with each of primary receiver unit 104 and data processing terminal 105. As discussed in further detail below, in certain embodiments the secondary receiver unit 106 may be a de-featured receiver as compared to the primary receiver, i.e., the secondary receiver may include a limited or minimal number of functions and features as compared with primary receiver unit 104. As such, the secondary receiver unit 106 may include a smaller (in one or more, including all, dimensions), compact housing or embodied in a device such as a wrist watch, arm band, etc., for example. Alternatively, the secondary receiver unit 106 may be configured with the same or substantially similar functions and features as primary receiver unit 104. The secondary receiver unit 106 may include a docking portion to be mated with a docking cradle unit for placement by, e.g., the bedside for night time monitoring, and/or a bi-directional communication device. A docking cradle may recharge a powers supply.

Only one sensor 101, data processing unit 102 and data processing terminal 105 are shown in the embodiment of the analyte monitoring system 100 illustrated in FIG. 1. However, it will be appreciated by one of ordinary skill in the art that the analyte monitoring system 100 may include more than one sensor 101 and/or more than one data processing unit 102, and/or more than one data processing terminal 105. Multiple sensors may be positioned in a patient for analyte monitoring at the same or different times. In certain embodiments, analyte information obtained by a first positioned sensor may be employed as a comparison to analyte information obtained by a second sensor. This may be useful to confirm or validate analyte information obtained from one or both of the sensors. Such redundancy may be useful if analyte information is contemplated in critical therapy-related decisions. In certain embodiments, a first sensor may be used to calibrate a second sensor.

The analyte monitoring system 100 may be a continuous monitoring system, or semi-continuous, or a discrete monitoring system. In a multi-component environment, each component may be configured to be uniquely identified by one or more of the other components in the system so that communication conflict may be readily resolved between the various components within the analyte monitoring system 100. For example, unique IDs, communication channels, and the like, may be used.

In certain embodiments, sensor 101 is physically positioned in or on the body of a user whose analyte level is being monitored. Sensor 101 may be configured to at least periodically sample the analyte level of the user and convert the sampled analyte level into a corresponding signal for transmission by data processing unit 102. Data processing unit 102 is coupleable to sensor 101 so that both devices are positioned in or on the user's body, with at least a portion of the analyte sensor 101 positioned transcutaneously. The data processing unit may include a fixation element such as adhesive or the like to secure it to the user's body. A mount (not shown) attachable to the user and mateable with data processing unit 102 may be used. For example, a mount may include an adhesive surface. Data processing unit 102 performs data processing functions, where such functions may include but are not limited to, filtering and encoding of data signals, each of which corresponds to a sampled analyte level of the user, for transmission to primary receiver unit 104 via the communication link 103. In one embodiment, sensor 101 or data processing unit 102 or a combined sensor/data processing unit may be wholly implantable under the skin layer of the user.

In certain embodiments, primary receiver unit 104 may include an analog interface section including an RF receiver and an antenna that is configured to communicate with data processing unit 102 via the communication link 103, and a data processing section for processing the received data from data processing unit 102 such as data decoding, error detection and correction, data clock generation, data bit recovery, etc., or any combination thereof.

In operation, primary receiver unit 104 in certain embodiments is configured to synchronize with data processing unit 102 to uniquely identify data processing unit 102, based on, for example, an identification information of data processing unit 102, and thereafter, to periodically receive signals transmitted from data processing unit 102 associated with the monitored analyte levels detected by sensor 101.

Referring again to FIG. 1, data processing terminal 105 may include a personal computer, a portable computer such as a laptop or a handheld device (e.g., personal digital assistants (PDAs), telephone such as a cellular phone (e.g., a multimedia and Internet-enabled mobile phone such as an iPhone or similar phone), mp3 player, pager, and the like), drug delivery device, each of which may be configured for data communication with the receiver via a wired or a wireless connection. Additionally, data processing terminal 105 may further be connected to a data network (not shown) for storing, retrieving, updating, and/or analyzing data corresponding to the detected analyte level of the user.

In certain embodiments, data processing terminal 105 may include an infusion device such as an insulin infusion pump or the like, which may be configured to administer insulin to patients, and which may be configured to communicate with primary receiver unit 104 for receiving, among others, the measured analyte level. Alternatively, primary receiver unit 104 may be configured to integrate an infusion device therein so that primary receiver unit 104 is configured to administer insulin (or other appropriate drug) therapy to patients, for example, for administering and modifying basal profiles, as well as for determining appropriate boluses for administration based on, among others, the detected analyte levels received from data processing unit 102. An infusion device may be an external device or an internal device (wholly implantable in a user).

In certain embodiments, data processing terminal 105, which may include an insulin pump, may be configured to receive the analyte signals from data processing unit 102, and thus, incorporate the functions of primary receiver unit 104 including data processing for managing the patient's insulin therapy and analyte monitoring. In certain embodiments, the communication link 103 as well as one or more of the other communication interfaces shown in FIG. 1, may use one or more of: an RF communication protocol, an infrared communication protocol, a Bluetooth® enabled communication protocol, an 802.11x wireless communication protocol, or an equivalent wireless communication protocol which would allow secure, wireless communication of several units (for example, per HIPAA requirements), while avoiding potential data collision and interference.

Figure 2:
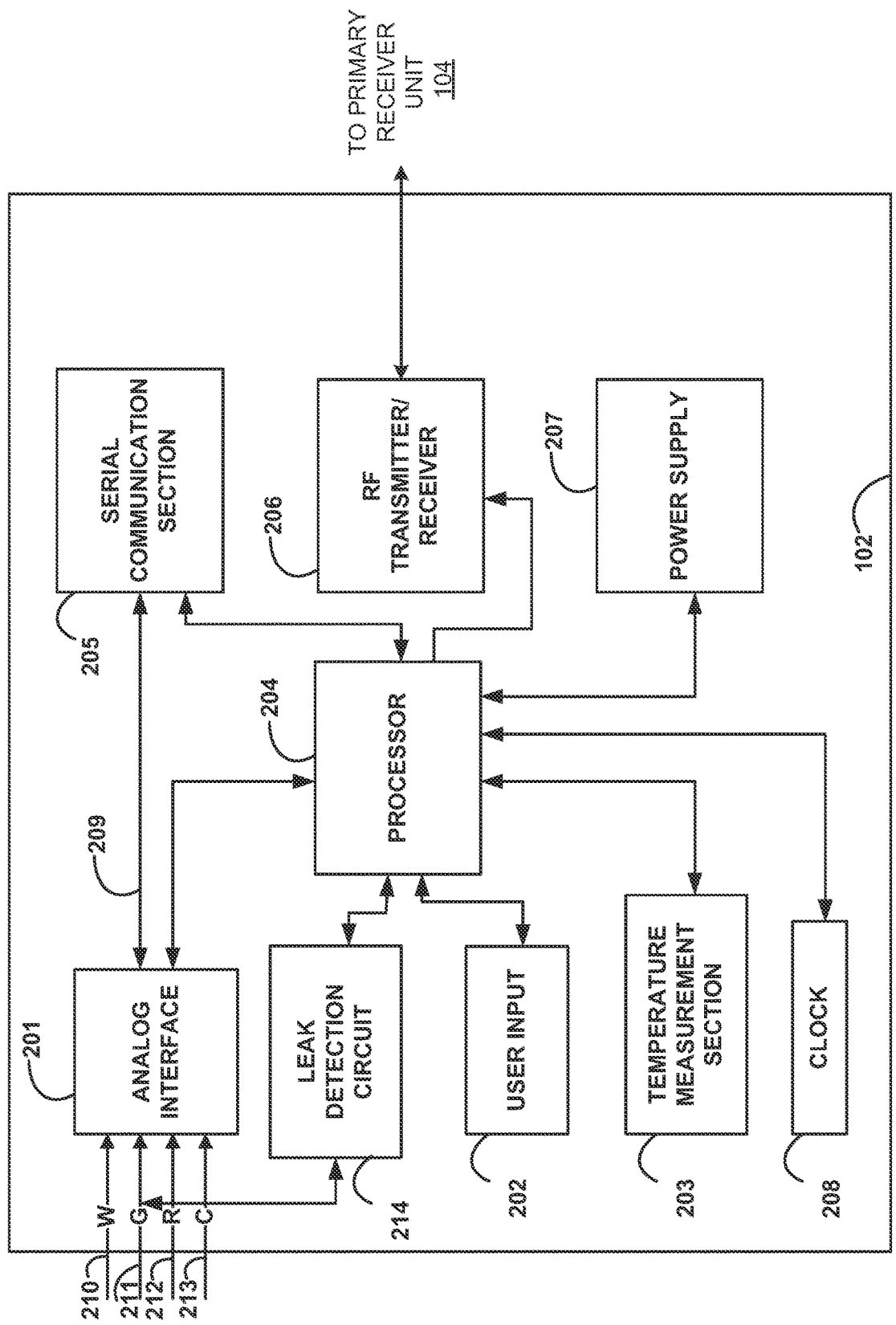
FIG. 2 shows a block diagram of an embodiment of the transmitter unit of the data monitoring and management system of FIG. 1.

FIG. 2 shows a block diagram of an embodiment of a data processing unit of the data monitoring and detection system shown in FIG. 1. User input and/or interface components may be included or a data processing unit may be free of user input and/or interface components. In certain embodiments, one or more ASICs may be used to implement one or more functions or routines associated with the operations of the data processing unit (and/or receiver unit) using for example one or more state machines and buffers. Referring to the Figure, the data processing unit 102 in one embodiment includes an analog interface 201 configured to communicate with the sensor 101 (FIG. 1), a user input 202, and a temperature measurement section 203, each of which is operatively coupled to a processor 204 such as a central processing unit (CPU).

As can be seen in the embodiment of FIG. 2, the sensor 101 (FIG. 1) includes four contacts, three of which are electrodes—work electrode (W) 210, reference electrode (R) 212, and counter electrode (C) 213, each operatively coupled to the analog interface 201 of data processing unit 102. This embodiment also shows optional guard contact (G) 211. Fewer or greater electrodes may be employed. For example, the counter and reference electrode functions may be served by a single counter/reference electrode, there may be more than one working electrode and/or reference electrode and/or counter electrode, etc.

The electronics of the on-skin sensor control unit and the sensor are operated using a power supply 207, e.g., a battery. Additionally, as can be seen from the Figure, clock 208 is provided to, among others, supply real time information to the processor 204.

In one aspect, the analog interface 201 is coupled via the conductive contacts of data processing unit 102 to one or more sensors 101. The analog interface 201 in one embodiment is configured to receive signals from and to operate the sensor(s). For example, in one embodiment, the analyte interface 201 may obtain signals from sensor 101 (FIG. 1) using amperometric, coulometric, potentiometric, voltammetric, and/or other electrochemical techniques. For example, to obtain amperometric measurements, the analog interface 201 includes a potentiostat that provides a constant potential to sensor 101. In other embodiments, the analog interface 201 includes an amperostat that supplies a constant current to a sensor and can be used to obtain coulometric or potentiometric measurements.

The signal from the sensor 101 (FIG. 1) generally has at least one characteristic, such as, for example, current, voltage, or frequency, or the like, which varies with the concentration of the analyte that the sensor 101 is monitoring. For example, if the analog interface 201 operates using amperometry, then the current signal from the sensor varies with variation in the monitored analyte concentration. Referring back to FIG. 2, one or more of the components of data processing unit 102, including, for example, the processor 204, the analog interface 201, and/or the RF transmitter/receiver 206 may include circuitry which converts the information-carrying portion of the signal from one characteristic to another. For example, the one or more components of data processing unit 102 such as the processor 204, the analyte interface 201, and/or the RF transmitter/receiver 206 may include a current-to-voltage or current-to-frequency converter. In one aspect, the converter may be configured to provide a signal that is, for example, more easily transmitted, readable by digital circuits, and/or less susceptible to noise contributions. In one embodiment, a unidirectional input path is established from the sensor 101 (FIG. 1) and/or manufacturing and testing equipment to the analog interface 201 of the data processing unit 102, while a unidirectional output is established from the output of the RF transmitter 206 of the data processing unit 102 for transmission to the primary receiver unit 104. In this manner, a data path is shown in FIG. 2 between the aforementioned unidirectional input and output via a dedicated link 209 from the analog interface 201 to serial communication section 205, thereafter to the processor 204, and then to the RF transmitter 206. Also shown is a leak detection circuit 214 coupled to the guard contact (G) 211 and the processor 204 in the data processing unit 102. The leak detection circuit 214 in accordance with one embodiment of the present invention may be configured to detect leakage current in the sensor 101 to determine whether the measured sensor data are corrupt or whether the measured data from the sensor 101 is accurate.

Figure 3A:
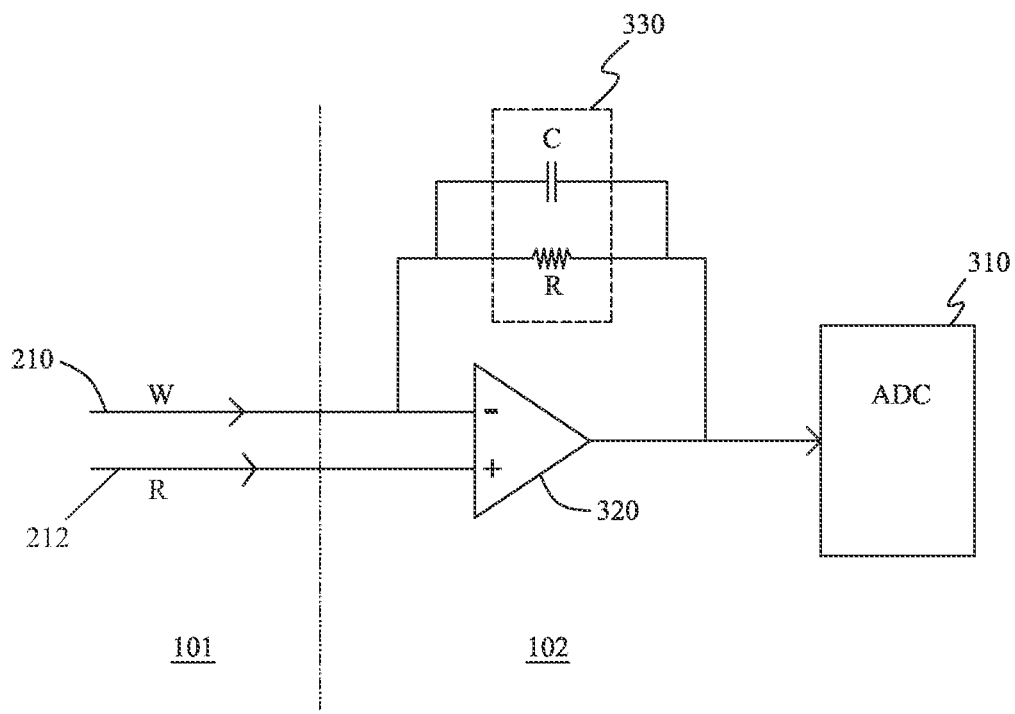
FIGS. 3A and 3B illustrate the sensor/transmitter interface including the analog interface section of the data processing unit 102 of FIG. 2 in one embodiment of the present disclosure.
Figure 3B:
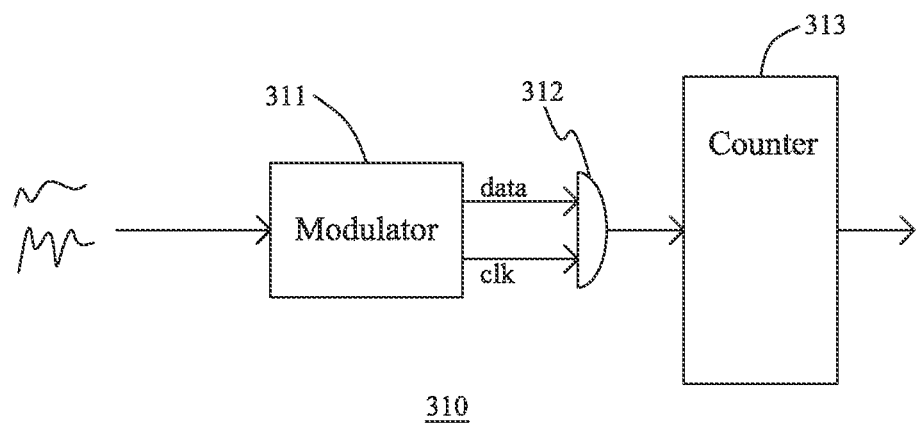

Referring now to FIGS. 3A and 3B, the sensor interface electronics including the analog interface section of the data processing unit 102 (FIG. 1). More specifically, referring to FIG. 3A, there is provided an analog to digital converter (ADC) 310 which is configured to receive the filtered output analog signal of the operational amplifier 320 which has one of its input terminals (negative input terminal as shown, for example) operatively coupled to the working electrode W 210 of sensor 101 (FIG. 1). As described, in one aspect, the operational amplifier 320 is configured to maintain the voltage level at the working electrode W 210 at approximately two volts while the reference electrode R 212 (FIG. 2) of the sensor (FIG. 1) is operatively coupled to the positive input terminal of the operational amplifier 320 and maintained at approximately 1.96 Volts, so that a difference of approximately 40 mVolts is maintained as the poise voltage to power the sensor electrodes.

Referring back to FIG. 3A, the filter 330 operatively coupled between the negative input terminal and the output terminal of the operational amplifier 320, is configured to filter the received signal from the sensor electrodes to remove or filter out the signal transients. Signal artifacts may be limited to a predetermined signal bandwidth (for example, to approximately 0.1 Hz) effectively operating as a bandpass filter prior to providing the signal to the analog to digital converter ADC 310 for further processing.

In one embodiment, the resistor R of the filter 330 has a resistance value of approximately 1.58 MOhms, while the capacitor C has a capacitance of approximately one microFarad. While specific values are provided herein, it is to be noted that these values for the various components of the filter as well as the operational amplifier are for exemplary purposes only, and are not intended to limit the scope of the embodiments of the present disclosure to such particular values or parameters. Within the scope of the present disclosure, other values or parameters are contemplated for example, for the resistor R and the capacitor C of the filter 330, as well as the operational amplifier 320.

Referring still to FIG. 3A, the filtered output signal from the operational amplifier 320 in the form of an analog voltage signal is provided to the analog to digital converter 310 for further processing as described herein. That is, referring now to FIG. 3B, a detailed description of a portion of the ADC 310 is shown. More specifically, as shown in FIG. 3B, the ADC 310 includes, among others, a signal modulator 311 operatively coupled to the input of the ADC 310 to receive the voltage signal from the output of the operational amplifier 320 (FIG. 3A). The signal modulator in one embodiment may include a Sigma-Delta modulator. A Sigma-Delta modulator, in certain embodiments, allows for high resolution analog-to-digital conversion achievable utilizing low cost circuits. In other embodiments, different or modified modulators with similar or equivalent functionality may be provided including, for example, converters, filters, and/or signal processing devices and components.

In one aspect, the modulator 311 is configured to modulate the received analog voltage signal from the output of the operational amplifier 320 to generate a corresponding frequency data stream which is synchronized with one or more clock signals. That is, referring to FIG. 3B, in one aspect, the modulator 311 is configured to convert the received voltage signal which may vary between, for example, 1.5 Volts to 2.0 Volts, into a corresponding frequency data stream. In one aspect, the modulator 311 includes a servo loop and the output of the modulator 311 includes the converted or modulated frequency data stream and the corresponding clock signal.

Referring again to FIG. 3B, AND gate 312 is shown and provided to the ADC 310, and is configured to receive the frequency data stream (shown as "data" in FIG. 3B) and the clock signal (shown as "clk" in FIG. 3B) and perform an AND function to synchronize the received frequency data with the clock signal to generate a corresponding frequency pulse to provide to a counter 313. That is, as shown in FIG. 3B, the output terminal of the AND gate 312 is operatively coupled to the counter 313, and the counter 313, in one embodiment, is configured to count the pulses received from the AND gate 312. In some embodiments, the analog to digital conversion is conducted quickly, in order to obtain a converted signal for a specific point in time. In order for the analog to digital conversion to be achieved substantially immediately, a high frequency clock signal is used, such that the counted pulses of the conversion occur in rapid succession.

In other embodiments, a lower frequency clock, for example a 1024 Hz clock signal, may be implemented and the analog to digital conversion is spread out over a predetermined or programmed time period, such as, for example, a 30 second (or other suitable or appropriate) time period or other suitable measurement time period. In one aspect, the counter 313 is configured to receive the synchronized frequency data stream or pulses from the AND gate 312 and counts the received pulses over the predetermined time period to generate an average accumulated count, that is representative of the average data associated with the signal from sensor 101 (FIG. 1) over the time period.

In one aspect, the clock signal used to synchronize the data stream from the modulator 311 is a 1024 Hz signal. Furthermore, in one embodiment, the AND gate 312 operates such that the pulse from the modulator 311 is received by the counter 313 when the clock signal is a "1" (as opposed to a "0"). In this manner, in one aspect, the counter 313 is initially set to a zero count, and thereafter, when the predetermined measurement time period has elapsed (for example, the 30 second time period), the counter 313 has accumulated pulses during this time duration to output an average value of the accumulated pulses received from the time duration as the corresponding sensor data processed from the voltage signal received from the working electrode 210 (FIG. 2) of sensor 101 (FIG. 1).

In this manner, in one aspect, lower power consumption of the data processing unit 102 (FIG. 1) may be achieved, in addition to improving processed analyte signal resolution as well as providing a built-in filtering function to filter out signal transients and/or noise associated with the received signals. That is, given that the counter is configured to accumulate the pulses over an extended measurement time period such as 30 seconds or other suitable time period, and given that the determined or programmed time period defines the filter frequency response, by customizing or tailoring the time period to a particular sensor or sensors, the frequency response associated with the sensor may be improved. Moreover, the predetermined or programmed time period provides a time duration which allows the use of low frequency modulator clock (e.g., 1024 Hz) which consumes less power, and thus, extends the power supply life of the data processing unit 102 (FIG. 1).

Referring still again to FIGS. 3A and 3B, in the manner described above, in aspects of the present disclosure, an extended measurement time period is provided based on, for example, the predetermined or programmed time period to sample or accumulate the pulses or data stream received from analyte sensor 101, and that is determined by or is a function of the clock discussed above in conjunction with the modulator and configured to establish the maximum resolution as a function of the conversion (analog to digital) time. In this manner, in one aspect, an extended sampling time period (as compared to a discrete signal sampling) is provided to extend the signal conversion process over a longer measurement time period resulting in improved power consumption management, higher signal resolution and noise or artifact filtered analyte signals for further processing, including transmission to a remote device or location for presentation or output to the user or patient.

Accumulating or averaging the received frequency data stream or pulses from analyte sensor 101 results in a frequency domain filter function that rolls off at a frequency equal to the reciprocal of the signal conversion time. Thus, any frequency or components of the data stream that is a multiple of the signal conversion time is rejected, filtering out undesirable signal artifacts, among others. Additionally, given that common signal frequency interference occurs at the power line frequencies of 50 and 60 Hz, and multiples thereof, by modifying or adjusting the conversion time duration to be a division of the common interference frequencies, the filter function is configured to remove these frequency signals.

Additionally, as discussed above, the embodiments described above provides low power consumption by providing a slow modulator clock while retaining the desired high signal resolution, as the slow clock consumes a low amount of power such that, using 1024 Hz clock with a 30 second conversion time period, a 15 bit signal resolution may be attained. In aspects of the present disclosure, the clock function of the modulator 311 may be a divided down clock as described above, divided down from a 32.768 KHz crystal to the 1024 Hz clock.

Referring back to FIGS. 3A and 3B, the converted analyte related signal from the output of the ADC 310 is further processed for storage, additional filtering, and data packing, encoding and the like for wireless transmission, for example to the receiver/monitor unit 104, as well as other data processing routines described herein.

Figure 4:
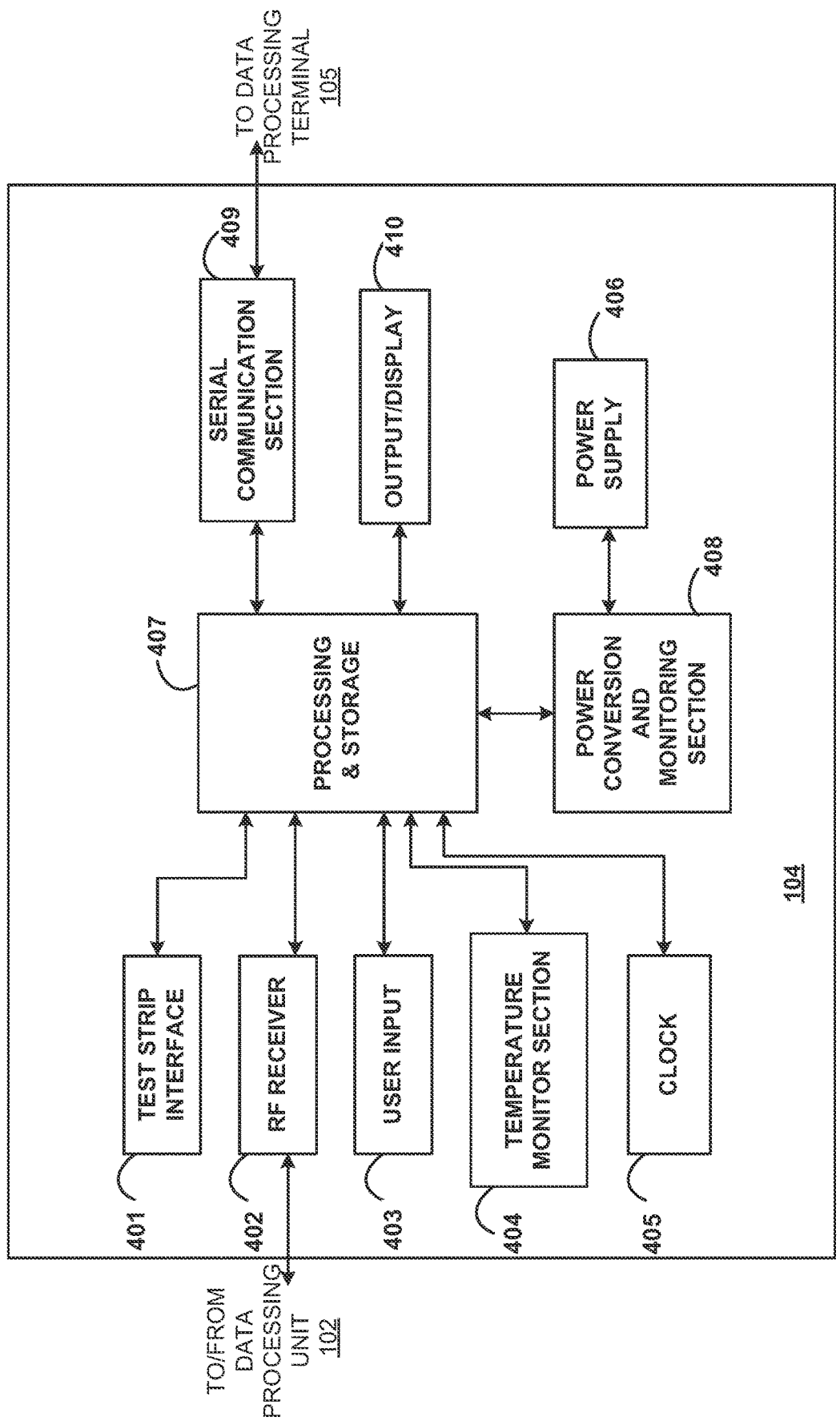
FIG. 4 shows a block diagram of an embodiment of the receiver/monitor unit of the data monitoring and management system of FIG. 1.

FIG. 4 is a block diagram of an embodiment of a receiver/monitor unit such as primary receiver unit 104 of the data monitoring and management system shown in FIG. 1. In certain embodiments, primary receiver unit 104 includes one or more of: a blood glucose test strip interface 401, an RF receiver 402, a user input 403, a temperature monitor section 404, and a clock 405, each of which is operatively coupled to a processing and storage section 407. Primary receiver unit 104 also includes a power supply 406 operatively coupled to a power conversion and monitoring section 408. Further, the power conversion and monitoring section 408 is also coupled to the receiver processing and storage section 407. Moreover, also shown are a receiver serial communication section 409, and an output 410, each operatively coupled to the processing and storage unit 407. The receiver may include user input and/or interface components or may be free of user input and/or interface components.

In certain embodiments, the test strip interface 401 includes a glucose level testing portion to receive a blood (or other body fluid sample) glucose test or information related thereto. For example, the interface may include a test strip port to receive a glucose test strip. The device may determine the glucose level of the test strip, and optionally display (or otherwise notice) the glucose level on the output 410 of primary receiver unit 104. Any suitable test strip may be employed, e.g., test strips that only require a very small amount (e.g., one microliter or less, e.g., 0.5 microliter or less, e.g., 0.1 microliter or less), of applied sample to the strip in order to obtain accurate glucose information, e.g. FreeStyle® blood glucose test strips from Abbott Diabetes Care Inc. Glucose information obtained by the in vitro glucose testing device may be used for a variety of purposes, computations, etc. For example, the information may be used to calibrate sensor 101, confirm results of sensor 101 to increase the confidence thereof (e.g., in instances in which information obtained by sensor 101 is employed in therapy related decisions), etc.

In further embodiments, data processing unit 102 and/or primary receiver unit 104 and/or the secondary receiver unit 106, and/or the data processing terminal/infusion section 105 may be configured to receive the blood glucose value wirelessly over a communication link from, for example, a blood glucose meter. In further embodiments, a user manipulating or using the analyte monitoring system 100 (FIG. 1) may manually input the blood glucose value using, for example, a user interface (for example, a keyboard, keypad, voice commands, and the like) incorporated in the one or more of data processing unit 102, primary receiver unit 104, secondary receiver unit 106, or the data processing terminal/infusion section 105.

FIG. 5 schematically shows an embodiment of an analyte sensor in accordance with the present disclosure. This sensor embodiment includes electrodes 501, 502 and 503 on a base 504. Electrodes (and/or other features) may be applied or otherwise processed using any suitable technology, e.g., chemical vapor deposition (CVD), physical vapor deposition, sputtering, reactive sputtering, photolithography, printing, coating, ablating (e.g., laser ablation), painting, dip coating, etching, and the like. Materials include but are not limited to aluminum, carbon (such as graphite), cobalt, copper, gallium, gold, indium, iridium, iron, lead, magnesium, mercury (as an amalgam), nickel, niobium, osmium, palladium, platinum, rhenium, rhodium, selenium, silicon (e.g., doped polycrystalline silicon), silver, tantalum, tin, titanium, tungsten, uranium, vanadium, zinc, zirconium, mixtures thereof, and alloys, oxides, or metallic compounds of these elements.

The sensor may be wholly implantable in a user or may be configured so that only a portion is positioned within (internal) a user and another portion outside (external) a user. For example, the sensor 500 may include a portion positionable above a surface of the skin 510, and a portion positioned below the skin. In such embodiments, the external portion may include contacts (connected to respective electrodes of the second portion by traces) to connect to another device also external to the user such as a transmitter unit. While the embodiment of FIG. 5 shows three electrodes side-by-side on the same surface of base 504, other configurations are contemplated, e.g., fewer or greater electrodes, some or all electrodes on different surfaces of the base or present on another base, some or all electrodes stacked together, electrodes of differing materials and dimensions, etc.

FIG. 6A shows a perspective view of an embodiment of an electrochemical analyte sensor 600 having a first portion (which in this embodiment may be characterized as a major portion) positionable above a surface of the skin 610, and a second portion (which in this embodiment may be characterized as a minor portion) that includes an insertion tip 630 positionable below the skin, e.g., penetrating through the skin and into, e.g., the subcutaneous space 620, in contact with the user's biofluid such as interstitial fluid. Contact portions of a working electrode 601, a reference electrode 602, and a counter electrode 603 are positioned on the portion of the sensor 600 situated above the skin surface 610. Working electrode 601, a reference electrode 602, and a counter electrode 603 are shown at the second section and particularly at the insertion tip 630. Traces may be provided from the electrode at the tip to the contact, as shown in FIG. 6A. It is to be understood that greater or fewer electrodes may be provided on a sensor. For example, a sensor may include more than one working electrode and/or the counter and reference electrodes may be a single counter/reference electrode, etc.

FIG. 6B shows a cross sectional view of a portion of the sensor 600 of FIG. 6A. The electrodes 601, 602 and 603, of the sensor 600 as well as the substrate and the dielectric layers are provided in a layered configuration or construction. For example, as shown in FIG. 6B, in one aspect, the sensor 600 (such as the sensor 101 FIG. 1), includes a substrate layer 604, and a first conducting layer 601 such as carbon, gold, etc., disposed on at least a portion of the substrate layer 604, and which may provide the working electrode. Also shown disposed on at least a portion of the first conducting layer 601 is a sensing layer 608.

A first insulation layer such as a first dielectric layer 605 is disposed or layered on at least a portion of the first conducting layer 601, and further, a second conducting layer 609 may be disposed or stacked on top of at least a portion of the first insulation layer (or dielectric layer) 605. As shown in FIG. 6B, the second conducting layer 609 may provide the reference electrode 602, and in one aspect, may include a layer of silver/silver chloride (Ag/AgCl), gold, etc.

A second insulation layer 606 such as a dielectric layer in one embodiment may be disposed or layered on at least a portion of the second conducting layer 609. Further, a third conducting layer 603 may provide the counter electrode 603. It may be disposed on at least a portion of the second insulation layer 606. Finally, a third insulation layer 607 may be disposed or layered on at least a portion of the third conducting layer 603. In this manner, the sensor 600 may be layered such that at least a portion of each of the conducting layers is separated by a respective insulation layer (for example, a dielectric layer). The embodiment of FIGS. 6A and 6B show the layers having different lengths. Some or all of the layers may have the same or different lengths and/or widths.

In certain embodiments, some or all of the electrodes 601, 602, 603 may be provided on the same side of the substrate 604 in the layered construction as described above, or alternatively, may be provided in a co-planar manner such that two or more electrodes may be positioned on the same plane (e.g., side-by side (e.g., parallel) or angled relative to each other) on the substrate 604. For example, co-planar electrodes may include a suitable spacing there between and/or include dielectric material or insulation material disposed between the conducting layers/electrodes. Furthermore, in certain embodiments one or more of the electrodes 601, 602, 603 may be disposed on opposing sides of the substrate 604. In such embodiments, contact pads may be on the same or different sides of the substrate. For example, an electrode may be on a first side and its respective contact may be on a second side, e.g., a trace connecting the electrode and the contact may traverse through the substrate.

As noted above, analyte sensors may include an analyte-responsive enzyme to provide a sensing component or sensing layer. Some analytes, such as oxygen, can be directly electrooxidized or electroreduced on a sensor, and more specifically at least on a working electrode of a sensor. Other analytes, such as glucose and lactate, require the presence of at least one electron transfer agent and/or at least one catalyst to facilitate the electrooxidation or electroreduction of the analyte. Catalysts may also be used for those analytes, such as oxygen, that can be directly electrooxidized or electroreduced on the working electrode. For these analytes, each working electrode includes a sensing layer (see for example sensing layer 608 of FIG. 6B) proximate to or on a surface of a working electrode. In many embodiments, a sensing layer is formed near or on only a small portion of at least a working electrode.

The sensing layer includes one or more components designed to facilitate the electrochemical oxidation or reduction of the analyte. The sensing layer may include, for example, a catalyst to catalyze a reaction of the analyte and produce a response at the working electrode, an electron transfer agent to transfer electrons between the analyte and the working electrode (or other component), or both.

A variety of different sensing layer configurations may be used. In certain embodiments, the sensing layer is deposited on the conductive material of a working electrode. The sensing layer may extend beyond the conductive material of the working electrode. In some cases, the sensing layer may also extend over other electrodes, e.g., over the counter electrode and/or reference electrode (or counter/reference is provided).

A sensing layer that is not in direct contact with the working electrode may include a catalyst that facilitates a reaction of the analyte. However, such sensing layers may include an electron transfer agent that transfers electrons directly from the analyte to the working electrode, as the sensing layer is spaced apart from the working electrode. One example of this type of sensor is a glucose or lactate sensor which includes an enzyme (e.g., glucose oxidase, glucose dehydrogenase, lactate oxidase, and the like) in the sensing layer. The glucose or lactate may react with a second compound in the presence of the enzyme. The second compound may then be electrooxidized or electroreduced at the electrode. Changes in the signal at the electrode indicate changes in the level of the second compound in the fluid and are proportional to changes in glucose or lactate level and, thus, correlate to the analyte level.

In certain embodiments which include more than one working electrode, one or more of the working electrodes may not have a corresponding sensing layer, or may have a sensing layer which does not contain one or more components (e.g., an electron transfer agent and/or catalyst) needed to electrolyze the analyte. Thus, the signal at this working electrode may correspond to background signal which may be removed from the analyte signal obtained from one or more other working electrodes that are associated with fully-functional sensing layers by, for example, subtracting the signal.

In certain embodiments, the sensing layer includes one or more electron transfer agents. Electron transfer agents that may be employed are electroreducible and electrooxidizable ions or molecules having redox potentials that are a few hundred millivolts above or below the redox potential of the standard calomel electrode (SCE). The electron transfer agent may be organic, organometallic, or inorganic. Examples of organic redox species are quinones and species that in their oxidized state have quinoid structures, such as Nile blue and indophenol. Examples of organometallic redox species are metallocenes such as ferrocene. Examples of inorganic redox species are hexacyanoferrate (III), ruthenium hexamine etc.

In certain embodiments, electron transfer agents have structures or charges which prevent or substantially reduce the diffusional loss of the electron transfer agent during the period of time that the sample is being analyzed. For example, electron transfer agents include but are not limited to a redox species, e.g., bound to a polymer which can in turn be disposed on or near the working electrode. The bond between the redox species and the polymer may be covalent, coordinative, or ionic. Although any organic, organometallic or inorganic redox species may be bound to a polymer and used as an electron transfer agent, in certain embodiments the redox species is a transition metal compound or complex, e.g., osmium, ruthenium, iron, and cobalt compounds or complexes. It will be recognized that many redox species described for use with a polymeric component may also be used, without a polymeric component.

One type of polymeric electron transfer agent contains a redox species covalently bound in a polymeric composition. An example of this type of mediator is poly(vinylferrocene). Another type of electron transfer agent contains an ionically-bound redox species. This type of mediator may include a charged polymer coupled to an oppositely charged redox species. Examples of this type of mediator include a negatively charged polymer coupled to a positively charged redox species such as an osmium or ruthenium polypyridyl cation. Another example of an ionically-bound mediator is a positively charged polymer such as quaternized poly(4-vinyl pyridine) or poly(1-vinyl imidazole) coupled to a negatively charged redox species such as ferricyanide or ferrocyanide. In other embodiments, electron transfer agents include a redox species coordinatively bound to a polymer. For example, the mediator may be formed by coordination of an osmium or cobalt 2,2'-bipyridyl complex to poly(1-vinyl imidazole) or poly(4-vinyl pyridine).

Suitable electron transfer agents are osmium transition metal complexes with one or more ligands, each ligand having a nitrogen-containing heterocycle such as 2,2'-bipyridine, 1,10-phenanthroline, 1-methyl, 2-pyridyl biimidazole, or derivatives thereof. The electron transfer agents may also have one or more ligands covalently bound in a polymer, each ligand having at least one nitrogen-containing heterocycle, such as pyridine, imidazole, or derivatives thereof. One example of an electron transfer agent includes (a) a polymer or copolymer having pyridine or imidazole functional groups and (b) osmium cations complexed with two ligands, each ligand containing 2,2'-bipyridine, 1,10-phenanthroline, or derivatives thereof, the two ligands not necessarily being the same. Some derivatives of 2,2'-bipyridine for complexation with the osmium cation include but are not limited to 4,4'-dimethyl-2,2'-bipyridine and mono-, di-, and polyalkoxy-2,2'-bipyridines, such as 4,4'-dimethoxy-2,2'-bipyridine. Derivatives of 1,10-phenanthroline for complexation with the osmium cation include but are not limited to 4,7-dimethyl-1,10-phenanthroline and mono, di-, and polyalkoxy-1,10-phenanthrolines, such as 4,7-dimethoxy-1,10-phenanthroline. Polymers for complexation with the osmium cation include but are not limited to polymers and copolymers of poly(1-vinyl imidazole) (referred to as "PVI") and poly(4-vinyl pyridine) (referred to as "PVP"). Suitable copolymer substituents of poly(1-vinyl imidazole) include acrylonitrile, acrylamide, and substituted or quaternized N-vinyl imidazole, e.g., electron transfer agents with osmium complexed to a polymer or copolymer of poly(1-vinyl imidazole).

Embodiments may employ electron transfer agents having a redox potential ranging from about −200 mV to about +200 mV versus the standard calomel electrode (SCE). The sensing layer may also include a catalyst which is capable of catalyzing a reaction of the analyte. The catalyst may also, in some embodiments, act as an electron transfer agent. One example of a suitable catalyst is an enzyme which catalyzes a reaction of the analyte. For example, a catalyst, such as a glucose oxidase, glucose dehydrogenase (e.g., pyrroloquinoline quinone (PQQ), dependent glucose dehydrogenase, flavine adenine dinucleotide (FAD), or nicotinamide adenine dinucleotide (NAD) dependent glucose dehydrogenase), may be used when the analyte of interest is glucose. A lactate oxidase or lactate dehydrogenase may be used when the analyte of interest is lactate. Laccase may be used when the analyte of interest is oxygen or when oxygen is generated or consumed in response to a reaction of the analyte.

The sensing layer may also include a catalyst which is capable of catalyzing a reaction of the analyte. The catalyst may also, in some embodiments, act as an electron transfer agent. One example of a suitable catalyst is an enzyme which catalyzes a reaction of the analyte. For example, a catalyst, such as a glucose oxidase, glucose dehydrogenase (e.g., pyrroloquinoline quinone (PQQ), dependent glucose dehydrogenase or oligosaccharide dehydrogenase, flavine adenine dinucleotide (FAD) dependent glucose dehydrogenase, nicotinamide adenine dinucleotide (NAD) dependent glucose dehydrogenase), may be used when the analyte of interest is glucose. A lactate oxidase or lactate dehydrogenase may be used when the analyte of interest is lactate. Laccase may be used when the analyte of interest is oxygen or when oxygen is generated or consumed in response to a reaction of the analyte.

In certain embodiments, a catalyst may be attached to a polymer, cross linking the catalyst with another electron transfer agent (which, as described above, may be polymeric). A second catalyst may also be used in certain embodiments. This second catalyst may be used to catalyze a reaction of a product compound resulting from the catalyzed reaction of the analyte. The second catalyst may operate with an electron transfer agent to electrolyze the product compound to generate a signal at the working electrode. Alternatively, a second catalyst may be provided in an interferent-eliminating layer to catalyze reactions that remove interferents.

Certain embodiments include a Wired Enzyme™ sensing layer (Abbott Diabetes Care Inc.) that works at a gentle oxidizing potential, e.g., a potential of about +40 mV. This sensing layer uses an osmium (Os)—based mediator designed for low potential operation and is stably anchored in a polymeric layer. Accordingly, in certain embodiments the sensing element is a redox active component that includes (1) Osmium-based mediator molecules attached by stable (bidente) ligands anchored to a polymeric backbone, and (2) glucose oxidase enzyme molecules. These two constituents are crosslinked together.

A mass transport limiting layer (not shown), e.g., an analyte flux modulating layer, may be included with the sensor to act as a diffusion-limiting barrier to reduce the rate of mass transport of the analyte, for example, glucose or lactate, into the region around the working electrodes. The mass transport limiting layers are useful in limiting the flux of an analyte to a working electrode in an electrochemical sensor so that the sensor is linearly responsive over a large range of analyte concentrations and is easily calibrated. Mass transport limiting layers may include polymers and may be biocompatible. A mass transport limiting layer may provide many functions, e.g., biocompatibility and/or interferent-eliminating, etc.

In certain embodiments, a mass transport limiting layer is a membrane composed of crosslinked polymers containing heterocyclic nitrogen groups, such as polymers of polyvinylpyridine and polyvinylimidazole. Embodiments also include membranes that are made of a polyurethane, or polyether urethane, or chemically related material, or membranes that are made of silicone, and the like.

A membrane may be formed by crosslinking in situ a polymer, modified with a zwitterionic moiety, a non-pyridine copolymer component, and optionally another moiety that is either hydrophilic or hydrophobic, and/or has other desirable properties, in an alcohol-buffer solution. The modified polymer may be made from a precursor polymer containing heterocyclic nitrogen groups. For example, a precursor polymer may be polyvinylpyridine or polyvinylimidazole. Optionally, hydrophilic or hydrophobic modifiers may be used to "fine-tune" the permeability of the resulting membrane to an analyte of interest. Optional hydrophilic modifiers, such as poly(ethylene glycol), hydroxyl or polyhydroxyl modifiers, may be used to enhance the biocompatibility of the polymer or the resulting membrane.

A membrane may be formed in situ by applying an alcohol-buffer solution of a crosslinker and a modified polymer over an enzyme-containing sensing layer and allowing the solution to cure for about one to two days or other appropriate time period. The crosslinker-polymer solution may be applied to the sensing layer by placing a droplet or droplets of the solution on the sensor, by dipping the sensor into the solution, or the like. Generally, the thickness of the membrane is controlled by the concentration of the solution, by the number of droplets of the solution applied, by the number of times the sensor is dipped in the solution, or by any combination of these factors. A membrane applied in this manner may have any combination of the following functions: (1) mass transport limitation, i.e., reduction of the flux of analyte that can reach the sensing layer, (2) biocompatibility enhancement, or (3) interferent reduction.

The electrochemical sensors may employ any suitable measurement technique. For example, may detect current or may employ potentiometry. Technique may include, but are not limited to, amperometry, coulometry, and voltammetry. In some embodiments, sensing systems may be optical, colorimetric, and the like.

In certain embodiments, the sensing system detects hydrogen peroxide to infer glucose levels. For example, a hydrogen peroxide-detecting sensor may be constructed in which a sensing layer includes enzyme such as glucose oxides, glucose dehydrogensae, or the like, and is positioned proximate to the working electrode. The sensing layer may be covered by a membrane that is selectively permeable to glucose. Once the glucose passes through the membrane, it is oxidized by the enzyme and reduced glucose oxidase can then be oxidized by reacting with molecular oxygen to produce hydrogen peroxide.

Certain embodiments include a hydrogen peroxide-detecting sensor constructed from a sensing layer prepared by crosslinking two components together, for example: (1) a redox compound such as a redox polymer containing pendent Os polypyridyl complexes with oxidation potentials of about +200 mV vs. SCE, and (2) periodate oxidized horseradish peroxidase (HRP). Such a sensor functions in a reductive mode; the working electrode is controlled at a potential negative to that of the Os complex, resulting in mediated reduction of hydrogen peroxide through the HRP catalyst.

In another example, a potentiometric sensor can be constructed as follows. A glucose-sensing layer is constructed by crosslinking together (1) a redox polymer containing pendent Os polypyridyl complexes with oxidation potentials from about −200 mV to +200 mV vs. SCE, and (2) glucose oxidase. This sensor can then be used in a potentiometric mode, by exposing the sensor to a glucose containing solution, under conditions of zero current flow, and allowing the ratio of reduced/oxidized Os to reach an equilibrium value. The reduced/oxidized Os ratio varies in a reproducible way with the glucose concentration, and will cause the electrode's potential to vary in a similar way.

A sensor may also include an active agent such as an anticlotting and/or antiglycolytic agent(s) disposed on at least a portion of a sensor that is positioned in a user. An anticlotting agent may reduce or eliminate the clotting of blood or other body fluid around the sensor, particularly after insertion of the sensor. Examples of useful anticlotting agents include heparin and tissue plasminogen activator (TPA), as well as other known anticlotting agents. Embodiments may include an antiglycolytic agent or precursor thereof. Examples of antiglycolytic agents are glyceraldehyde, fluoride ion, and mannose.

Sensors may be configured to require no system calibration or no user calibration. For example, a sensor may be factory calibrated and need not require further calibrating. In certain embodiments, calibration may be required, but may be done without user intervention, i.e., may be automatic. In those embodiments in which calibration by the user is required, the calibration may be according to a predetermined schedule or may be dynamic, i.e., the time for which may be determined by the system on a real-time basis according to various factors, such as but not limited to glucose concentration and/or temperature and/or rate of change of glucose, etc.

Calibration may be accomplished using an in vitro test strip (or other reference), e.g., a small sample test strip such as a test strip that requires less than about 1 microliter of sample (for example FreeStyle® blood glucose monitoring test strips from Abbott Diabetes Care Inc.). For example, test strips that require less than about 1 nanoliter of sample may be used. In certain embodiments, a sensor may be calibrated using only one sample of body fluid per calibration event. For example, a user need only lance a body part one time to obtain sample for a calibration event (e.g., for a test strip), or may lance more than one time within a short period of time if an insufficient volume of sample is firstly obtained. Embodiments include obtaining and using multiple samples of body fluid for a given calibration event, where glucose values of each sample are substantially similar. Data obtained from a given calibration event may be used independently to calibrate or combined with data obtained from previous calibration events, e.g., averaged including weighted averaged, etc., to calibrate. In certain embodiments, a system need only be calibrated once by a user, where recalibration of the system is not required.

Analyte systems may include an optional alarm system that, e.g., based on information from a processor, warns the patient of a potentially detrimental condition of the analyte. For example, if glucose is the analyte, an alarm system may warn a user of conditions such as hypoglycemia and/or hyperglycemia and/or impending hypoglycemia, and/or impending hyperglycemia. An alarm system may be triggered when analyte levels approach, reach or exceed a threshold value. An alarm system may also, or alternatively, be activated when the rate of change, or acceleration of the rate of change, in analyte level increase or decrease approaches, reaches or exceeds a threshold rate or acceleration. A system may also include system alarms that notify a user of system information such as battery condition, calibration, sensor dislodgment, sensor malfunction, etc. Alarms may be, for example, auditory and/or visual. Other sensory-stimulating alarm systems may be used including alarm systems which heat, cool, vibrate, or produce a mild electrical shock when activated.

The subject disclosure also includes sensors used in sensor-based drug delivery systems. The system may provide a drug to counteract the high or low level of the analyte in response to the signals from one or more sensors. Alternatively, the system may monitor the drug concentration to ensure that the drug remains within a desired therapeutic range. The drug delivery system may include one or more (e.g., two or more) sensors, a processing unit such as a transmitter, a receiver/display unit, and a drug administration system. In some cases, some or all components may be integrated in a single unit. A sensor-based drug delivery system may use data from the one or more sensors to provide necessary input for a control algorithm/mechanism to adjust the administration of drugs, e.g., automatically or semi-automatically. As an example, a glucose sensor may be used to control and adjust the administration of insulin from an external or implanted insulin pump.

In certain embodiments, an analyte signal processing method may include determining a measurement time period, receiving a plurality of signals associated with a monitored analyte level during the determined measurement time period from an analyte sensor, modulating the received plurality of signals to generate a data stream over the measurement time period, and accumulating the generated data stream to determine an analyte signal corresponding to the monitored analyte level associated with the measurement time period.

Certain aspects may further include filtering the received plurality of signals associated with the monitored analyte level.

In certain embodiments, filtering may include bandpass filtering the plurality of signals.

In certain embodiments, modulating the received plurality of signals may include synchronizing each of the received plurality of signals with a corresponding clock signal to generate a respective frequency pulse.

In certain embodiments, the accumulated data stream may include maintaining a count of the number of generated frequency pulses during the measurement time period.

In certain embodiments, the determined analyte signal corresponding to the monitored analyte level may include an average value of the generated frequency pulses.

In certain embodiments, the received plurality of signals may be voltage signals, and further, modulating the generated data stream may include converting each of the voltage signals into a corresponding frequency pulse stream.

In certain aspects, the average of the frequency pulse stream for the measurement time period may correspond to the determined analyte level for the measurement time period.

In certain embodiments, the measurement time period may be programmable.

In certain embodiments, the measurement time period may be modified based, at least in part, on one or more characteristics of the analyte sensor.

Certain aspects may further include removing one or more signal artifacts from the received plurality of signals.

In certain embodiments, removing the one or more signal artifacts may include filtering the received plurality of signals prior to modulating the signals.

In certain embodiments, a signal processing device used for processing analyte related signals may include an analyte sensor interface electronics for receiving a plurality of analyte related signals from an analyte sensor over a measurement time period, and a data processing component operatively coupled to the analyte sensor interface electronics for processing the received plurality of analyte related signals, the data processing component including, a signal filtering component to filter the received plurality of analyte related signals, and a signal conversion component operatively coupled to the signal filtering component to convert the received filtered plurality of analyte related signals to determine an analyte level associated with a monitored analyte level during the measurement time period.

In certain embodiments, at least a portion of the one or more analyte sensor interface electronics or the data processing components may include an application specific integrated circuit.

In certain embodiments, the signal conversion component may include a clock to generate a plurality of clock signals.

In certain embodiments, the signal conversion component may synchronize each of the received filtered plurality of analyte related signals to the corresponding one of the generated plurality of clock signals.

In certain embodiments, the signal conversion component may generate a frequency data stream based on the received filtered plurality of analyte related signals.

In certain embodiments, each pulse in the frequency data stream may be associated with the respective one of the generated plurality of clock signals.

In certain embodiments, the signal conversion component may include a sigma delta modulation unit.

Certain aspects may include a communication component to transmit data associated with the determined analyte level over a communication connection.

In certain embodiments, the communication component may include an RF transmitter.

In certain embodiments, the communication connection may include one or more of a wired communication link or a wireless communication link.

In certain embodiments, the analyte sensor may include a glucose sensor.

In certain embodiments, the glucose sensor may include at least one working electrode in signal communication with the analyte sensor interface electronics.

In certain embodiments, the working electrode of the sensor may include one of carbon or gold.

In certain embodiments, an analyte monitoring system may include an analyte sensor including a working electrode having a sensing layer at least a portion of which is configured for fluid contact with an interstitial fluid under a skin layer, and a data processing unit comprising an application specific integrated circuit in signal communication with the analyte sensor for receiving a plurality of signals related to a monitored analyte level from the sensor over a monitoring time period, the data processing unit including a signal filtering component to filter the received plurality of signals, and a signal conversion component to convert the received filtered plurality of analyte related signals to determine a corresponding analyte level associated with a monitored analyte level during a measurement time period, said monitoring time period including multiple measurement time periods.

In certain embodiments, the signal conversion component may include a clock to generate a plurality of clock signals.

In certain embodiments, the signal conversion component may synchronize each of the received filtered plurality of analyte related signals to the corresponding one of the generated plurality of clock signals.

In certain embodiments, the signal conversion component may generate a frequency data stream based on the received filtered plurality of analyte related signals.

In certain embodiments, each pulse in the frequency data stream may be associated with the respective one of the generated plurality of clock signals.

In certain embodiments, the data processing unit may include a sigma delta modulator.

In certain embodiments, the analyte sensor may include a glucose sensor.

In certain embodiments, the working electrode of the sensor may include one of carbon or gold.

In certain embodiments, the sensing layer may include redox polymer.

In certain embodiments, the working electrode may be provided on the analyte sensor using laser ablation or photolithography.

Certain aspects may further include a receiver unit in signal communication with the data processing unit to receive a plurality of data corresponding to the monitored analyte level from the sensor or the data processing unit.

In certain embodiments, the receiver unit may include a strip port to receive an in vitro glucose test strip.

In certain embodiments, the analyte sensor may be calibrated based on the glucose measurement derived from the in vitro test strip.

In certain embodiments, the measurement time period may be approximately 30 seconds.

In certain embodiments, the monitoring time period may be between approximately five to seven days.

Various other modifications and alterations in the structure and method of operation of the embodiments of the present disclosure will be apparent to those skilled in the art without departing from the scope and spirit of the present disclosure. Although the present disclosure has been described in connection with certain embodiments, it should be understood that the present disclosure as claimed should not be unduly limited to such embodiments. It is intended that the following claims define the scope of the present disclosure and that structures and methods within the scope of these claims and their equivalents be covered thereby.

What is claimed is:

1. A glucose monitoring device, comprising:
a glucose sensor configured to be positioned at least in part in contact with a fluid under a skin layer of a user and generate analog signals indicative of a glucose level of the user;
a signal modulator to modulate the analog signals from the glucose sensor;
a clock to generate one or more clock signals corresponding to an analog-to-digital conversion time of the signal modulator;
one or more memories; and
one or more processors configured to:
obtain a measurement time period, wherein the measurement time period is determined based on the clock and a function of the analog-to-digital conversion time,
receive the analog signals during the measurement time period from the glucose sensor,
modulate the received analog signals using the signal modulator to generate a data stream at a signal resolution determined by a number of samples of the received analog signals obtained from the signal modulator over the measurement time period, wherein at least a portion of the data stream having a frequency that is a multiple of the analog-to-digital conversion time is filtered out, wherein the signal resolution is 15 bits,
sample the data stream at the signal resolution to generate glucose data indicative of the glucose level over the measurement time, and
store the glucose data in the one or more memories.

2. The device of claim 1, wherein the signal modulator is configured to generate the data stream synchronized with the one or more clock signals.

3. The device of claim 1, wherein the signal modulator comprises a Sigma-Delta modulator.

4. The device of claim 1, wherein the clock comprises a low frequency clock and the measurement time period is about 30 seconds.

5. The device of claim 1, wherein the stored glucose data comprises an average of signal counts obtained from the data stream over the measurement time.

6. The device of claim 1, wherein the measurement time period defines a filter frequency response of the glucose sensor.

7. The device of claim 1, wherein the one or more processors are further configured to filter one or more signal artifacts from the data stream over the measurement time period, the one or more signal artifacts including a signal transient.

8. The device of claim 1, wherein the glucose sensor comprises a plurality of electrodes including a working electrode comprising a glucose-responsive enzyme bonded to a polymer disposed on the working electrode.

9. The device of claim 8, wherein the glucose-responsive enzyme is chemically bonded to the polymer.

10. The device of claim 8, wherein the working electrode further comprises a mediator.

11. The device of claim 1, wherein the glucose sensor comprises a plurality of electrodes including a working electrode comprising a mediator bonded to a polymer disposed on the working electrode.

12. The device of claim 11, wherein the mediator is chemically bonded to the polymer.

13. The device of claim 11, wherein the mediator is crosslinked with the polymer.

14. The device of claim 1, wherein the one or more processors are configured to send the stored glucose data to a receiving unit comprising an output configured to display the glucose level based on the stored glucose data.

15. The device of claim 1, wherein the one or more processors are configured to receive one or more values associated with the glucose level wirelessly over a communication link.

16. The device of claim 1, wherein the one or more processors are configured to convert the analog signals during the measurement time period to corresponding digital signals.

17. The device of claim 16, wherein the one or more processors are configured to perform filtering and data packing on the converted data for wireless transmission.

18. A method for monitoring a glucose level of a user, comprising:
generating, by a clock, one or more clock signals corresponding to an analog-to-digital conversion time of a signal modulator;
obtaining a measurement time period, wherein the measurement time period is determined based on the clock and a function of the analog-to-digital conversion time;
receiving analog signals during the measurement time period from a glucose sensor positioned at least in part in contact with a fluid under a skin layer of a user, the analog signals indicative of glucose level of a user;
modulating, by the signal modulator, the received analog signals to generate a data stream at a signal resolution determined by a number of samples of the received analog signals obtained from the signal modulator over the measurement time period, wherein at least a portion of the data stream having a frequency that is a multiple of the analog-to-digital conversion time is filtered out, wherein the signal resolution is 15 bits;
sampling the data stream at the signal resolution to generate glucose data indicative of the glucose level over the measurement time; and
storing the glucose data in one or more memories.

19. The method of claim 18, wherein the signal modulator is configured to generate the data stream synchronized with the one or more clock signals.

20. The method of claim 18, wherein the signal modulator comprises a Sigma-Delta modulator.

21. The method of claim 18, wherein the clock comprises a low frequency clock and the measurement time period is about 30 seconds.

22. The method of claim 18, wherein the stored glucose data comprises an average of signal counts obtained from the data stream over the measurement time.

23. The method of claim 18, wherein the measurement time period defines a filter frequency response of the glucose sensor.

24. The method of claim 18, further comprising filtering one or more signal artifacts from the data stream over the measurement time period, the one or more signal artifacts including a signal transient.

25. The method of claim 18, further comprising sending the stored glucose data to a receiving unit comprising an output configured to display the glucose level based on the stored glucose data.

26. The method of claim 18, further comprising receiving one or more values associated with the glucose level wirelessly over a communication link.

27. The method of claim 18, further comprising converting the analog signals during the measurement time period to corresponding digital signals.

28. The method of claim 18, further comprising filtering and data packing the converted data for wireless transmission.

29. The device of claim 1, wherein the clock comprises a low frequency clock at 1024 Hz.

30. The device of claim 1, wherein the measurement time period is 30 seconds.

* * * * *